US008273348B2

(12) United States Patent
Svendsen et al.

(10) Patent No.: US 8,273,348 B2
(45) Date of Patent: Sep. 25, 2012

(54) LIPASE VARIANTS FOR PHARMACEUTICAL USE

(75) Inventors: Allan Svendsen, Hoersholm (DK); Michael Skjoet, Jyllinge (DK); Debbie Yaver, Davis, CA (US); Lars Lehmann Hylling Christensen, Alleroed (DK); Signe Eskildsen Larsen, Lyngby (DK); Nina Lundin, Frederiksberg C (DK); Michael Lamsa, Davis, CA (US); Peter Colin Gregory, Hannover (DE)

(73) Assignees: Novozymes A/S, Bagsvaerd (DK); Novozymes Inc., Davis, CA (US)

(*) Notice: Subject to any disclaimer, the term of this patent is extended or adjusted under 35 U.S.C. 154(b) by 345 days.

(21) Appl. No.: 12/519,868

(22) PCT Filed: Dec. 12, 2007

(86) PCT No.: PCT/US2007/087168

§ 371 (c)(1), (2), (4) Date: Aug. 10, 2009

(87) PCT Pub. No.: WO2008/079685

PCT Pub. Date: Jul. 3, 2008

(65) Prior Publication Data

US 2010/0034797 A1 Feb. 11, 2010

Related U.S. Application Data

(60) Provisional application No. 60/871,196, filed on Dec. 21, 2006.

(51) Int. Cl.

| | |
|---|---|
| ***A61K 38/54*** | (2006.01) |
| ***A61K 38/46*** | (2006.01) |
| ***C12Q 1/34*** | (2006.01) |
| ***C12Q 1/40*** | (2006.01) |
| ***C12N 9/20*** | (2006.01) |
| ***C12N 9/14*** | (2006.01) |
| ***C12N 9/26*** | (2006.01) |
| ***C07H 21/04*** | (2006.01) |
| ***C07K 1/00*** | (2006.01) |

(52) U.S. Cl. .......... 424/94.2; 424/94.6; 435/18; 435/22; 435/198; 435/195; 435/201; 536/23.2; 530/350

(58) Field of Classification Search ................. 424/94.2, 424/94.6; 435/18, 22, 198, 195, 201; 536/23.2; 530/350

See application file for complete search history.

(56) References Cited

U.S. PATENT DOCUMENTS

| | | | | |
|---|---|---|---|---|
| 5,869,438 | A * | 2/1999 | Svendsen et al. | 510/226 |
| 6,495,357 | B1 | 12/2002 | Fuglsang | |
| 6,939,702 | B1 * | 9/2005 | Vind et al. | 435/198 |
| 7,226,770 | B2 * | 6/2007 | Roggen | 435/196 |
| 7,465,570 | B2 * | 12/2008 | Borch et al. | 435/196 |
| 2005/0059130 | A1 | 3/2005 | Bojsen | |
| 2007/0173430 | A1 | 7/2007 | Souter | |
| 2009/0047266 | A1 * | 2/2009 | Svendsen et al. | 424/94.2 |

FOREIGN PATENT DOCUMENTS

| | | |
|---|---|---|
| EP | 0 600 868 | 4/1999 |
| EP | 1 428 874 | 6/2004 |
| WO | WO 92/05249 | 4/1992 |
| WO | WO 92/19726 | 11/1992 |
| WO | WO 94/25577 | 11/1994 |
| WO | WO 95/09909 | 4/1995 |
| WO | WO 95/22615 | 8/1995 |
| WO | WO 97/04079 | 2/1997 |
| WO | WO 97/07202 | 2/1997 |
| WO | WO 99/42566 | 8/1999 |
| WO | WO 00/32758 | 6/2000 |
| WO | WO 00/54799 | 9/2000 |
| WO | WO 00/60063 | 10/2000 |
| WO | WO 01/83559 | 11/2001 |
| WO | WO 02/055679 | 7/2002 |
| WO | WO 02/060474 | 8/2002 |
| WO | WO 02/062973 | 8/2002 |
| WO | WO 03/060112 | 7/2003 |
| WO | WO 2004/099400 | 11/2004 |
| WO | WO 2004/111216 | 12/2004 |
| WO | WO 2006/136159 | 12/2006 |

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

(Continued)

*Primary Examiner* — Ganapathirama Raghu

(74) *Attorney, Agent, or Firm* — Kristin J. McNamara

(57) ABSTRACT

The pharmaceutical use of lipases related to the *Thermomyces lanuginosus* (*Humicola lanuginosa*) lipase comprising amino acids 1-269 of SEQ ID NO: 2, optionally in combination with a protease and/or an amylase. Examples of medical indications are: Treatment of digestive disorders, pancreatic exocrine insufficiency (PEI), pancreatitis, cystic fibrosis, diabetes type I, and/or diabetes type II. The lipases of the invention have, e.g., an improved digestion performance in vitro, an improved activity at a pH in the neutral range, an improved stability at low pH, an are stable against protease-degradation, and/or are stable in the presence of pepsin and bile salts. The invention also relates to methods of determining digestion performance in vitro of lipases, as well as to certain novel variants of the lipase of *T. lanuginosus.*

25 Claims, No Drawings

OTHER PUBLICATIONS

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Svendsen, Allan, "Lipase Protein Engineering", Biochimica et Biophysica ACTA, vol. 1543, No. 2, pp. 223-238 (2000).

International Search Report for corresponding application No. PCT/US2007/087168 dated Sep. 11, 2008.

Tsukamoto et al., EMBL Acces No. M18862 (1988).

Sidhu et al., EMBL Acces No. L29018 (1994).

Da Silva et al., EMBL Acces No. AF032864 (1997).

Goldstein et al., EMBL Access No. AF282895 (2000).

Mitsuiki et al., EMBL Acces No. AY151208 (2002).

Rivera et al., EMBL Access No. AY630336 (2003).

* cited by examiner

SEQUENCE LISTING

```
<160> NUMBER OF SEQ ID NOS: 8

<210> SEQ ID NO 1
<211> LENGTH: 274
<212> TYPE: PRT
<213> ORGANISM: Humicola lanuginosa
<220> FEATURE:
<221> NAME/KEY: VARIANT
<222> LOCATION: (1)..(274)
<220> FEATURE:
<221> NAME/KEY: mat_peptide
<222> LOCATION: (6)..(274)

<400> SEQUENCE: 1

Ser Pro Ile Arg Arg Glu Val Ser Gln Asp Leu Phe Asn Gln Phe Asn
-5              -1  1               5                   10

Leu Phe Ala Gln Tyr Ser Ala Ala Ala Tyr Cys Gly Lys Asn Asn Asp
            15                  20                  25

Ala Pro Ala Gly Thr Asn Ile Thr Cys Thr Gly Asn Ala Cys Pro Glu
```

```
        30                  35                  40

Val Glu Lys Ala Asp Ala Thr Phe Leu Tyr Ser Phe Glu Asp Ser Gly
    45                  50                  55

Val Gly Asp Val Thr Gly Phe Leu Ala Leu Asp Asn Thr Asn Lys Leu
60                  65                  70                  75

Ile Val Leu Ser Phe Arg Gly Ser Arg Ser Ile Glu Asn Trp Ile Gly
                80                  85                  90

Asn Leu Asn Phe Asp Leu Lys Glu Ile Asn Asp Ile Cys Ser Gly Cys
            95                  100                 105

Arg Gly His Asp Gly Phe Thr Ser Ser Trp Arg Ser Val Ala Asp Thr
        110                 115                 120

Leu Arg Gln Lys Val Glu Asp Ala Val Arg Glu His Pro Asp Tyr Arg
    125                 130                 135

Val Val Phe Thr Gly His Ser Leu Gly Gly Ala Leu Ala Thr Val Ala
140                 145                 150                 155

Gly Ala Asp Leu Arg Gly Asn Gly Tyr Asp Ile Asp Val Phe Ser Tyr
                160                 165                 170

Gly Ala Pro Arg Val Gly Asn Arg Ala Phe Ala Glu Phe Leu Thr Val
            175                 180                 185

Gln Thr Gly Gly Thr Leu Tyr Arg Ile Thr His Thr Asn Asp Ile Val
        190                 195                 200

Pro Arg Leu Pro Pro Arg Glu Phe Gly Tyr Ser His Ser Ser Pro Glu
    205                 210                 215

Tyr Trp Ile Lys Ser Gly Thr Leu Val Pro Val Arg Arg Arg Asp Ile
220                 225                 230                 235

Val Lys Ile Glu Gly Ile Asp Ala Thr Gly Gly Asn Asn Gln Pro Asn
                240                 245                 250

Ile Pro Asp Ile Pro Ala His Leu Trp Tyr Phe Gly Leu Ile Gly Thr
            255                 260                 265

Cys Leu


<210> SEQ ID NO 2
<211> LENGTH: 269
<212> TYPE: PRT
<213> ORGANISM: Humicola lanuginosa
<220> FEATURE:
<221> NAME/KEY: mat_peptide
<222> LOCATION: (1)..(269)

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125
```

```
Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265


<210> SEQ ID NO 3
<211> LENGTH: 274
<212> TYPE: PRT
<213> ORGANISM: Bacillus licheniformis
<220> FEATURE:
<221> NAME/KEY: mat_peptide
<222> LOCATION: (1)..(274)

<400> SEQUENCE: 3

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220
```

His Val Ala Gly Ala Ala Ala Leu Ile Leu Ser Lys His Pro Asn Leu
225 230 235 240

Ser Ala Ser Gln Val Arg Asn Arg Leu Ser Ser Thr Ala Thr Tyr Leu
245 250 255

Gly Ser Ser Phe Tyr Tyr Gly Lys Gly Leu Ile Asn Val Glu Ala Ala
260 265 270

Ala Gln

<210> SEQ ID NO 4
<211> LENGTH: 188
<212> TYPE: PRT
<213> ORGANISM: Nocardiopsis sp.
<220> FEATURE:
<221> NAME/KEY: mat_peptide
<222> LOCATION: (1)..(188)

<400> SEQUENCE: 4

Ala Asp Ile Ile Gly Gly Leu Ala Tyr Thr Met Gly Gly Arg Cys Ser
1 5 10 15

Val Gly Phe Ala Ala Thr Asn Ala Ala Gly Gln Pro Gly Phe Val Thr
20 25 30

Ala Gly His Cys Gly Arg Val Gly Thr Gln Val Thr Ile Gly Asn Gly
35 40 45

Arg Gly Val Phe Glu Gln Ser Val Phe Pro Gly Asn Asp Ala Ala Phe
50 55 60

Val Arg Gly Thr Ser Asn Phe Thr Leu Thr Asn Leu Val Ser Arg Tyr
65 70 75 80

Asn Thr Gly Gly Tyr Ala Thr Val Ala Gly His Asn Gln Ala Pro Ile
85 90 95

Gly Ser Ser Val Cys Arg Ser Gly Ser Thr Thr Gly Trp His Cys Gly
100 105 110

Thr Ile Gln Ala Arg Gly Gln Ser Val Ser Tyr Pro Glu Gly Thr Val
115 120 125

Thr Asn Met Thr Arg Thr Thr Val Cys Ala Glu Pro Gly Asp Ser Gly
130 135 140

Gly Ser Tyr Ile Ser Gly Thr Gln Ala Gln Gly Val Thr Ser Gly Gly
145 150 155 160

Ser Gly Asn Cys Arg Thr Gly Gly Thr Thr Phe Tyr Gln Glu Val Thr
165 170 175

Pro Met Val Asn Ser Trp Gly Val Arg Leu Arg Thr
180 185

<210> SEQ ID NO 5
<211> LENGTH: 188
<212> TYPE: PRT
<213> ORGANISM: Nocardiopsis dassonvillei subsp. dassonvillei
<220> FEATURE:
<221> NAME/KEY: mat_peptide
<222> LOCATION: (1)..(188)

<400> SEQUENCE: 5

Ala Asp Ile Ile Gly Gly Leu Ala Tyr Tyr Met Gly Gly Arg Cys Ser
1 5 10 15

Val Gly Phe Ala Ala Thr Asn Ser Ala Gly Gln Pro Gly Phe Val Thr
20 25 30

Ala Gly His Cys Gly Thr Val Gly Thr Gly Val Thr Ile Gly Asn Gly
35 40 45

Thr Gly Thr Phe Gln Asn Ser Val Phe Pro Gly Asn Asp Ala Ala Phe

```
    50                  55                  60

Val Arg Gly Thr Ser Asn Phe Thr Leu Thr Asn Leu Val Ser Arg Tyr
65                  70                  75                  80

Asn Ser Gly Gly Tyr Gln Ser Val Thr Gly Thr Ser Gln Ala Pro Ala
                85                  90                  95

Gly Ser Ala Val Cys Arg Ser Gly Ser Thr Thr Gly Trp His Cys Gly
            100                 105                 110

Thr Ile Gln Ala Arg Asn Gln Thr Val Arg Tyr Pro Gln Gly Thr Val
        115                 120                 125

Tyr Ser Leu Thr Arg Thr Asn Val Cys Ala Glu Pro Gly Asp Ser Gly
    130                 135                 140

Gly Ser Phe Ile Ser Gly Ser Gln Ala Gln Gly Val Thr Ser Gly Gly
145                 150                 155                 160

Ser Gly Asn Cys Ser Val Gly Gly Thr Thr Tyr Tyr Gln Glu Val Thr
                165                 170                 175

Pro Met Ile Asn Ser Trp Gly Val Arg Ile Arg Thr
            180                 185


<210> SEQ ID NO 6
<211> LENGTH: 513
<212> TYPE: PRT
<213> ORGANISM: Bacillus stearothermophilus
<220> FEATURE:
<221> NAME/KEY: VARIANT
<222> LOCATION: (1)..(513)
<220> FEATURE:
<221> NAME/KEY: mat_peptide
<222> LOCATION: (1)..(513)

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

Asn Tyr Asp Tyr Leu Met Tyr Ala Asp Leu Asp Met Asp His Pro Glu
        195                 200                 205

Val Val Thr Glu Leu Lys Asn Trp Gly Lys Trp Tyr Val Asn Thr Thr
```

```
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
            260                 265                 270

Asn Tyr Ile Thr Lys Thr Asp Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
        435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro Ile Thr Thr Arg Pro
                485                 490                 495

Trp Thr Gly Glu Phe Val Arg Trp Thr Glu Pro Arg Leu Val Ala Trp
            500                 505                 510

Pro


<210> SEQ ID NO 7
<211> LENGTH: 481
<212> TYPE: PRT
<213> ORGANISM: Bacillus licheniformis
<220> FEATURE:
<221> NAME/KEY: VARIANT
<222> LOCATION: (1)..(481)

<400> SEQUENCE: 7

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Thr Ser
        35                  40                  45

Gln Ala Asp Val Gly Tyr Gly Ala Tyr Asp Leu Tyr Asp Leu Gly Glu
    50                  55                  60
```

-continued

```
Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Gly Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190

Tyr Leu Met Tyr Ala Asp Ile Asp Tyr Asp His Pro Asp Val Val Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg
```

<210> SEQ ID NO 8
<211> LENGTH: 483
<212> TYPE: PRT
<213> ORGANISM: Bacillus sp.
<220> FEATURE:
<221> NAME/KEY: VARIANT
<222> LOCATION: (1)..(483)

<400> SEQUENCE: 8

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Lys His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365
```

-continued

```
Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Asn Lys Trp Met Phe Val Gly Arg Asn Lys Ala Gly Gln Val
        435                 440                 445

Trp Thr Asp Ile Thr Gly Asn Lys Ala Gly Thr Val Thr Ile Asn Ala
    450                 455                 460

Asp Gly Trp Gly Asn Phe Ser Val Asn Gly Gly Ser Val Ser Ile Trp
465                 470                 475                 480

Val Asn Lys
```

LIPASE VARIANTS FOR PHARMACEUTICAL USE

CROSS-REFERENCE TO RELATED APPLICATIONS

This application is a 35 U.S.C. 371 national application of PCT/US2007/087168 filed 12 Dec. 2007, which claims priority or the benefit under 35 U.S.C. 119 of U.S. provisional application No. 60/871,196 filed 21 Dec. 2006, the contents of which are fully incorporated herein by reference.

REFERENCE TO A SEQUENCE LISTING

This application contains a Sequence Listing in computer readable form. The computer readable form is incorporated herein by reference.

TECHNICAL FIELD

The present invention relates to a lipase for use as a medicament, which lipase (a) has at least 50% identity to the sequence of amino acids 1 to 269 of SEQ ID NO: 2; (b) has lipase activity; and which (c) as compared to the sequence of amino acids 1-269 of SEQ ID NO:2, comprises substitutions N33Q, T231R, and N233R, as well as at least one additional substitution selected from the following: E1*,D,N; Q4H,P,R; D5E; N8L,Q; Q9H; F10L; N11C,D,H,L,P,Q,R,S; G23E; N26A,H,I; D27I,N,Q,R,S,V; P29T; A30T,V; T37K,M; G38A,D,F,H,I,K,L,M,N,P,Q,S,T,W,Y; N39H,S; E43K; K46M; A49T; L52I,R; E56K,Q,R,S; D57G,N; V60E,S; G61R; V63R; A68V; L69I; N71I,S; N73Q,Y; I76T; R84E; I86F,L; E87A,H,K,R; 190L,V; G91A,C,E,F,K,L,M,N,S,T,V,W,Y; L93*,F; N94*,K,Q,R,S; F95*; D96*,E,G,N,R,S,W,Y; L97M,Q; K98I,T; E99D; N101Q; D102E,G,Y; R108M; G109A; D111A,E,N,S; G112A; T114I; S115L; W117C,D,E,F,G,H,I,K,L,P,S,T,V,Y; D122E,N; Q126L; V128A; D130H; H135D; P136H; Y138F; V141E,L; A150V; V154F,I,L; A155V; G156R; G161A,E; N162G,S,T; G163A,C,D,E,H,I,K,L,M,N,P,Q,R,S,T,V,W,Y; D167E; V168M; V176A,D,F,G,H,I,K,M,N,Q,T,W; G177A; R179T; L185M; G190C,D; N200Q,S; R205I; L206F; E210D,R,V,Y; S216P; E219D; G225P; T226N; L227F,G; P229R; E239D; G240L; D242E; T244S; G246A; Q249R; N251Q,S; D254A,G,I,K,L,M,N,R,Q,S,Y; I255A,F; P256A,F,G,H,I,L,M,N,Q,S,T,V,W,Y; and L269F,H.

The invention also relates to pharmaceutical compositions comprising these lipases, as well as to some of these lipases as such.

The invention furthermore relates to methods of determining, and optionally comparing, digestion performance in vitro of lipases.

The lipases of the invention may be used in combination with a protease and/or an amylase. Examples of medical indications are: Treatment of digestive disorders, pancreatic exocrine insufficiency (PEI), pancreatitis, cystic fibrosis, diabetes type I, and/or diabetes type II.

The lipase of SEQ ID NO: 2 is a wild type lipase derived from *Humicola lanuginosa* DSM 4109 (synonym: *Thermomyces lanuginosus*).

BACKGROUND ART

U.S. Pat. No. 5,614,189 (EP 600868 B1) describes the use of, i.a., a lipase derived from *Humicola lanuginosa* in pancreatic enzyme replacement therapy, for example in the treatment of patients suffering from cystic fibrosis. This lipase is from *Humicola lanuginosa* DSM 4109 and has the amino acid sequence of amino acids 1-269 of SEQ ID NO: 2.

WO 92/05249, WO 92/19726, WO 94/25577, WO 95/09909, WO 95/22615, WO 97/04079, WO 97/07202, WO 99/42566, WO 00/32758, WO 00/60063, WO 01/83559, WO 01/83559, WO 2002/055679, WO 2002/062973, WO 2002/062973, WO 2004/099400, and WO 2004/111216 describe a number of variants of SEQ ID NO: 2, but not the pharmaceutical use thereof.

WO 2006/136159 describes the pharmaceutical use of the lipase having amino acids 1-269 of SEQ ID NO: 1, as well as variant N33Q thereof.

There is a need in the art for improved lipases for pharmaceutical use.

SUMMARY OF THE INVENTION

The present invention provides improved lipases for pharmaceutical use. Preferably, the enzymes for use according to the invention have an improved efficacy in vivo and/or in vitro; an improved activity; an improved stability; are stable against degradation by proteases; are stable in the presence of bile salts; and/or have a reduced allergenicity. More preferably, the lipases of the invention have an improved digestion performance in vitro, as compared to a reference lipase having the sequence of SEQ ID NO: 2 with the following substitutions: N33Q+T231R+N233R.

The present invention relates to a lipase for use as a medicament, which lipase (a) has at least 50% identity to the sequence of amino acids 1 to 269 of SEQ ID NO: 2; (b) has lipase activity; and which (c) as compared to the sequence of amino acids 1-269 of SEQ ID NO:2, comprises substitutions N33Q, T231R, and N233R, as well as at least one additional substitution selected from the following: E1*,D,N; Q4H,P,R; D5E; N8L,Q; Q9H; F10L; N11C,D,H,L,P,Q,R,S; G23E; N26A,H,I; D27I,N,Q,R,S,V; P29T; A30T,V; T37K,M; G38A,D,F,H,I,K,L,M,N,P,Q,S,T,W,Y; N39H,S; E43K; K46M; A49T; L52I,R; E56K,Q,R,S; D57G,N; V60E,S; G61R; V63R; A68V; L69I; N71I,S; N73Q,Y; I76T; R84E; I86F,L; E87A,H,K,R; 190L,V; G91A,C,E,F,K,L,M,N,S,T,V,W,Y; L93*,F; N94*,K,Q,R,S; F95*; D96*,E,G,N,R,S,W,Y; L97M,Q; K98I,T; E99D; N101Q; D102E,G,Y; R108M; G109A; D111A,E,N,S; G112A; T114I; S115L; W117C,D,E,F,G,H,I,K,L,P,S,T,V,Y; D122E,N; Q126L; V128A; D130H; H135D; P136H; Y138F; V141E,L; A150V; V154F,I,L; A155V; G156R; G161A,E; N162G,S,T; G163A,C,D,E,H,I,K,L,M,N,P,Q,R,S,T,V,W,Y; D167E; V168M; V176A,D,F,G,H,I,K,M,N,Q,T,W; G177A; R179T; L185M; G190C,D; N200Q,S; R205I; L206F; E210D,R,V,Y; S216P; E219D; G225P; T226N; L227F,G; P229R; E239D; G240L; D242E; T244S; G246A; Q249R; N251Q,S; D254A,G,I,K,L,M,N,R,Q,S,Y; I255A,F; P256A,F,G,H,I,L,M,N,Q,S,T,V,W,Y; and L269F,H.

The invention furthermore relates to the use of such lipases for the manufacture of a medicament for the treatment of digestive disorders, PEI, pancreatitis, cystic fibrosis, diabetes type I, and/or diabetes type II, these uses optionally further comprising the use of a protease, and/or an amylase; as well as to such lipases for use in the treatment of these conditions, optionally in combination with a protease and/or an amylase.

The invention furthermore relates to a pharmaceutical composition comprising such lipases, together with at least one pharmaceutically acceptable auxiliary material, optionally including a protease and/or an amylase.

The invention also relates to a method for the treatment of digestive disorders, PEI, pancreatitis (acute and/or chronic), cystic fibrosis, diabetes type I, and/or diabetes type II, by administering a therapeutically effective amount of such lipases, optionally together with a protease and/or an amylase.

Finally, the invention relates to methods for determining, and optionally comparing, lipase digestion performances in vitro; as well as to certain lipases as such, e.g.:

A lipase which (a) has at least 50% identity to the sequence of amino acids 1-269 of SEQ ID NO: 2; (b) has lipase activity; and which, (c) as compared to the sequence of amino acids 1-269 of SEQ ID NO: 2, comprises a substitution in at least one position selected from the following: 9, 30, 38, 39, 63, 112, 114, 115, 117, 122, 128, 130, 136, 154, 155, 156, 161, 163, 168, 185, 190, 239, and 246; and A lipase which (a) has at least 50% identity to the sequence of amino acids 1-269 of SEQ ID NO: 2; (b) has lipase activity; and which, (c1) as compared to the sequence of amino acids 1-269 of SEQ ID NO: 2, comprises at least one substitution selected from the following: E1N; Q4H; N8L,Q; Q9H; N11C,D,H,L,P,S; G23E; D27I; P29T; A30T,V; T37K,M; G38A,D,F,H,I,K,L,M,N,P,Q,S,T,W,Y; N39H,S; D57N; G61R; V63R; N71I,S; N73Q,Y; I76T; I86F,L; E87H; G91F,K,L,M,V,Y; N94Q; F95*; D96*; N101Q; D111E; G112A; T114I; S115L; W117C,D,E,F,G,H,I,K,L,P,S,T,V,Y; D122E,N; Q126L; V128A, D130H, H135D, P136H; V141E,L; V154F,I,L; A155V; G156R; G161A,E; N162G,S; G163A,C,D,E,H,I,K,L,M,N,P,Q,R,S,T,V,W,Y; V168M; L185M; G190C,D; R205I; G240L; G246A; N251Q,S; and L269F,H; or which, (c2) as compared to the sequence of amino acids 1-269 of SEQ ID NO: 2, comprises at least one of the following amino acids at the indicated position: 1N; 4H; 8L,Q; 9H; 11C,D,H,L,P,S; 23E; 27I; 29T; 30T,V; 37K,M; 38A,D,F,H,I,K,L,M,N,P,Q,S,T,W,Y; 39H,S; 57N; 61R; 63R; 71I,S; 73Q,Y; 76T; 86F,L; 87H; 91F,K,L,M,V,Y; 94Q; 95*; 96*; 101Q; 111E; 112A; 114I; 115L; 117C,D,E,F,G,H,I,K,L,P,S,T,V,Y; 122E,N; 126L; 128A, 130H, 135D, 136H; 141E,L; 154F,I,L; 155V; 156R; 161A,E; 162G,S; 163A,C,D,E,H,I,K,L,M,N,P,Q,R,S,T,V,W,Y; 168M; 185M; 190C,D; 205I; 240L; 246A; 251Q,S; and 269F,H.

DETAILED DESCRIPTION OF THE INVENTION

Lipases

A lipase is a polypeptide having lipase activity. In what follows, the lipase for use in the compositions, methods and uses of the invention is referred to as the lipase of the invention. The lipase of the invention may be a carboxylic ester hydrolase EC 3.1.1.-, which includes activities such as EC 3.1.1.3 triacylglycerol lipase, EC 3.1.1.4 phospholipase A2, EC 3.1.1.5 lysophospholipase, EC 3.1.1.26 galactolipase, EC 3.1.1.32 phospholipase A1, EC 3.1.1.73 feruloyl esterase. In a particular embodiment, the lipase is an EC 3.1.1.3 triacylglycerol lipase. In another particular embodiment, the lipase has EC 3.1.1.4 phospholipase A2 activity, i.e., catalyzes the reaction: Phosphatidylcholine+H(2)O=1-acylglycerophosphocholine+a carboxylate (removes the fatty acid attached to the 2-position). In a still further particular embodiment, the lipase has EC 3.1.1.32 phospholipase A1 activity, i.e., catalyzes the reaction: Phosphatidylcholine+H(2)O=2-acylglycerophosphocholine+a carboxylate.

The EC number refers to Enzyme Nomenclature 1992 from NC-IUBMB, Academic Press, San Diego, Calif., including supplements 1-5 published in *Eur. J. Biochem.*, 1994, 223: 1-5; *Eur. J. Biochem.*, 1995, 232: 1-6; *Eur. J. Biochem.*, 1996, 237: 1-5; *Eur. J. Biochem.*, 1997, 250: 1-6; and *Eur. J. Biochem.*, 1999, 264: 610-650; respectively. The nomenclature is regularly supplemented and updated; see, e.g., the World Wide Web at www.chem.qmw.ac.uk/iubmb/enzyme/index.html.

The lipase of the invention may be a variant of a parent lipase.

Variant

The term variant is defined herein as a lipase comprising one or more alterations, such as substitutions, insertions, deletions, and/or truncations of one or more specific amino acid residues at one or more specific positions in the polypeptide, as compared to a parent lipase.

Parent Lipase

The term parent lipase refers to the polypeptide with which a variant is compared and aligned. A particular example of a parent lipase is the lipase to which modifications, e.g., substitution(s), insertion(s), deletion(s), and/or truncation(s), are made to produce the lipase variants of the present invention. The parent may be a naturally occurring (wild-type) lipase, or it may be a variant thereof, prepared by any suitable means. A parent may also be an allelic variant which is a polypeptide encoded by any of two or more alternative forms of a gene occupying the same chromosomal locus.

In a particular embodiment, the parent lipase is a fungal lipase with an amino acid sequence having at least 50% identity to the sequence of amino acids 1-269 of the *T. lanuginosus* lipase shown in SEQ ID NO: 2. The parent lipase may be a yeast lipase such as a *Candida, Kluyveromyces, Pichia, Saccharomyces, Schizosaccharomyces*, or *Yarrowia* polypeptide; or, more preferably, a filamentous fungal lipase such as an *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma lipase*—or a variant of any of these. A preferred parent lipase is an ascomycete lipase, preferably derived from a strain of *Humicola, Talaromyces* or *Thermomyces*, e.g., from a strain of *Humicola fuscoatra, Humicola grisea, Humicola insolens, Humicola lutea, Humicola nigrescens, Humicola* sp., *Humicola lanuginosa* (*Thermomyces lanoginosus*), *Thermomyces ibadanensis, Thermomyces veffucosus, Talaromyces thermophilus, Talaromyces emersonii*, or *Talaromyces byssochlamydoides* or variants of any of these. In a particular embodiment, the parent lipase is (i) the *Humicola lanuginosa* lipase having amino acids 1 to 269 of SEQ ID NO: 2, or (ii) a variant thereof.

Nomenclature of Lipase Variants

In the present invention, a specific numbering of amino acid residue positions in the lipase variants is employed. By aligning the amino acid sequences of known lipases, it is possible to designate an amino acid position number to any amino acid residue in any lipase enzyme.

Using the numbering system originating from the amino acid sequence of the lipase disclosed in SEQ ID NO: 2, aligned with the amino acid sequence of another lipase using the alignment procedure herein described, it is possible to indicate the position of each amino acid residue in any other lipase. Accordingly, for any lipase of the invention which is compared with the sequence of amino acids 1-269 of SEQ ID NO: 2, each position and/or substitution corresponds to a position of amino acids 1-269 of SEQ ID NO: 2.

In describing the various lipase variants of the present invention, the nomenclature described below is adapted for ease of reference. In all cases, the accepted IUPAC single letter or triple letter amino acid abbreviation is employed.

For an amino acid substitution, the following nomenclature is used: Original amino acid, position, substituted amino acid.

Accordingly, the substitution of asparagine with isoleucine at position 26 is designated as N26I. Multiple mutations are separated by addition marks (+), e.g., N33Q+E210D+T231R+N233R represent mutations at positions 33, 210, 231, and 233 substituting asparagine (N) with glutamine (Q), glutamic acid (E) with aspartic acid (D), threonine (T) with arginine (R), and asparagine (N) with arginine (R), respectively.

For an amino acid deletion, the following nomenclature is used: Original amino acid, position,*. Accordingly, the deletion of glutamic acid (E) at position 1 is designated as "E1*". Multiple deletions are separated by addition marks ("+"), e.g. the deletion of leucine (L), asparagine (N), phenylalanine (F), and aspartic acid (D) in positions 93, 94, 95, and 96, respectively, is designated as "L93*+N94*+F95*+D96*".

Accordingly, for the present purposes, a deletion can in fact be considered an example of a substitution, viz. a substitution of the original amino acid with nothing. The following variant of the lipase of amino acids 1-269 of SEQ ID NO: 2 can therefore be said to include 11 substitutions in total: 7 substitutions into another amino acid, and 4 substitutions into nothing, i.e., 4 deletions: D27R+N33Q+G91A+L93*+N94*+F95*+D96*+D111A+T231R+N233R+P256T.

Therefore, when a specific amino acid can be substituted with two or more different amino acids or deleted, this is indicated as a substitution, where the alternative substituents including the deletion are separated by commas. For example, the designation "E1*,D,N" means that glutamine at position 1 in the parent lipase (E1) may be substituted with nothing (i.e., deleted) (*), substituted with aspartic acid (D), or substituted with asparagine (N).

Alignment and Identity Calculation

This section applies to the lipases, amylases, and proteases of the present invention (the enzymes of the invention).

The relatedness between two amino acid sequences is described by the parameter "identity".

For purposes of the present invention, the alignment of two amino acid sequences is determined by using the Needle program from the EMBOSS package (available on the Internet at emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence"; e.g. variant LVA023 having the sequence of amino acids 1-269 of SEQ ID NO: 2 with the following four substitutions: N33Q+E210D+T231R+N233R) and a different amino acid sequence ("foreign sequence"; e.g. amino acids 1-269 of SEQ ID NO: 2) is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|") The length of a sequence is the number of amino acid residues in the sequence (e.g. the length of SEQ ID NO: 2 is 269).

In the, purely hypothetical, alignment example below, the overlap is the amino acid sequence "HTWGER-NL" of Sequence 1; or the amino acid sequence "HGWGEDANL" of Sequence 2. In the example a gap is indicated by a "-".

Hypothetical alignment example:

```
Sequence 1: ACMSHTWGER-NL
                |   |||   ||
Sequence 2:     HGWGEDANLAMNPS
```

Accordingly, the percentage of identity of Sequence 1 to Sequence 2 is 6/12=0.5, corresponding to 50%.

In a particular embodiment, the percentage of identity of an amino acid sequence of a polypeptide with, or to, amino acids 1-269 of SEQ ID NO: 2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In a preferred embodiment, the lipase of the invention is at least 51% identical to the lipase having amino acids 1-269 of SEQ ID NO: 2. In additional preferred embodiments, it is at least 52%, 53%, 54%, 55%, 56%, 57%, 58%, 59%, or at least 60% identical to the lipase having amino acids 1-269 of SEQ ID NO: 2. In additional preferred embodiments, the percentage of identity is at least 61%, 62%, 63%, 64%, 65%, 66%, 67%, 68%, 69%, or at least 70%. In further preferred embodiments, the percentage of identity is at least 71%, 72%, 73%, 74%, 75%, 76%, 77%, 78%, 79%, or at least 80%. In additional preferred embodiments, the percentage of identity is at least 81%, 82%, 83%, 84%, 85%, 86%, 87%, 88%, 89%, or at least 90%. In additional more preferred embodiments, the percentage of identity is at least 91%, 92%, 93%, 94%, 95%, 96%, 97%, 98%, or at least 99%.

In another preferred embodiment, the parent lipase is at least 51% identical to the lipase having amino acids 1-269 of SEQ ID NO: 2. In additional preferred embodiments, it is at least 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% identical to the lipase having amino acids 1-269 of SEQ ID NO: 2.

Improved Properties

The present invention provides improved lipases for pharmaceutical use. Preferably, the enzymes for use according to the invention have an improved efficacy in vivo and/or in vitro; an improved activity; an improved stability; are stable against degradation by proteases; are stable in the presence of bile salts; and/or have a reduced allergenicity.

The lipases of the invention are preferably purified, more preferably to homogeneity, e.g., as described in Example 5 of WO 2006/136159. Purified lipase preparations may be analyzed by SDS-PAGE, and the lipase may be identified as the main protein band at 30-40 kDa. By densitometer scanning of coomassie-stained SDS-PAGE gels this band preferably constitutes 90-97% of the protein spectrum. The densitometer is, e.g., a GS-800 calibrated densitometer from BIO-RAD.

The lipase of the invention has an improved digestion performance as compared to a reference lipase, preferably an improved digestion performance in vitro.

The digestion performance is preferably determined using (I) a digestion model, (II) by determining stability at pH 3 in the presence of pepsin, and/or (III) by determining the activity at pH 5 in the presence of bile salts.

For each of the methods (I), (II), and (III), which are further discussed below, lipase variant N33Q+T231R+N233R of SEQ ID NO: 2 is a preferred example of a reference lipase (disclosed in WO 2006/136159). Other examples of reference lipases are: The lipase of SEQ ID NO: 1 (N33Q+T231R of SEQ ID NO: 2), and the lipase of SEQ ID NO: 2. A still further example of a reference lipase is the average of the lipase of amino acids +1 to +269 of SEQ ID NO: 1 and variant N33Q thereof.

The digestion model (I) represents a novel method of determining digestion performance, which comprises the following steps:

a) selecting a reference lipase;

b) mixing 100 parts per volume of a diet with 20 parts per volume of pepsin and 30 parts per volume of the lipase or the reference lipase, respectively;

c) adding i) 0 or ii) 10 parts per volume of buffer (0.8 M MES, 0.8 M sodium acetate, 0.8 M imidazole, pH 7.0), wherein step i) may be referred to as a gastric step of pH 3, and step ii) may be referred to as a gastric step of pH 5;

d) incubating for 1 hour at 37° C. with shaking;

e) adding 20 parts per volume of bile salts, as well as i) 25 or ii) 15 parts per volume of buffer (0.8 M MES, 0.8 M sodium acetate, 0.8 M imidazole, pH 7.0), wherein step i) corresponds to a gastric step of pH 3, and step ii) corresponds to a gastric step of pH 5;

f) incubating for 2 hours at 37° C. with agitation;

g) adding 50 parts per volume of 10% Triton-X100 in 1 M phosphoric acid;

h) determining the amount of free fatty acids;

i) fitting the dose response curves to the equation:

$$FFA=FFAmax*[E]/([E]+K)$$

where FFA is the amount of released free fatty acids, FFAmax is the maximal amount of free fatty acids that the lipases can liberate from the diet, [E] is the lipase concentration, and K is the lipase concentration that liberates half of FFAmax; and j) calculating an Improvement Factor (IF) as follows:

$$IF=K(ref)/K(lipase),$$

where K(ref) is the concentration of the reference lipase that liberates half of FFAmax and K(lipase) is the lipase concentration that liberates half of FFAmax.

The digestion performance may also be determined by the novel pepsin stability test at pH 3 referred to as (II) above, which method comprises the following steps:

i) selecting a reference lipase;

ii) mixing 5 parts per volume of the lipase or the reference lipase, respectively, with 5 parts per volume of a) a diluent containing 0.01% Triton-X100 and 10 mM NaCl, or b) a pepsin treatment solution containing 150 ug/mL pepsin, 4 mM $CaCl_2$, 0.01% Triton-X100, and 50 mM Citrate, pH 3.0, wherein a) is referred to as untreated sample, and b) is referred to as pepsin-treated sample;

iii) incubating the samples of step ii) for 3 hours at 20° C.;

iv) adding to each sample of step iii) 55 parts per volume of substrate containing 1 mM PNP-Palmitate, 1.2% Triton-X100, 4 mM $CaCl_2$, 100 mM TRIS, pH 8.0, together with a) 5 parts per volume of pepsin-treatment solution, or b) 5 parts per volume of diluent wherein a) refers to the untreated sample, and b) to the pepsin-treated sample;

v) following degradation of the substrate by reading $OD_{405}$ of the samples of iv) at intervals;

vi) collecting data from v) that falls in the linear range and calculating lipase activity for the pepsin-treated sample and the untreated sample, respectively, in mOD (milli OD) per hour;

vii) calculating % Residual lipase Activity (% RA) by dividing the lipase activity of the pepsin-treated sample with that of the untreated sample as they result from step vi), and multiplying the result by 100; and, if desired, viii) comparing % RA of the lipase with that of the reference lipase.

The digestion performance may also be determined by the novel bile salt activity test at pH 5 referred to as (III) above, which method comprises the following steps:

i) selecting a reference lipase;

ii) mixing 10 parts per volume of the lipase or the reference lipase, respectively, with 23 parts per volume of a) water, or b) 20 mM Bile salts, wherein a) is referred to as untreated sample, and b) is referred to as bile salts sample;

iii) adding, to each sample of ii), 200 parts per volume of substrate containing 1 mM PNP Oleate in 25 mM Succinate, 2 mM $CaCl_2$, 1.2% Triton-X100, pH 5.0, and mixing;

iv) immediately after step iii), removing, from each sample, 60 parts per volume of the resulting mixture and transferring four times 15 parts per volume thereof into four separate compartments;

v) adding, after 1, 2, 3, and 4 hours, 60 parts per volume of 100 mM TRIS, pH 8.0 to the respective compartment of the four compartments of iv), immediately reading OD 405, and, based on the linear range of the 1, 2, 3, and 4 hours readings, calculating the activity in mOD/hour;

vi) dividing, for the lipase as well as the reference lipase, the activity, obtained in step v), of the bile salts sample by the activity of the untreated sample, as also obtained in step v), to arrive at the bile salt stability ratios of the lipase and the reference lipase, respectively; and vii) dividing the bile salt stability ratio of the lipase by the bile salt stability ratio of the reference lipase, which resulting ratio may be defined as the improvement factor of the lipase.

Methods (I), (II) and (III) have been found to, surprisingly, identify improved lipases, of which a high proportion may also be improved in vivo.

Method (I)

The digestion model (referred to as (I) above) mimics digestion in monogastric animals (such as, e.g., pig and human beings) suffering from pancreatic exocrine insufficiency.

Triton X-100 ($C_{14}H_{22}O(C_2H_4O)_n$) (CAS No. 9002-93-1) is a nonionic surfactant which has a hydrophilic polyethylene oxide group (on average it has 9.5 ethylene oxide units, i.e., n=9-10) and a hydrocarbon lipophilic or hydrophobic group. The hydrocarbon group is a 4-(1,1,3,3-tetramethylbutyl)-phenyl group.

The term "parts per volume" preferably designates microliter which may be abbreviated ul, uL, µl, or µL.

In particular embodiments of the in vitro digestion model, (a) the pepsin concentration is 700 mg/ml; (b) the lipase and/or the reference lipase are analyzed in 4 different concentrations, each preferably in duplicate; and/or (c) the reactions take place in wells of a microtiter plate.

In additional particular embodiments of the in vitro digestion model, (d) the concentration of bile salts is 50 g/l; (e) the resulting pH after addition of bile salts and buffer in step e) is in the range of 5.7 to 6.0; and/or (f) Triton-X100 when added in step g) serves to stop the reaction.

In still further particular embodiments of the in vitro digestion model, (g) the amount of free fatty acids is determined after appropriate dilution, such as 125-250 times, preferably in 1% Triton-X100, and preferably determined using a NEFA C kit from Wako Chemicals, which is described in Example 3); (h) the dose response curve in step i) refers to the curve showing the response, viz. the amount of free fatty acids, as a function of lipase dose; and/or (i) assuming that FFAmax is identical for the lipases, i.e., for the reference lipase and the lipase(s) in question.

In additional particular embodiments of the in vitro digestion model, (j) Active Site Titration (AST, Example 6) is used to determine the lipase concentration; and/or (k) $A_{280}$ is used to determine the lipase concentration, preferably using the extinction coefficient 1.24 $A_{280}$/mg.

An improved lipase is defined as a lipase which has an improvement factor above 1.00. In particular embodiments, (i) the improvement factor is the average improvement factor; (ii) the improvement factor is the average improvement factor minus the standard deviation; and/or (iii) the improvement factor is above 1.0, or above 1. Average and standard deviation takes experimental variation into account and may be calculated as is known in the art, e.g. Standard deviation=(Sum(IF−Avg(IF))/(n−1))^0.5, where IF is the Improvement Factor, Avg(IF) is the average of the calculated Improvement Factors and n is the number of calculated Improvement Factors. The inverted V means exp.

The diet of the in vitro digestion model preferably contains between 250 and 400 g fat/kg, more preferably between 300 and 350 g fat/kg, most preferably between 313 and 340 g fat/kg. The content of carbohydrate and protein is not as relevant, but preferably it reflects usual and typical dietary requirements and recommendations, e.g. a carbohydrate content of 250-500 g/kg, and a protein content of between 10 and 200 g/kg. The diet may be selected from, e.g., Diet I (340 g fat/kg, 450 g carbohydrate/kg, 20 g protein/kg), or Diet II (313 g fat/kg, 358 g carbohydrate/kg, and 146 g protein/kg).

Diet I contains 247.2 parts per weight of cow's milk (1.5% fat), 29.9 parts per weight of olive oil, 87 parts per weight of Calshake (commercially available from Fresenius Kabi and having an energy content of 2077 kJ/g, a protein content of 4.3 g milk protein/100 g, and a fat content of 24.4 g fat/100 g), and 9.9 parts per weight of g Methocel (Food Grade, E5 Premium LV FG (E464); Dow). The ingredients are mixed, e.g. using an UltraTurrex (YellowLine DI 25 basic) for 2 minutes. Optionally, the diet is treated with 0.5 ug/ml of the SAVINASE 16.0 LEX protease (commercially available from Novozymes A/S, Krogshoejvej 36, DK-2880 Bagsvaerd, Denmark) at pH 8.0 for 4 hours at 50° C. to reduce viscosity. The protease is subsequently inactivated by reducing pH to 3 and incubating at 70° C. for 30 min, or 50° C. for 60 min. The term "parts by weight" preferably refers to gram (g).

Diet II contains, preferably consists of, 73 g/kg (wet weight) poultry meal (Altromin), 73 g/kg pea meal, 73 g/kg casein (precipitated under acidic conditions, from Altromin), 290 g/kg wheat flour, 290 g/kg potato starch, 125 g/kg lard, 76 g/kg vitamins, minerals and trace elements, and 375 g/kg cow's cream (33% fat).

Method (II)

The following are particular embodiments of the method of determining digestion performance by measuring the stability at pH 3 in the presence of pepsin, which method is referred to as (II) above:

(a) The lipases used in step ii) are culture supernatants, preferably prepared as follows: Single yeast colonies, such as colonies of *Saccharomyces cerevisiae* JG169 (see e.g., U.S. Pat. No. 7,217,433), capable of expressing the lipase are picked into 1 part per volume (e.g. 1 mL) of a suitable medium (e.g. the Seed Culture Medium of Example 8), and grown overnight at 30° C. and 250 rpm. Expression of the lipase is achieved by inoculating 0.020 parts per volume (e.g. 20 uL) of the resulting Seed Culture into 1 part per volume of a suitable medium (e.g. the Optimized Medium of Example 8) and cultivating at 30° C. and 250 rpm for 4-6 days. The cultivation may be performed in e.g. microtiter plates, e.g., 24-well plates, or in shake flasks. The lipase samples may be appropriately diluted, e.g. 25-fold, in diluent;

(b) The 3 hours of incubation of step iii) may be at room temperature;

(c) The reading of the $OD_{405}$ of step v) may e.g. take place 6 times; and e.g. as early as 15 minutes after substrate addition and as long as 18 hours after substrate addition;

(d) In step vi), lipase activity is calculated for the pepsin-treated sample and the untreated sample, respectively, in mOD (milli OD) per hour, and data from v) are collected that falls in the linear range;

(e) In step vii), calculating % Residual lipase Activity (% RA) by dividing the rate from step vi) of the pepsin-treated lipase by the rate of the untreated condition and multiplying the result by 100; and/or (f) In step v), OD 540 is also read and used to correct for background OD by subtracting the OD540 reading from the OD405 reading.

Method (III)

The following are particular embodiments of the method of determining digestion performance by measuring the activity at pH 5 in the presence of bile salts (referred to as (III) above):

(a) The lipases used in step ii) are purified; (b) the lipases are appropriately diluted, typically from between 25-fold to 200-fold in diluent (such as 0.01% Triton-X100, 10 mM NaCl), e.g. to approximately 8 micrograms/mL; (c) the concentration of the purified lipase samples is determined from the absorbance at 280 nm using the extinction coefficient 1.24 $A_{280}$/mg; (d) ODs between about 0.100 and 0.475 are in the linear range; and/or (e) the bile salts are Sigma B-8756 made up in distilled water to 20 mM.

In a further particular embodiment (f) in step vi) a ratio of the activity in the presence of bile salts at pH 5.0 is expressed as a percentage by calculating the average of all linear data obtained in step v) corrected for time and dilution for the "bile salts" activity divided by the average of all linear data corrected for time and dilution for the "no bile salts" activity.

(A) In a first particular embodiment, the lipase of the invention is selected from amongst lipases having the following substitutions, preferably sets of substitutions, as compared to the lipase of SEQ ID NO: 2:

N33Q+E87K+T231R+N233R;
N33Q+N94K+T231R+N233R;
N33Q+D96Y+T231R+N233R;
N33Q+K98I+T231R+N233R;
A30V+N33Q+K98I+T231R+N233R;
N33Q+E87K+D96E+T231R+N233R;
N26I+N33Q+T231R+N233R;
A30T+N33Q+T231R+N233R;
N33Q+G91V+T231R+N233R;
N33Q+G91A+T231R+N233R;
N33Q+G91V+L97M+T231R+N233R;
N33Q+K98I+T231R+N233R;
N33Q+L69I+G91E+T231R+N233R;
P29T+N33Q+T231R+N233R;
N33Q+G91V+T231R+N233R;
N33Q+K98I+T231R+N233R;
N33Q+G91E+T231R+N233R; and
N33Q+N94K+T231R+N233R.

In a second particular embodiment, the lipase of the invention is selected from amongst lipases having the following substitutions, preferably sets of substitutions, as compared to the lipase of SEQ ID NO: 2:

N33Q+K98I+T231R+N233R:
A30V+N33Q+K98I+T231R+N233R;
N33Q+G91V+T231R+N233R;
N33Q+G91A+T231R+N233R;
N33Q+G91V+L97M+T231R+N233R;
N33Q+K98I+T231R+N233R;
N33Q+L69I+G91E+T231R+N233R;
P29T+N33Q+T231R+N233R;
N33Q+G91V+T231R+N233R;
N33Q+K98I+T231R+N233R;
N33Q+G91E+T231R+N233R; and
N33Q+N94K+T231R+N233R.

In a third particular embodiment, the lipase of the invention is selected from amongst lipases having the following substitutions, preferably sets of substitutions, as compared to the lipase of SEQ ID NO: 2:

N33Q+K98I+T231R+N233R;
N33Q+G91V+T231R+N233R;
N33Q+G91A+T231R+N233R;
N33Q+G91V+L97M+T231R+N233R;
N33Q+K98I+T231R+N233R;
N33Q+L69I+G91E+T231R+N233R;
N33Q+G91E+T231R+N233R; and
N33Q+N94K+T231R+N233R.

In a fourth particular embodiment, the lipase of the invention is selected from amongst lipases having the following substitutions, preferably sets of substitutions, as compared to the lipase of SEQ ID NO: 2:

N33Q+G91V+T231R+N233R;
N33Q+G91A+T231R+N233R;
N33Q+K98I+T231R+N233R; and
N33Q+G91E+T231R+N233R.

Variants of the lipase of amino acids 1-269 of SEQ ID NO: 2 with the above-listed substitutions (each of the four particular embodiments) all have an improved in vitro digestion performance, i.e., an improvement factor (IF) of at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 3 is preferably used. A preferred diet is diet II. Active Site Titration (AST, Example 6) and/or $A_{280}$ may be used to determine the lipase concentration, preferably using the extinction coefficient 1.24 $A_{280}$/mg.

(B) In another first particular embodiment, the lipase of the invention is selected from amongst lipases having the following substitutions, preferably sets of substitutions, as compared to the lipase of SEQ ID NO: 2:

D27V+N33Q+V60S+D96W+T231R+N233R+Q249R;
D27V+N33Q+V60S+T231R+N233R+Q249R;
Q9H+N33Q+D102E+T231R+N233R;
N33Q+D111E+T231R+N233R;
N33Q+D122E+T231R+N233R;
D27R+N33Q+G91N+N94R+D111A+S216P+L227G+T231R+N233R+P256T;
N33Q+T231R+N233R+P256T;
D27R+N33Q+G91A+L93*+N94*+F95*+D96*+D111A+T231R+N233R+P256T;
N11R+N33Q+T231R+N233R;
N33Q+N39H+T231R+N233R;
N33Q+P229R+T231R+N233R;
D27R+N33Q+G91N+N94R+D111A+G163K+S216P+L227G+T231R+N233R+P256T;

N33Q+G91T+G163K+T231R+N233R;
D27R+N33Q+G91A+D96E+L97Q+D111A+S216P+L227G+T231R+N233R+P256T;
D27R+N33Q+G91A+D96E+L97Q+D111A+S216P+T231R+N233R+P256T;
D27R+N33Q+G91A+D96E+D111A+T231R+N233R+D254G+P256T;
D27R+N33Q+G91A+N94S+D111A+T231R+N233R+P256T;
N33Q+N200S+T231R+N233R;
N33Q+N39S+T231R+N233R;
N33Q+E210R+T231R+N233R;
N33Q+N39H+T231R+N233R+D254R;
N33Q+T231R+N233R+D254R;
N33Q+N94R+T231R+N233R;
N33Q+D96R+T231R+N233R;
D27N+N33Q+T231R+N233R;
D27N+N33Q+E56R+T231R+N233R;
N33Q+L227F+T231R+N233R;
N33Q+N73Y+G225P+T231R+N233R;
N33Q+G225P+T231R+N233R;
N33Q+T231R+N233R+D254S;
N33Q+D96G+T231R+N233R;
N33Q+D96N+T231R+N233R+D254S;
N33Q+T231R+N233R+D254G;
N33Q+D130H+T231R+N233R;
N33Q+E87A+T231R+N233R;
N33Q+T231R+N233R+E239D;
N33Q+D111A+T231R+N233R+D254G;
N33Q+E210V+T231R+N233R+D254S;
N11R+N33Q+E210V+T231R+N233R+D254S;
N33Q+G91T+G163K+T231R+N233R+D254G;
N33Q+G91T+G163K+T231R+N233R+D254S;
N11R+N33Q+G91T+G163K+T231R+N233R+D254S;
Q4R+D27R+N33Q+G91T+N94S+D111A+S216P+L227G+T231R+N233R+P256T;
N33Q+G91T+N94S+D111A+V176I+T231R+N233R;
Q4R+D27R+N33Q+G91T+N94S+D111A+E210D+S216P+L227G+T231R+N233R+P256T;
Q4R+D27Q+N33Q+G91T+N94S+D111A+S216P+L227G+T231R+N233R+P256T;
N33Q+G91T+N94S+D111A+T231R+N233R+P256T;
N33Q+G177A+T231R+N233R;
N33Q+T231R+N233R+G246A;
D27N+N33Q+G91T+G163K+T231R+N233R+D254S;
D27Q+N33Q+G91T+G163K+E219D+T231R+N233R; and
N33Q+G91T+E219D+T231R+N233R.

In another second particular embodiment, the lipase of the invention is selected from amongst lipases having the following substitutions, preferably sets of substitutions, as compared to the lipase of SEQ ID NO: 2:

D27V+N33Q+V60S+D96W+T231R+N233R+Q249R;
D27R+N33Q+G91A+D96E+L97Q+D111A+S216P+T231R+N233R+P256T;
D27R+N33Q+G91A+D96E+D111A+T231R+N233R+D254G+P256T;
N33Q+N39S+T231R+N233R;
N33Q+N94R+T231R+N233R;
N33Q+T231R+N233R+D254S;
N33Q+D96N+T231R+N233R+D254S;
N33Q+E210V+T231R+N233R+D254S;
N11R+N33Q+E210V+T231R+N233R+D254S;
N33Q+G91T+G163K+T231R+N233R+D254G;
N33Q+G91T+G163K+T231R+N233R+D254S;
N11R+N33Q+G91T+G163K+T231R+N233R+D254S;
N33Q+G91T+N94S+D111A+V176I+T231R+N233R;
N33Q+G91T+N94S+D111A+T231R+N233R+P256T; and
D27N+N33Q+G91T+G163K+T231R+N233R+D254S.

In another third particular embodiment, the lipase of the invention is selected from amongst lipases having the following substitutions, preferably sets of substitutions, as compared to the lipase of SEQ ID NO: 2:
N33Q+D96N+T231R+N233R+D254S;
N33Q+E210V+T231R+N233R+D254S;
N11R+N33Q+E210V+T231R+N233R+D254S;
N33Q+G91T+G163K+T231R+N233R+D254S;
N11R+N33Q+G91T+G163K+T231R+N233R+D254S; and
N33Q+G91T+N94S+D111A+V176I+T231R+N233R.

In another fourth particular embodiment, the lipase of the invention is selected from amongst lipases having the following substitutions, preferably sets of substitutions, as compared to the lipase of SEQ ID NO: 2:
N33Q+G91T+N94S+D111A+V176I+T231R+N233R.

Variants of the lipase of amino acids 1-269 of SEQ ID NO: 2 with the above-listed substitutions (each of the four other particular embodiments) all have an improved in vitro digestion performance, i.e., an improvement factor (IF), preferably average IF minus standard deviation, of above 1.00, or of at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 3 is preferably used. A preferred diet is diet I. Active Site Titration (AST, Example 6) is preferably be used to determine the lipase concentration.

(C) In a still further first particular embodiment, the lipase of the invention is selected from amongst lipases having the following substitutions, preferably sets of substitutions, as compared to the lipase of SEQ ID NO: 2:
N33Q+E219D+T231R+N233R;
N33Q+W117L+T231R+N233R;
D27Q+N33Q+T231R+N233R;
N33Q+G91T+T231R+N233R;
D27S+N33Q+G91A+D96E+L97Q+D111A+S216P+T231R+N233R+P256T;
D27R+N33Q+G91N+N94R+D111A+T231R+N233R+P256T;
D27R+N33Q+G91T+N94S+D111A+S216P+L227G+T231R+N233R+P256T;
Q4R+N33Q+T231R+N233R;
N33Q+T231R+N233R+Q249R;
N33Q+D96W+T231R+N233R; and
N33Q+G91N+T231R+N233R.

In a still further second particular embodiment, the lipase of the invention is selected from amongst lipases having the following substitutions, preferably sets of substitutions, as compared to the lipase of SEQ ID NO: 2:
N33Q+E219D+T231R+N233R;
D27Q+N33Q+T231R+N233R;
N33Q+G91T+T231R+N233R; and
D27R+N33Q+G91T+N94S+D111A+S216P+L227G+T231R+N233R+P256T.

In a still further third particular embodiment, the lipase of the invention is selected from amongst lipases having the following substitutions, preferably sets of substitutions, as compared to the lipase of SEQ ID NO: 2:
N33Q+E219D+T231R+N233R; and
N33Q+G91T+T231R+N233R.

Variants of the lipase of amino acids 1-269 of SEQ ID NO: 2 with the above-listed substitutions (each of the three still further particular embodiments) all have an improved in vitro digestion performance, i.e., an improvement factor (IF), preferably average IF minus standard deviation, of above 1.00, or at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 3 is preferably used. A preferred diet is diet II. Active Site Titration (AST, Example 6) is preferably used to determine the lipase concentration.

(D) In a first particular embodiment, the lipase of the invention is selected from amongst lipases having the following substitutions, preferably sets of substitutions, as compared to the lipase of SEQ ID NO: 2:
N33Q+D167E+T231R+N233R;
N33Q+E87A+T231R+N233R;
N33Q+E210V+T231R+N233R;
N33Q+E56K+T231R+N233R;
N33Q+T231R+N233R+D254G;
N33Q+D96S+T231R+N233R;
N33Q+D122N+T231R+N233R;
N26A+N33Q+T231R+N233R;
N33Q+N162T+T231R+N233R;
N33Q+A150V+N162G+T231R+N233R;
N33Q+T231R+N233R+G240L;
N33Q+E210V+T231R+N233R+D254S;
N11R+N33Q+E210V+T231R+N233R+D254S;
N33Q+G91T+N94S+D111A+V176I+T231R+N233R;
Q4R+D27R+N33Q+G91T+N94S+D111A+E210D+S216P+L227G+T231R+N233R+P256T;
N33Q+G91T+E219D+T231R+N233R;
N33Q+G163R+T231R+N233R;
N33Q+G163N+T231R+N233R;
N33Q+G163C+T231R+N233R;
N33Q+G163Q+T231R+N233R;
N33Q+G163E+T231R+N233R;
N33Q+G163H+T231R+N233R;
N33Q+G163I+T231R+N233R;
N33Q+G91K+T231R+N233R;
N33Q+G91M+T231R+N233R;
N33Q+G91F+T231R+N233R;
N33Q+G91S+T231R+N233R;
N33Q+G91W+T231R+N233R;
N33Q+G91Y+T231R+N233R;
N33Q+G163Y+T231R+N233R;
N33Q+G163V+T231R+N233R;
N33Q+G91C+T231R+N233R;
N33Q+G91Y+Q126L+T231R+N233R;
N33Q+G91M+G161E+T231R+N233R;
N33Q+V128A+T231R+N233R;
N33Q+V128A+T231R+N233R;
N33Q+G163E+T231R+N233R;
N33Q+G163V+L185M+T231R+N233R;
N33Q+G38A+T231R+N233R;
N33Q+G163A+T231R+N233R;
N33Q+G91T+N94S+D111A+T231R+N233R;
N33Q+G163M+T231R+N233R;
N33Q+G91V+T231R+N233R;
N33Q+D111A+T231R+N233R+Q249R;
D27R+N33Q+G91A+D96E+L97Q+D111A+T231R+N233R+D254G+P256T;
N33Q+G91T+N94R+T231R+N233R+D254S;
N33Q+G91T+N94R+D111A+W117L+T231R+N233R;
N33Q+W117L+T231R+N233R+D254S;
N33Q+T231R+N233R+P256T;
N33Q+T231R+N233R+D242E;
N33Q+E87R+T231R+N233R;
N33Q+E56R+T231R+N233R;
N33Q+N162G+T231R+N233R;
N33Q+G91L+T231R+N233R;
N33Q+E87H+T231R+N233R;
N33Q+D96N+T231R+N233R+Q249R;

N33Q+G91T+N94R+T231R+N233R+D254S;
N33Q+L227F+T231R+N233R+D254S;
N33Q+G163A+T231R+N233R;
D27R+N33Q+G91T+D96E+D111A+T231R+N233R+D254S+P256T;
N33Q+G91T+N94R+T231R+N233R;
N33Q+T231R+N233R+D254A;
N33Q+T231R+N233R+D254N;
N33Q+T231R+N233R+D254L;
N33Q+T231R+N233R+D254K;
N33Q+T231R+N233R+D254M;
D27V+N33Q+V60S+G91T+D96W+T231R+N233R+Q249R;
N33Q+D96N+L227G+T231R+N233R+Q249R;
D27R+N33Q+L227G+T231R+N233R;
D27R+N33Q+L227G+T231R+N233R+Q249R;
N33Q+E219D+L227G+T231R+N233R+Q249R;
D27Q+N33Q+L227G+T231R+N233R+Q249R;
N33Q+W117L+L227G+T231R+N233R+Q249R;
D5E+N33Q+W117L+L227G+T231R+N233R+Q249R;
D27Q+N33Q+E219D+L227G+T231R+N233R+Q249R;
N33Q+D96E+E219D+L227G+T231R+N233R+Q249R;
D27R+N33Q+E56K+G91N+N94R+D111A+S216P+L227G+T231R+N233R+D256T;
D27R+N33Q+E56Q+D57N+G91N+N94R+D111A+S216P+L227G+T231R+P256T;
D27R+N33Q+E56Q+D57N+G91N+N94R+D111S+S216P+L227G+T231R+N233R+P256T;
D27R+N33Q+E56S+G91N+N94R+D111A+S216P+L227G+T231R+N233R+D254S+P256T;
D27R+N33Q+G91N+N94R+D111A+S216P+L227G+T231R+N233R+D254S+P256T;
D27R+N33Q+G91N+N94R+D111A+S216P+L227G+T231R+N233R+D254S+P256T;
D27R+N33Q+G91N+N94R+D111S+A155V+S216P+L227G+T231R+N233R+D254S+P256T;
D27R+N33Q+G91N+N94R+D111S+S216P+L227G+T231R+N233R+D254S+P256T;
N33Q+D111A+T231R+N233R+D254S;
N33Q+D111A+W117L+T231R+N233R+D254S;
N33Q+T231R+N233R+P256N;
N33Q+T231R+N233R+P256G;
N33Q+T231R+N233R+P256H;
N33Q+T231R+N233R+P256M;
N33Q+T231R+N233R+P256W;
N33Q+T231R+N233R+P256Y;
N33Q+T231R+N233R+P256F;
N33Q+T231R+N233R+P256V;
N33Q+G91M+G163W+T231R+N233R;
N33Q+G91M+G163T+T231R+N233R;
N33Q+G91M+G163D+T231R+N233R;
N33Q+G91K+G163W+T231R+N233R;
N33Q+G91T+G163W+T231R+N233R;
N33Q+V176N+T231R+N233R;
N33Q+V176D+T231R+N233R;
N33Q+W117F+T231R+N233R;
N33Q+V176I+T231R+N233R;
N33Q+D111N+T231R+N233R;
N33Q+D111N+G225P+T231R+N233R;
N33Q+D111N+S216P+T231R+N233R;
D27R+N33Q+G91T+N94R+D111A+S216P+L227G+T231R+N233R;
N33Q+G91M+G163P+T231R+N233R;
N33Q+G91T+G163A+T231R+N233R;
N33Q+W117D+T231R+N233R;
N33Q+W117H+T231R+N233R;
N33Q+W117C+T231R+N233R;
N33Q+W117C+T231R+N233R;
N33Q+W117K+T231R+N233R;
N33Q+W117V+T231R+N233R;
N11S+N33Q+T231R+N233R;
N33Q+W117E+V176K+T231R+N233R;
N33Q+W117G+T231R+N233R;
N33Q+W117P+T231R+N233R;
N33Q+W117S+T231R+N233R;
N33Q+W117T+T231R+N233R;
N33Q+W117I+T231R+N233R;
D27R+N33Q+L227G+T231R+N233R+Q249R+D254S;
N33Q+V176M+T231R+N233R;
N33Q+V176H+T231R+N233R;
N33Q+V176A+T231R+N233R;
D27V+N33Q+L227F+T231R+N233R+Q249R;
N33Q+W117Y+T231R+N233R;
N33Q+W117Y+V176D+T231R+N233R;
D27R+N33Q+P136H+L227G+T231R+N233R+Q249R+D254S;
N11R+N33Q+T231R+N233R+T244S;
N33Q+G91T+D96N+D111A+V176I+T231R+N233R+D254S;
N33Q+G91T+N94S+D111A+V176I+T231R+N233R+D254S;
N33Q+G161A+T231R+N233R;
N33Q+G38I+G177A+T231R+N233R;
N33Q+N101Q+T231R+N233R;
N33Q+N94Q+T231R+N233R;
N11Q+N33Q+T231R+N233R;
N8Q+N33Q+T231R+N233R;
N33Q+T231R+N233R+N251Q;
N33Q+N200Q+T231R+N233R;
N33Q+G177A+T231R+N233R;
N33Q+N73Q+T231R+N233R;
N33Q+186L+T231R+N233R;
N33Q+K98I+G163K+T231R+N233R;
D27R+N33Q+G91T+D96E+D111A+G163K+T231R+N233R+D254S+P256T;
D27R+N33Q+G91T+D96E+D111A+G163A+T231R+N233R+D254S+P256T;
D27R+N33Q+S216P+L227G+T231R+N233R+Q249R;
N33Q+K98I+G163K+N200Q+T231R+N233R+N251S;
N33Q+G38S+G163K+T231R+N233R;
N33Q G38Y T231R N233R;
D27R+N33Q+G91T+N94R+D111A+S216P+L227G+T231R+N233R+P256T;
D27R+N33Q+G91T+N94R+D111A+S216P+L227G+T231R+N233R+P256T;
N33Q+G38N+N73Q+T231R+N233R;
N33Q+G38D+R84E+T231R+N233R;
N33Q+G38Q+T231R+N233R;
N33Q+G38I+T231R+N233R;
N33Q+G38K+T231R+N233R;
N33Q+G38F+T231R+N233R;
N33Q+G38H+N200Q+T231R+N233R+N251S;
N33Q+G38L+T231R+N233R;
N33Q+G38P+T231R+N233R;
N33Q+G38T+T231R+N233R;
N11R+N33Q+G91T+W117I+G163K+T231R+N233R+D254S;
D27R+N33Q+G38A+G91T+D96E+D111A+G163K+T231R+N233R+D254S+P256T;
N11R+N33Q+G91T+W117I+G163K+T231R+N233R+D254S;
D27R+N33Q+G38A+G91T+D96E+D111A+G163A+T231R+N233R+D254S+P256T;

D27R+N33Q+V176Q+L227G+T231R+N233R+Q249R+D254S;
N33Q+W117I+V176Q+T231R+N233R+P256A;
N33Q+G38A+G163A+T231R+N233R+P256A;
N33Q+W117I+V176Q+T231R+N233R;
N33Q+G177A+T231R+N233R+G246A;
E1N N33Q T231R N233R;
N33Q G38H T231R N233R;
N11R+N33Q+G91T+G163K+V176Q+T231R+N233R+D254S;
N33Q+K98I+T231R+N233R;
D27R+N33Q+W117I+V176Q+L227G+T231R+N233R+Q249R+D254S;
N11R+N33Q+G38A+G91T+G163K+T231R+N233R+D254S;
N33Q+G163W+T231R+N233R;
N33Q+G38A+G163A+T231R+N233R;
D27R+N33Q+G91T+D96E+L97Q+D111A+T231R+N233R+D254S+P256T;
N33Q+T231R+N233R+D254Q;
N11R+N33Q+G91T+S115L+G163K+T231R+N233R+D254S;
N11R+N33Q+G91T+G163K+V176W+T231R+N233R+D254S;
N33Q+G163D+T231R+N233R;
N33Q+G163D+T231R+N233R;
N33Q+G163P+T231R+N233R;
E1D+N33Q+G91T+N94R+D111A+W117L+T231R+N233R+D254S;
N33Q+G91T+N94R+D111A+W117L+V176W+T231R+N233R;
Q4P+D27R+N33Q+G91N+N94R+D111A+L206F+S216P+L227G+T231R+N233R+P256T;
D27R+N33Q+T37K+N71I+G91N+N94R+K98I+D111A+S216P+L227G+T231R+N233R+P256T;
D27R+N33Q+E43K+K46M+I90V+G91N+N94R+D111A+T114I+S216P+L227G+T231R+N233R+P256T;
N33Q+W117S+T231R+N233R;
N33Q+G61R+V63R+G156R+V176W+T231R+N233R+P256I;
N33Q+D96N+G156R+V176W+T231R+N233R;
N33Q+G156R+V176W+T231R+N233R+Q249R;
N33Q+G91T+N94S+D111A+G163T+V176W+T231R+N233R;
N33Q+G91T+N94S+D111A+S115L+G163T+V176I+T231R+N233R;
N11R+D27R+N33Q+E56Q+D57N+G91N+N94R+D111S+G163T+S216P+L227G+T231R+N233R+D254S+P256T;
D27R+N33Q+E56Q+D57N+G91N+N94R+D111S+G163T+S216P+L227G+T231R+N233R+D254S+P256T;
N11R+D27R+N33Q+E56Q+D57N+G91N+N94R+D111S+S216P+L227G+T231R+N233R+D254S+P256T;
D27R+N33Q+E56Q+D57N+G91N+N94R+D111S+S216P+L227G+T231R+N233R+D242E+D254S+P256T;
D27R+N33Q+G38A+E56Q+D57N+G91N+N94R+D111S+S216P+L227G+T231R+N233R+D254S+P256T;
Q4R+D27Q+N33Q+G91T+N94S+E99D+D111A+E210D+S216P+L227G+T231R+N233R+P256L;
N33Q+G38A+G91T+G163A+T231R+N233R+D254S;
N33Q+G38A+G163A+T231R+N233R+D254I;
N11R+N33Q+I90L+G163L+T231R+N233R;
N11R+N33Q+I90L+G163L+T231R+N233R+D254S;
N11R+N33Q+E56Q+G91T+G163K+V176Q+T231R+N233R+D254S;
N11R+D27R+N33Q+G91T+D96E+D111A+G163K+T231R+N233R+D254S+P256T;
N11R+N33Q+G38A+G91T+G12A+G163A+T231R+N233R+D254S;
N11R+N33Q+G91T+G163K+E210D+T231R+N233R+D254S;
N11R+N33Q+G91T+G163K+T231R+N233R+D254I;
N11R+N33Q+G91T+G163K+V176T+T231R+N233R+D254S;
N11R+N33Q+G91T+G163P+T231R+N233R+D254S;
N11R+N33Q+G91M+G163T+T231R+N233R+D254S;
N11R+N33Q+G38A+G91T+G163K+V176D+T231R+N233R+D254S;
N33Q+E56Q+G156R+V176W+T231R+N233R;
E1D+N33Q+G38A+G91T+N94R+D111A+W117L+V176W+T231R+N233R;
N33Q+G163K+G177A+T231R+N233R+G246A;
N11R+N33Q+E56Q+G91T+G163K+T231R+N233R+D254S;
N11R+N33Q+190L+G163K+T231R+N233R+D254S;
D27R+N33Q+E56Q+D57N+G91N+N94R+D111S+S216P+L227G+T231R+N233R+Q249R+D254S+P256T;
D27R+N33Q+E56Q+D57N+G91N+N94R+D111S+S216P+E219D+L227G+T231R+N233R+D254S+P256T;
N11R+N33Q+I90L+G91T+N94S+D96E+G163K+T231R+N233R+D254S;
N11R+N33Q+G91T+G163K+V176I+T231R+N233R+D254S;
N11R+N33Q+G91T+G163K+V176Q+T231R+N233R+D254S;
N11R+N33Q+G91T+G163A+V176T+T231R+N233R+D254S;
N11R+N33Q+G91T+G163L+V176I+T231R+N233R+D254S;
N11R+N33Q+G91T+G163L+V176T+T231R+N233R+D254S;
N11R+N33Q+G91T+G163L+T231R+N233R+D254S;
N11R+N33Q+G91T+G163P+T231R+N233R+D254S;
N11R+N33Q+G91T+G163P+V176I+T231R+N233R+D254S;
N11R+N33Q+G91T+G163L+T231R+N233R+D254S+P256N;
D27R+N33Q+E56Q+D57N+G91N+N94R+D111S+G163T+S216P+L227G+T231R+N233R+Q249R+D254S+P256T;
Q4R+D27Q+N33Q+G91T+N94S+E99D+D111A+G163A+E210V+S216P+L227G+T231R+N233R+P256L;
Q4R+D27Q+N33Q+G91T+N94S+E99D+D111A+V176I+E210V+S216P+L227G+T231R+N233R+P256L;
N33Q+E210Y+T231R+N233R+D254Y+I255F;
N33Q+L93F+D102Y+T231R+N233R;
D27R+N33Q+L227G+T231R+N233R+Q249R+D254S;
N11S+N33Q+T231R+N233R;
N11R+N33Q+T231R+N233R:
N33Q+G38A+G91T+G163K+T231R+N233R+D254S;
N33Q+W117Y+V176T+T231R+N233R;
N8L+N11R+N33Q+G91T+G163K+T231R+N233R+D254S;
E1N+N33Q+G38A+G91T+G163P+V176F+T231R+N233R;
N11R+N33Q+G38A+G91T+G163P+V176G+T231R+N233R+D254S;
N11R+N33Q+G91T+G163K+T231R+N233R+D254A+P256F;
N11R+N33Q+G91T+G163K+T231R+N233R+P256F;
N11R+N33Q+G91T+G163K+T231R+N233R+D254S+P256F;
N11R+N33Q+G38A+G91T+G156R+G163K+V176T+T231R+N233R+D254S;

N33Q+G91K+D96S+G163T+T231R+N233R+Q249R;
N11R+N33Q+G91T+G163N+T231R+N233R+D254S;
N11R+N33Q+G91T+G163T+T231R+N233R+D254S;
N11R+N33Q+G91T+G163W+T231R+N233R+D254S:
N11R+N33Q+G91K+G163K+T231R+N233R+D254S;
N11R+G23E+N33Q+G91T+G163K+T231R+N233R+D254S;
N11R+N33Q+G91T+V141E+G163K+T231R+N233R+D254S;
N11R+N33Q+L52R+G91T+G163K+T231R+N233R+D254S;
N11R+N33Q+G91T+V141L+G163K+T231R+N233R+D254S;
N11R+N33Q+T37K+G91T+G163K+T231R+N233R+D254S;
N11R+N33Q+A68V+G91T+G163K+T231R+N233R+D254S;
N11R+N33Q+G91T+G163A+V176I+T231R+N233R+D254S;
N11R+N33Q+T37M+G91T+G163P+V176T+T231R+N233R+D254S;
N11R+N33Q+G91T+G163L+T231R+N233R+D254S;
N11R+N33Q+G91T+G163K+T231R+N233R+D254S+P256I;
N33Q+G38S+G156R+G163K+V176W+T231R+N233R;
N11R+D27R+N33Q+E56Q+D57N+G91N+N94R+D111S+G163K+S216P+L227G+T231R+N233R+D254S+P256T;
N11R+N33Q+G38A+G91T+G163P+V176G+T231R+N233R+D254S;
N11R+N33Q+G38A+G91T+G163Q+V176G+T231R+N233R+D254S;
N11R+N33Q+G38A+G91T+G163T+V176G+T231R+N233R+D254S;
N11R+N33Q+G38A+G91T+N94R+G163P+V176G+T231R+N233R+D254S;
E1*+N11R+N33Q+G38A+G91N+N94R+G163P+V176G+T231R+N233R+D254S;
E1N+N11R+N33Q+G38A+G91T+G163P+V176F+T231R+N233R;
E1N+F10L+N11R+N33Q+G38A+G91T+G163P+V176F+T231R+N233R;
E1N+N33Q+G38A+G91T+G163P+V176F+T231R+N233R+D254S;
E1N+N33Q+G38A+G91T+D111A+G163P+V176F+T231R+N233R;
E1N+N33Q+G38A+G91T+G163P+V176F+L227F+T231R+N233R;
E1N+N11R+N33Q+G38A+G91T+D111A+G163P+V176F+T231R+N233R;
E1N+N33Q+G38A+G91T+G163P+V176F+L227F+T231R+N233R+D254S;
E1N+N33Q+G38A+G91T+G163P+V176F+T231R+N233R+D254S+I255A+P256Q;
E1N+N11R+N33Q+G38A+G91T+D111A+G163P+V176F+T231R+N233R+D254S;
N33Q+G156R+V176W+T231R+N233R+P256I;
N33Q+G91T+N94S+D111A+G156R+G163T+V176W+T231R+N233R;
N33Q+G91T+N94S+D111A+G156R+G163T+V176I+T231R+N233R;
N11R+N33Q+G38A+G91T+D102G+S115L+G163K+T231R+N233R+D254S+P256T;
N11R+N33Q+G38A+G91T+S115L+G163K+T231R+N233R+D254S+P256T;
E1N+N11R+N33Q+G91T+G163A+T231R+N233R+G246A+D254S;
N11R+D27R+N33Q+D57G+G91T+D96E+D111A+G163K+T231R+N233R+D254S+P256T;
N33Q+D96N+G156R+V176W+T231R+N233R+Q249R;
N33Q+I86F+L93F+D102Y+E210Y+L227F+T231R+N233R+D254Y+I255F+L269F;
N33Q+I86F+L93F+D102Y+E210Y+L227F+T231R+N233R+D254Y+I255F:
N11C+N33Q+G91T+G163K+T231R+N233R+D254S;
N11L+N33Q+G91T+G163K+T231R+N233R+D254S;
N11H+N33Q+G91T+G163K+T231R+N233R+D254S;
N11D+N33Q+G91T+G163K+T231R+N233R+D254S;
N11R+N33Q+G91T+D96W+G163K+T231R+N233R+D254S;
D27R+N33Q+G91T+D96E+L97Q+D111A+G163K+T231R+N233R+D254S+P256T;
N11P+N33Q+G91T+G163K+T231R+N233R+D254S;
Q4R+D27N+N33Q+G38A+G91T+N94S+E99D+D111A+V176I+E210V+S216P+L227G+T231R+N233R+P256L;
N11R+N33Q+E56Q+G163K+T231R+N233R+D254S;
N11R+N33Q+G91T+G163A+T231R+N233R+D254S;
N11R+N33Q+G91T+G163P+T231R+N233R+D254S; and
N11R+N33Q+G91T+G163K+L227G+P229R+T231R+N233R+D254S.

In a second particular embodiment, the lipase of the invention is selected from amongst lipases having the following substitutions, preferably sets of substitutions, as compared to the lipase of SEQ ID NO: 2:

N33Q+E87A+T231R+N233R;
N33Q+E210V+T231R+N233R;
N33Q+E56K+T231R+N233R;
N33Q+T231R+N233R+D254G;
N33Q+D96S+T231R+N233R;
N33Q+N162T+T231R+N233R;
N33Q+T231R+N233R+G240L;
N33Q+E210V+T231R+N233R+D254S;
N11R+N33Q+E210V+T231R+N233R+D254S;
N33Q+G163N+T231R+N233R;
N33Q+G163Q+T231R+N233R;
N33Q+G163E+T231R+N233R;
N33Q+G91M+T231R+N233R;
N33Q+G91F+T231R+N233R;
N33Q+G163Y+T231R+N233R;
N33Q+G91Y+Q126L+T231R+N233R;
N33Q+V128A+T231R+N233R;
N33Q+G38A+T231R+N233R;
N33Q+G163M+T231R+N233R;
N33Q+D111A+T231R+N233R+Q249R;
D27R+N33Q+G91A+D96E+L97Q+D111A+T231R+N233R+D254G+P256T;
N33Q+G91T+N94R+T231R+N233R+D254S;
N33Q+G91T+N94R+D111A+W117L+T231R+N233R;
N33Q+W117L+T231R+N233R+D254S;
N33Q+T231R+N233R+P256T;
N33Q+T231R+N233R+D242E;
N33Q+E87R+T231R+N233R;
N33Q+E56R+T231R+N233R;
N33Q+N162G+T231R+N233R;
N33Q+G91L+T231R+N233R;
N33Q+E87H+T231R+N233R;
N33Q+D96N+T231R+N233R+Q249R;
N33Q+G91T+N94R+T231R+N233R+D254S;
N33Q+L227F+T231R+N233R+D254S;
N33Q+G91T+N94R+T231R+N233R;
N33Q+T231R+N233R+D254L;
N33Q+T231R+N233R+D254K;
N33Q+T231R+N233R+D254M;

D27V+N33Q+V60S+G91T+D96W+T231R+N233R+Q249R;
N33Q+D96N+L227G+T231R+N233R+Q249R;
N33Q+E219D+L227G+T231R+N233R+Q249R;
D27Q+N33Q+E219D+L227G+T231R+N233R+Q249R;
N33Q+D96E+E219D+L227G+T231R+N233R+Q249R;
D27R+N33Q+E56K+G91N+N94R+D111A+S216P+L227G+T231R+N233R+P256T;
D27R+N33Q+E56Q+D57N+G91N+N94R+D111A+S216P+L227G+T231R+N233R+P256T;
D27R+N33Q+G91N+N94R+D111A+S216P+L227G+T231R+N233R+D254S+P256T;
D27R+N33Q+G91N+N94R+D111A+S216P+L227G+T231R+N233R+D254S+P256T;
D27R+N33Q+G91N+N94R+D111S+S216P+L227G+T231R+N233R+D254S+P256T;
N33Q+D111A+T231R+N233R+D254S;
N33Q+T231R+N233R+P256N;
N33Q+T231R+N233R+P256G;
N33Q+T231R+N233R+P256M;
N33Q+T231R+N233R+P256W;
N33Q+W117F+T231R+N233R;
N33Q+D111N+G225P+T231R+N233R;
D27R+N33Q+G91T+N94R+D111A+S216P+L227G+T231R+N233R;
N33Q+W117C+T231R+N233R;
N33Q+W117C+T231R+N233R;
N33Q+W117K+T231R+N233R;
N11S+N33Q+T231R+N233R;
N33Q+W117G+T231R+N233R;
N33Q+W117P+T231R+N233R;
N33Q+W117S+T231R+N233R;
N33Q+W 17T+T231R+N233R;
D27R+N33Q+L227G+T231R+N233R+Q249R+D254S;
N11R+N33Q+T231R+N233R+T244S;
N33Q+G91T+D96N+D111A+V176I+T231R+N233R+D254S;
N33Q+G91T+N94S+D111A+V176I+T231R+N233R+D254S;
N33Q+G38I+G177A+T231R+N233R;
N33Q+N101Q+T231R+N233R;
N33Q+N94Q+T231R+N233R;
N11Q+N33Q+T231R+N233R;
N33Q+G177A+T231R+N233R;
N33Q+N73Q+T231R+N233R;
D27R+N33Q+G91T+D96E+D111A+G163K+T231R+N233R+D254S+P256T;
D27R+N33Q+G91T+D96E+D111A+G163A+T231R+N233R+D254S+P256T;
N33Q+G38I+T231R+N233R;
N33Q+G38F+T231R+N233R;
N33Q+G38H+N200Q+T231R+N233R+N251S;
N33Q+G38T+T231R+N233R;
N11R+N33Q+G91T+W117I+G163K+T231R+N233R+D254S;
D27R+N33Q+G38A+G91T+D96E+D111A+G163K+T231R+N233R+D254S+P256T;
N11R+N33Q+G91T+W117I+G163K+T231R+N233R+D254S;
D27R+N33Q+G38A+G91T+D96E+D111A+G163A+T231R+N233R+D254S+P256T;
D27R+N33Q+V176Q+L227G+T231R+N233R+Q249R+D254S;
N33Q+G38A+G163A+T231R+N233R+P256A;
N33Q+W117I+V176Q+T231R+N233R;
N33Q+G177A+T231R+N233R+G246A;
N33Q G38H T231R N233R;
N11R+N33Q+G91T+G163K+V176Q+T231R+N233R+D254S;
N11R+N33Q+G38A+G91T+G163K+T231R+N233R+D254S;
N33Q+G163W+T231R+N233R;
N33Q+G38A+G163A+T231R+N233R;
D27R+N33Q+G91T+D96E+L97Q+D111A+T231R+N233R+D254S+P256T;
N33Q+G91T+N94R+D111A+W117L+V176W+T231R+N233R;
Q4P+D27R+N33Q+G91N+N94R+D111A+L206F+S216P+L227G+T231R+N233R+P256T;
D27R+N33Q+E43K+K46M+190V+G91N+N94R+D111A+T114I+S216P+L227G+T231R+N233R+P256T;
N33Q+W117S+T231R+N233R;
N33Q+G61R+V63R+G156R+V176W+T231R+N233R+P256I;
N33Q+D96N+G156R+V176W+T231R+N233R;
N33Q+G91T+N94S+D111A+S115L+G163T+V176I+T231R+N233R;
N11R+D27R+N33Q+E56Q+D57N+G91N+N94R+D111S+S216P+L227G+T231R+N233R+D254S+P256T;
D27R+N33Q+E56Q+D57N+G91N+N94R+D111S+S216P+L227G+T231R+N233R+D242E+D254S+P256T;
D27R+N33Q+G38A+E56Q+D57N+G91N+N94R+D111S+S216P+L227G+T231R+N233R+D254S+P256T;
N11R+N33Q+I90L+G163L+T231R+N233R;
N11R+D27R+N33Q+G91T+D96E+D111A+G163K+T231R+N233R+D254S+P256T;
N11R+N33Q+G38A+G91T+G112A+G163A+T231R+N233R+D254S;
N11R+N33Q+G91T+G163K+E210D+T231R+N233R+D254S;
N11R+N33Q+G91T+G163K+T231R+N233R+D254I;
N11R+N33Q+G91T+G163P+T231R+N233R+D254S;
N11R+N33Q+G38A+G91T+G163K+V176D+T231R+N233R+D254S;
E1D+N33Q+G38A+G91T+N94R+D111A+W117L+V176W+T231R+N233R;
N33Q+G163K+G177A+T231R+N233R+G246A;
N11R+N33Q+E56Q+G91T+G163K+T231R+N233R+D254S;
N11R+N33Q+190L+G163K+T231R+N233R+D254S;
D27R+N33Q+E56Q+D57N+G91N+N94R+D111S+S216P+L227G+T231R+N233R+Q249R+D254S+P256T;
D27R+N33Q+E56Q+D57N+G91N+N94R+D111S+S216P+E219D+L227G+T231R+N233R+D254S+P256T;
N11R+N33Q+G91T+G163K+V176I+T231R+N233R+D254S;
N11R+N33Q+G91T+G163K+V176Q+T231R+N233R+D254S;
N11R+N33Q+G91T+G163A+V176T+T231R+N233R+D254S;
N11R+N33Q+G91T+G163L+V176I+T231R+N233R+D254S;
N11R+N33Q+G91T+G163L+V176T+T231R+N233R+D254S;
N11R+N33Q+G91T+G163L+T231R+N233R+D254S;
N11R+N33Q+G91T+G163P+V176I+T231R+N233R+D254S;
N11R+N33Q+G91T+G163L+T231R+N233R+D254S+P256N;
D27R+N33Q+E56Q+D57N+G91N+N94R+D111S+G163T+S216P+L227G+T231R+N233R+Q249R+D254S+P256T;
Q4R+D27Q+N33Q+G91T+N94S+E99D+D111A+G163A+E210V+S216P+L227G+T231R+N233R+P256L;

Q4R+D27Q+N33Q+G91T+N94S+E99D+D111A+V176I+E210V+S216P+L227G+T231R+N233R+P256L;
D27R+N33Q+L227G+T231R+N233R+Q249R+D254S;
N11R+N33Q+T231R+N233R;
N33Q+G38A+G91T+G163K+T231R+N233R+D254S;
N33Q+W117Y+V176T+T231R+N233R;
N8L+N11R+N33Q+G91T+G163K+T231R+N233R+D254S;
N11R+N33Q+G38A+G91T+G163P+V176G+T231R+N233R+D254S;
N11R+N33Q+G91T+G163K+T231R+N233R+D254A+P256F;
N11R+N33Q+G91T+G163K+T231R+N233R+D254S+P256F;
N11R+N33Q+G91T+G163N+T231R+N233R+D254S;
N11R+N33Q+G91T+G163T+T231R+N233R+D254S;
N11R+N33Q+G91T+G163W+T231R+N233R+D254S;
N11R+N33Q+G91K+G163K+T231R+N233R+D254S;
N11R+N33Q+G91T+V141E+G163K+T231R+N233R+D254S;
N11R+N33Q+L52R+G91T+G163K+T231R+N233R+D254S;
N11R+N33Q+T37K+G91T+G163K+T231R+N233R+D254S;
N11R+N33Q+A68V+G91T+G163K+T231R+N233R+D254S;
N11R+N33Q+G91T+G163A+V176I+T231R+N233R+D254S;
N11R+N33Q+T37M+G91T+G163P+V176T+T231R+N233R+D254S;
N11R+N33Q+G91T+G163L+T231R+N233R+D254S;
N11R+N33Q+G91T+G163K+T231R+N233R+D254S+P256I;
N33Q+G38S+G156R+G163K+V176W+T231R+N233R;
N11R+D27R+N33Q+E56Q+D57N+G91N+N94R+D111S+G163K+S216P+L227G+T231R+N233R+D254S+P256T;
N11R+N33Q+G38A+G91T+G163Q+V176G+T231R+N233R+D254S;
N11R+N33Q+G38A+G91T+G163T+V176G+T231R+N233R+D254S;
N11R+N33Q+G38A+G91T+N94R+G163P+V176G+T231R+N233R+D254S;
E1N+N11R+N33Q+G38A+G91T+G163P+V176F+T231R+N233R;
E1N+F10L+N11R+N33Q+G38A+G91T+G163P+V176F+T231R+N233R;
E1N+N33Q+G38A+G91T+G163P+V176F+T231R+N233R+D254S;
E1N+N33Q+G38A+G91T+D111A+G163P+V176F+T231R+N233R;
E1N+N33Q+G38A+G91T+G163P+V176F+L227F+T231R+N233R;
E1N+N11R+N33Q+G38A+G91T+D111A+G163P+V176F+T231R+N233R;
E1N+N33Q+G38A+G91T+G163P+V176F+L227F+T231R+N233R+D254S;
E1N+N33Q+G38A+G91T+G163P+V176F+T231R+N233R+D254S+I255A+P256Q;
E1N+N11R+N33Q+G38A+G91T+D111A+G163P+V176F+T231R+N233R+D254S;
N33Q+G156R+V176W+T231R+N233R+P256I;
N11R+N33Q+G38A+G91T+D102G+S115L+G163K+T231R+N233R+D254S+256T;
N11R+N33Q+G38A+G91T+S115L+G163K+T231R+N233R+D254S+P256T;
E1N+N11R+N33Q+G91T+G163A+T231R+N233R+G246A+D254S;
N11R+D27R+N33Q+D57G+G91T+D96E+D111A+G163K+T231R+N233R+D254S+P256T;
N33Q+D96N+G156R+V176W+T231R+N233R+Q249R;
N11C+N33Q+G91T+G163K+T231R+N233R+D254S;
N11L+N33Q+G91T+G163K+T231R+N233R+D254S;
N11H+N33Q+G91T+G163K+T231R+N233R+D254S;
N11D+N33Q+G91T+G163K+T231R+N233R+D254S,
N11R+N33Q+G91T+D96W+G163K+T231R+N233R+D254S;
D27R+N33Q+G91T+D96E+L97Q+D111A+G163K+T231R+N233R+D254S+P256T;
N11P+N33Q+G91T+G163K+T231R+N233R+D254S;
Q4R+D27N+N33Q+G38A+G91T+N94S+E99D+D111A+V176I+E210V+S216P+L227G+T231R+N233R+P256L;
N11R+N33Q+E56Q+G163K+T231R+N233R+D254S;
N11R+N33Q+G91T+G163A+T231R+N233R+D254S;
N11R+N33Q+G91T+G163P+T231R+N233R+D254S; and
N11R+N33Q+G91T+G163K+L227G+P229R+T231R+N233R+D254S.

In a third particular embodiment, the lipase of the invention is selected from amongst lipases having the following substitutions, preferably sets of substitutions, as compared to the lipase of SEQ ID NO: 2:

N33Q+E87A+T231R+N233R;
N33Q+T231R+N233R+D254G;
N33Q+T231R+N233R+G240L;
N33Q+E210V+T231R+N233R+D254S;
N11R+N33Q+E210V+T231R+N233R+D254S;
N33Q+G91Y+Q126L+T231R+N233R;
N33Q+G163M+T231R+N233R;
N33Q+D111A+T231R+N233R+Q249R;
D27R+N33Q+G91A+D96E+L97Q+D111A+T231R+N233R+D254G+P256T;
N33Q+G91T+N94R+T231R+N233R+D254S;
N33Q+W117L+T231R+N233R+D254S;
N33Q+T231R+N233R+D242E;
N33Q+E87R+T231R+N233R;
N33Q+E56R+T231R+N233R;
N33Q+N162G+T231R+N233R;
N33Q+T231R+N233R+D254L;
N33Q+T231R+N233R+D254K;
D27V+N33Q+V60S+G91T+D96W+T231R+N233R+Q249R;
N33Q+D96N+L227G+T231R+N233R+Q249R;
N33Q+E219D+L227G+T231R+N233R+Q249R;
D27Q+N33Q+E219D+L227G+T231R+N233R+Q249R;
N33Q+D96E+E219D+L227G+T231R+N233R+Q249R;
N33Q+D111A+T231R+N233R+D254S;
N33Q+T231R+N233R+P256N;
N33Q+T231R+N233R+P256M;
D27R+N33Q+G91T+N94R+D111A+S216P+L227G+T231R+N233R;
D27R+N33Q+L227G+T231R+N233R+Q249R+D254S;
N33Q+G91T+D96N+D111A+V176I+T231R+N233R+D254S;
N33Q+G91T+N94S+D111A+V176I+T231R+N233R+D254S;
N33Q+G38I+G177A+T231R+N233R;
N33Q+G177A+T231R+N233R;
D27R+N33Q+G91T+D96E+D111A+G163A+T231R+N233R+D254S+P256T;
N33Q+G38F+T231R+N233R;
N33Q+G38H+N200Q+T231R+N233R+N251S;
N11R+N33Q+G91T+W117I+G163K+T231R+N233R+D254S;

D27R+N33Q+G38A+G91T+D96E+D111A+G163K+T231R+N233R+D254S+P256T;

N11R+N33Q+G91T+W117I+G163K+T231R+N233R+D254S;

D27R+N33Q+V176Q+L227G+T231R+N233R+Q249R+D254S;

N33Q+G38A+G163A+T231R+N233R+P256A;

N33Q+W117I+V176Q+T231R+N233R;

N33Q+G91T+N94R+D111A+W117L+V176W+T231R+N233R;

Q4P+D27R+N33Q+G91N+N94R+D111A+L206F+S216P+L227G+T231R+N233R+P256T;

D27R+N33Q+E43K+K46M+I90V+G91N+N94R+D111A+T114I+S216P+L227G+T231R+N233R+P256T;

N33Q+D96N+G156R+V176W+T231R+N233R;

N11R+D27R+N33Q+E56Q+D57N+G91N+N94R+D111S+S216P+L227G+T231R+N233R+D254S+P256T;

D27R+N33Q+E56Q+D57N+G91N+N94R+D111S+S216P+L227G+T231R+N233R+D242E+D254S+P256T;

D27R+N33Q+G38A+E56Q+D57N+G91N+N94R+D111S+S216P+L227G+T231R+N233R+D254S+P256T;

N11R+N33Q+190L+G163L+T231R+N233R;

N11R+D27R+N33Q+G91T+D96E+D111A+G163K+T231R+N233R+D254S+P256T;

N11R+N33Q+G38A+G91T+G112A+G163A+T231R+N233R+D254S;

N11R+N33Q+G91T+G163K+T231R+N233R+D254I;

N11R+N33Q+G38A+G91T+G163K+V176D+T231R+N233R+D254S;

N33Q+G163K+G177A+T231R+N233R+G246A;

D27R+N33Q+E56Q+D57N+G91N+N94R+D111S+S216P+L227G+T231R+N233R+Q249R+D254S+P256T;

N11R+N33Q+G91T+G163K+V176Q+T231R+N233R+D254S;

N11R+N33Q+G91T+G163L+V176I+T231R+N233R+D254S;

N11R+N33Q+G91T+G163P+V176I+T231R+N233R+D254S;

N11R+N33Q+G91T+G163L+T231R+N233R+D254S+P256N;

Q4R+D27Q+N33Q+G91T+N94S+E99D+D111A+G163A+E210V+S216P+L227G+T231R+N233R+P256L;

Q4R+D27Q+N33Q+G91T+N94S+E99D+D111A+V176I+E210V+S216P+L227G+T231R+N233R+P256L;

N33Q+G38A+G91T+G163K+T231R+N233R+D254S;

N11R+N33Q+G91T+G163K+T231R+N233R+D254A+P256F;

N11R+N33Q+G91T+G163K+T231R+N233R+D254S+P256F;

N11R+N33Q+G91T+G163T+T231R+N233R+D254S;

N11R+N33Q+G91T+G163W+T231R+N233R+D254S;

N11R+N33Q+G91K+G163K+T231R+N233R+D254S;

N11R+N33Q+L52R+G91T+G163K+T231R+N233R+D254S;

N11R+N33Q+T37K+G91T+G163K+T231R+N233R+D254S;

N11R+N33Q+A68V+G91T+G163K+T231R+N233R+D254S;

N11R+N33Q+T37M+G91T+G163P+V176T+T231R+N233R+D254S;

N33Q+G38S+G156R+G163K+V176W+T231R+N233R;

N11R+D27R+N33Q+E56Q+D57N+G91N+N94R+D111S+G163K+S216P+L227G+T231R+N233R+D254S+P256T;

N11R+N33Q+G38A+G91T+G163T+V176G+T231R+N233R+D254S;

E1N+N11R+N33Q+G38A+G91T+G163P+V176F+T231R+N233R;

E1N+F10L+N11R+N33Q+G38A+G91T+G163P+V176F+T231R+N233R;

E1N+N33Q+G38A+G91T+G163P+V176F+T231R+N233R+D254S;

E1N+N11R+N33Q+G38A+G91T+D111A+G163P+V176F+T231R+N233R;

E1N+N33Q+G38A+G91T+G163P+V176F+L227F+T231R+N233R+D254S;

E1N+N33Q+G38A+G91T+G163P+V176F+T231R+N233R+D254S+I255A+P256Q;

N11R+N33Q+G38A+G91T+D102G+S115L+G163K+T231R+N233R+D254S+P256T;

N11R+N33Q+G38A+G91T+S115L+G163K+T231R+N233R+D254S+P256T;

E1N+N11R+N33Q+G91T+G163A+T231R+N233R+G246A+D254S;

N11R+D27R+N33Q+D57G+G91T+D96E+D111A+G163K+T231R+N233R+D254S+P256T;

N33Q+D96N+G156R+V176W+T231R+N233R+Q249R;

N11C+N33Q+G91T+G163K+T231R+N233R+D254S;

N11L+N33Q+G91T+G163K+T231R+N233R+D254S;

N11H+N33Q+G91T+G163K+T231R+N233R+D254S;

N11D+N33Q+G91T+G163K+T231R+N233R+D254S;

N11R+N33Q+G91T+D96W+G163K+T231R+N233R+D254S;

D27R+N33Q+G91T+D96E+L97Q+D111A+G163K+T231R+N233R+D254S+P256T;

N11P+N33Q+G91T+G163K+T231R+N233R+D254S;

N11R+N33Q+E56Q+G163K+T231R+N233R+D254S;

N11R+N33Q+G91T+G163P+T231R+N233R+D254S; and

N11R+N33Q+G91T+G163K+L227G+P229R+T231R+N233R+D254S.

In a fourth particular embodiment, the lipase of the invention is selected from amongst lipases having the following substitutions, preferably sets of substitutions, as compared to the lipase of SEQ ID NO: 2:

N33Q+G91T+N94R+T231R+N233R+D254S;

N33Q+E87R+T231R+N233R;

D27V+N33Q+V60S+G91T+D96W+T231R+N233R+Q249R;

N33Q+E219D+L227G+T231R+N233R+Q249R;

N33Q+D96E+E219D+L227G+T231R+N233R+Q249R;

D27R+N33Q+L227G+T231R+N233R+Q249R+D254S;

D27R+N33Q+G91T+D96E+D111A+G163A+T231R+N233R+D254S+P256T;

D27R+N33Q+G38A+G91T+D96E+D111A+G163K+T231R+N233R+D254S+P256T;

N33Q+G38A+G163A+T231R+N233R+P256A;

N11R+N33Q+190L+G163L+T231R+N233R;

N11R+N33Q+G38A+G91T+G112A+G163A+T231R+N233R+D254S;

Q4R+D27Q+N33Q+G91T+N94S+E99D+D111A+V176I+E210V+S216P+L227G+T231R+N233R+P256L;

N11R+N33Q+G91T+G163W+T231R+N233R+D254S;

N11R+N33Q+L52R+G91T+G163K+T231R+N233R+D254S;

E1N+N11R+N33Q+G91T+G163A+T231R+N233R+G246A+D254S;

N33Q+D96N+G156R+V176W+T231R+N233R+Q249R;

N11L+N33Q+G91T+G163K+T231R+N233R+D254S;

N11R+N33Q+G91T+D96W+G163K+T231R+N233R+D254S; and

D27R+N33Q+G91T+D96E+L97Q+D111A+G163K+T231R+N233R+D254S+P256T.

In a fifth particular embodiment, the lipase of the invention is selected from amongst lipases having the following substitutions, preferably sets of substitutions, as compared to the lipase of SEQ ID NO: 2:

N11R+N33Q+G91T+G163W+T231R+N233R+D254S;

N33Q+G38S+G156R+G163K+V176W+T231R+N233R; and

N11L+N33Q+G91T+G163K+T231R+N233R+D254S.

Variants of the lipase of amino acids 1-269 of SEQ ID NO: 2 with the above-listed substitutions (each of the five particular embodiments) all have an improved in vitro digestion performance, i.e., an improvement factor (IF), preferably average IF minus standard deviation, of above 1.00, or of at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 5 is preferably used. A preferred diet is diet 1. Active Site Titration (AST, Example 6) is preferably used to determine the lipase concentration.

(E) In a first particular embodiment, the lipase of the invention is selected from amongst lipases having the following substitutions, preferably sets of substitutions, as compared to the lipase of SEQ ID NO: 2:

D27R+N33Q+G91A+D96E+L97Q+D111A+T231R+N233R+P256T;

N33Q+E210D+T231R+N233R;

N33Q+T231R+N233R;

N33Q+D111A+T231R+N233R;

N33Q+G91T+T231R+N233R;

D27Q+N33Q+T231R+N233R;

Q9H+N33Q+D102E+T231R+N233R;

N33Q+E56Q+T231R+N233R;

N33Q+190L+G163L+T231R+N233R;

D27R+N33Q+G91A+D96E+D111A+T231R+N233R+D254G+P256T;

N33Q+N39S+T231R+N233R;

N33Q+N94R+T231R+N233R;

N33Q+T231R+N233R+D254S;

N33Q+G91T+G163K+T231R+N233R+D254G;

N33Q+G91T+G163K+T231R+N233R+D254S;

N11R+N33Q+G91T+G163K+T231R+N233R+D254S;

D27N+N33Q+G91T+G163K+T231R+N233R+D254S;

N33Q+T231R+N233R;

K98I+T231R+N233R+N251S;

N33Q+G163P+T231R+N233R;

N33Q+G163D+T231R+N233R;

N33Q+G163T+T231R+N233R;

N33Q+G163W+T231R+N233R;

N33Q+G38A+G163A+T231R+N233R;

N33Q+D11A+T231R+N233R+D254S;

D27R+N33Q+G91T+D96E+L97Q+D111A+T231R+N233R+D254S+P256T;

N33Q+T231R+N233R+P256A;

N33Q+T231R+N233R+P256S;

N33Q+G91T+N94S+D111A+V176I+T231R+N233R+D254S;

N33Q+S115L+T231R+N233R;

N33Q+G38A+G91T+G163K+T231R+N233R+D254S;

D27V+N33Q+G91A+N94R+D111A+G163K+L227F+T231R+N233R+Q249R+D254S;

D27R+N33Q+G38A+G91T+D96E+D111A+T231R+N233R+D254S+P256T;

N33Q+G91A+N94K+D111A+G163K+L227F+T231R+N233R+Q249R;

N33Q+G91A+N94K+D111A+G163K+L227F+T231R+N233R+Q249R+D254S;

N33Q+G91T+K98I+T114I+G163K+T231R+N233R+D254S;

N33Q+G91T+K98I+G163K+T231R+N233R+D254S+P256L; and

N33Q+G91T+T114I+G163K+T231R+N233R+D254S+P256L.

In a second particular embodiment, the lipase of the invention is selected from amongst lipases having the following substitutions, preferably sets of substitutions, as compared to the lipase of SEQ ID NO: 2:

D27R+N33Q+G91A+D96E+L97Q+D111A+T231R+N233R+P256T;

N33Q+E210D+T231R+N233R;

N33Q+T231R+N233R;

N33Q+D111A+T231R+N233R;

N33Q+G91T+T231R+N233R;

N33Q+N94R+T231R+N233R;

N33Q+T231R+N233R+D254S;

N11R+N33Q+G91T+G163K+T231R+N233R+D254S;

D27N+N33Q+G91T+G163K+T231R+N233R+D254S;

N33Q+G163P+T231R+N233R;

N33Q+G91A+N94K+D111A+G163K+L227F+T231R+N233R+Q249R+D254S;

N33Q+G91T+K98I+T114I+G163K+T231R+N233R+D254S; and

N33Q+G91T+T114I+G163K+T231R+N233R+D254S+P256L.

In a third particular embodiment, the lipase of the invention is selected from amongst lipases having the following substitutions, preferably sets of substitutions, as compared to the lipase of SEQ ID NO: 2:

D27R+N33Q+G91A+D96E+L97Q+D111A+T231R+N233R+P256T;

N33Q+G91T+T231R+N233R;

D27N+N33Q+G91T+G163K+T231R+N233R+D254S; and

N33Q+G91T+K98I+T114I+G163K+T231R+N233R+D254S.

Variants of the lipase of amino acids 1-269 of SEQ ID NO: 2 with the above-listed substitutions (each of the three particular embodiments) all have an improved in vitro digestion performance, i.e., an improvement factor (IF), preferably average IF minus standard deviation, of above 1.00, or of at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 3 is preferably used. A preferred diet is diet I. Active Site Titration (AST, Example 6) is preferably used to determine the lipase concentration.

(F) In a first particular embodiment, the lipase of the invention is selected from amongst lipases having the following substitutions, preferably sets of substitutions, as compared to the lipase of SEQ ID NO: 2:

D27R+N33Q+G91A+D96E+L97Q+D111A+T231R+N233R+P256T;

D27R+N33Q+G91A+D96E+L97Q+D1111A+T231R+N233R+P256T;

N33Q+E210D+T231R+N233R;

N33Q+D111A+T231R+N233R;

N33Q+G91T+T231R+N233R;

D27Q+N33Q+T231R+N233R;

Q9H+N33Q+D102E+T231R+N233R;

N33Q+G91T+G163K+T231R+N233R;

N33Q+E56Q+T231R+N233R;

N33Q+190L+G163L+T231R+N233R;

N33Q+N94R+T231R+N233R;

N33Q+T231R+N233R+D254S;

N33Q+G91T+G163K+T231R+N233R+D254G;
N33Q+G91T+G163K+T231R+N233R+D254S;
N11R+N33Q+G91T+G163K+T231R+N233R+D254S;
D27N+N33Q+G91T+G163K+T231R+N233R+D254S;
N33Q+T231R+N233R;
K98I+T231R+N233R+N251S;
N33Q+G163P+T231R+N233R;
N33Q+G163D+T231R+N233R;
N33Q+G163T+T231R+N233R;
N33Q+G163W+T231R+N233R;
N33Q+G38A+G163A+T231R+N233R;
N33Q+D111A+T231R+N233R+D254S;
D27R+N33Q+G91A+D96E+L97Q+D111A+T231R+N233R+D254S+P256T;
D27R+N33Q+G91T+D96E+L97Q+D111A+T231R+N233R+D254S+P256T;
N33Q+T231R+N233R+D254Q;
N33Q+T231R+N233R+D254I;
N33Q+S216P+L227G+T231R+N233R+Q249R;
N33Q+T231R+N233R+P256A;
N33Q+T231R+N233R+P256L;
N33Q+T231R+N233R+P256S;
N33Q+G91T+N94S+D111A+V176I+T231R+N233R+D254S;
N33Q+S115L+T231R+N233R;
N33Q+G38A+G91T+G163K+T231R+N233R+D254S;
D27V+N33Q+G91A+N94R+D111A+G163K+L227F+T231R+N233R+Q249R;
D27V+N33Q+G91A+N94R+D111A+G163K+L227F+T231R+N233R+Q249R+D254S;
N33Q+G161A+T231R+N233R;
N33Q G38M T231R N233R;
N33Q G38F T231R N233R;
N33Q+G91A+N94K+D111A+G163K+L227F+T231R+N233R+Q249R;
N33Q+G91A+N94K+D111A+G163K+L227F+T231R+N233R+Q249R+D254S;
N33Q+G91T+K98I+T114I+G163K+T231R+N233R+D254S;
N33Q+G91T+K98I+G163K+T231R+N233R+D254S+P256L; and
N33Q+G91T+T114I+G163K+T231R+N233R+D254S+P256L.

In a second particular embodiment, the lipase of the invention is selected from amongst lipases having the following substitutions, preferably sets of substitutions, as compared to the lipase of SEQ ID NO: 2:

D27R+N33Q+G91A+D96E+L97Q+D111A+T231R+N233R+P256T;
D27R+N33Q+G91A+D96E+L97Q+D111A+T231R+N233R+P256T;
N33Q+E210D+T231R+N233R;
N33Q+D111A+T231R+N233R;
N33Q+G91T+T231R+N233R;
D27Q+N33Q+T231R+N233R;
N33Q+E56Q+T231R+N233R;
N33Q+I90L+G163L+T231R+N233R;
N33Q+G91T+G163K+T231R+N233R+D254G;
N33Q+G91T+G163K+T231R+N233R+D254S;
N11R+N33Q+G91T+G163K+T231R+N233R+D254S;
D27N+N33Q+G91T+G163K+T231R+N233R+D254S;
N33Q+G163P+T231R+N233R;
N33Q+G163D+T231R+N233R;
N33Q+G163W+T231R+N233R;
N33Q+G38A+G163A+T231R+N233R;
N33Q+T231R+N233R+D254Q;
N33Q+T231R+N233R+D254I;
N33Q+T231R+N233R+P256S;
N33Q+S115L+T231R+N233R;
N33Q+G38A+G91T+G163K+T231R+N233R+D254S;
D27V+N33Q+G91A+N94R+D111A+G163K+L227F+T231R+N233R+Q249R;
N33Q G38M T231R N233R;
N33Q G38F T231R N233R;
N33Q+G91T+K98I+T114I+G163K+T231R+N233R+D254S;
N33Q+G91T+K98I+G163K+T231R+N233R+D254S+P256L; and
N33Q+G91T+T114I+G163K+T231R+N233R+D254S+P256L.

In a third particular embodiment, the lipase of the invention is selected from amongst lipases having the following substitutions, preferably sets of substitutions, as compared to the lipase of SEQ ID NO: 2:

N33Q+E210D+T231R+N233R;
N33Q+G91T+T231R+N233R;
D27Q+N33Q+T231R+N233R;
N33Q+190L+G163L+T231R+N233R;
D27N+N33Q+G91T+G163K+T231R+N233R+D254S;
D27V+N33Q+G91A+N94R+D111A+G163K+L227F+T231R+N233R+Q249R;
N33Q G38M T231R N233R;
N33Q G38F T231R N233R;
N33Q+G91T+K98I+T114I+G163K+T231R+N233R+D254S;

Variants of the lipase of amino acids 1-269 of SEQ ID NO: 2 with the above-listed substitutions (each of the three particular embodiments) all have an improved in vitro digestion performance, i.e., an improvement factor (IF), preferably average IF minus standard deviation, of above 1.00, or of at least 1.50 (or 1.5), 2.00 (or 2.0), 2.50 (or 2.5), 3.00 (or 3.0), 3.50 (or 3.5), or at least 4.00 (or 4.0), preferably of at least 5.00 (or 5.0), 6.00 (or 6.0), 7.00 (or 7.0), 8.00 (or 8.0), 9.00 (or 9.0), 10.00 (or 10.0), or at least 11.00 (or 11.0). A gastric step of pH 5 is preferably used. A preferred diet is diet I. $A_{280}$ is preferably used to determine the lipase concentration, preferably using the extinction coefficient 1.24 $A_{280}$/mg.

The lipases of the invention may have a bile salt ratio improvement vs reference of at least 1.2, 1.4, 1.6, 1.8, or at least 2.0. More preferably the lipases of the invention may have a bile salt ratio improvement vs reference of at least 2.2, 2.5, 2.8, or at least 3.0. Even more preferably the lipases of the invention may have a bile salt ratio improvement vs reference of at least 3.2, 3.4, 3.6, 3.8, or at least 4.0. These ratios may also be referred to as, e.g., 3×, 3-fold, or 300%, all corresponding to a ratio of 3.0—and vice versa for other ratios.

In a particular embodiment, the lipase of the invention is selected from amongst lipases having the following substitutions, preferably sets of substitutions, as compared to the lipase of SEQ ID NO: 2:

D27R+N33Q+E43K+K46M+I90V+G91N+N94R+D111A+T114I+S216P+L227G+T231R+N233R+P256T;
G23E+D27R+N33Q+L52R+G91N+N94R+D111A+T114I+V141E+S216P+L227G+T231R+N233R+P256T;
N33Q+G38W+G91T+T114I+G163K+E210D+T231R+N233R+P256T;
D27I+N33Q+G91T+D96E+K98T+T114I+G163K+E210D+T231R+N233R+P256T;
N33Q+G91T+D96E+K98T+T114I+T231R+N233R+G163S;
N33Q+G38W+G91T+T114I+G163K+E210V+T231R+N233R;
Q4P+D27R+N33Q+G91N+N94R+D111A+R205I+L206F+S216P+L227G+T231R+N233R+P256T;

N33Q+G91T+D96E+K98T+T114I+G163K+E210D+T231R+N233R;
D27R+N33Q+T37K+N71I+G91N+N94R+K98I+D111A+S216P+L227G+T231R+N233R+P256T;
Q4H+D27R+N33Q+G91N+N94R+D111A+V154L+S216P+L227G+T231R+N233R+P256T;
N33Q+G91T+D96E+K98T+T114I+G163S+E210V+T231R+N233R+D254K+P256A;
N33Q+G91T+T114I+G163K+E210D+T231R+N233R+D254G+P256A;
D27R+N33Q+L52I+V60E+G91N+N94R+D111A+T114I+V168M+E210D+S216P+L227G+T231R+N233R+P256T;
D27R+N33Q+G91N+N94R+D111A+T114I+R179T+S216P+L227G+T231R+N233R+P256T;
D27R+A30V+N33Q+G91N+N94R+G109A+D111A+G190D+S216P+L227G+T231R+N233R+P256T;
D27R+N33Q+G91N+N94R+K98I+D111A+N162S+S216P+L227G+T231R+N233R+P256T;
N26H+D27R+N33Q+G91N+N94R+D111A+V154F+G190C+S216P+L227G+T231R+N233R+P256T;
D27N+N33Q+G91T+T114I+G163S+E210D+T231R+N233R+P256T;
D27R+N33Q+G91N+N94R+D111A+S216P+L227G+T231R+N233R;
D27R+N33Q+T37K+N71I+G91N+N94R+K98I+D111A+S216P+L227G+Y231R+N233R+P256T;
D27R+N33Q+G91T+T114I+G163W+E210D+T231R+N233R;
D27R+N33Q+G91N+N94R+K98I+D111A+S216P+L227G+T231R+N233R+P256T;
D27R+N33Q+G91N+N94R+L97M+D111A+S216P+T226N+L227G+T231R+N233R+P256T+L269H;
D27R+N33Q+G91N+N94R+D111A+V154I+S216P+L227G+T231R+N233R+P256T;
N33Q+G91T+T114I+E210V+T231R+N233R+D254K+P256A
D27R+N33Q+N71S+G91N+N94R+D111A+H135D+S216P+L227G+T231R+N233R+P256T;
N33Q+G91T+T114I+G163K+E210D+T231R+N233R;
D27R+N33Q+I76T+G91N+N94R+R108M+D111A+S216P+L227G+T231R+N233R+P256T;
D27R+N33Q+N39S+G91N+N94R+D111A+S216P+L227G+T231R+N233R+P256T;
D27R+N33Q+A49T+G91N+N94R+D111A+Y138F+G163R+S216P+L227G+T231R+N233R+P256T;
N33Q+G91A+N94K+D111A+G163K+L227F+T231R+N233R+Q249R;
N33Q+G91T+K98I+T114I+G163K+T231R+N233R+D254S; and
N33Q+G91T+K98I+G163K+T231R+N233R+D254S+P256L.

In a more preferred embodiment, the lipase of the invention is selected from amongst lipases having the following substitutions, preferably sets of substitutions, as compared to the lipase of SEQ ID NO: 2:
D27R+N33Q+E43K+K46M+I90V+G91N+N94R+D111A+T114I+S216P+L227G+T231R+N233R+P256T;
G23E+D27R+N33Q+L52R+G91N+N94R+D111A+T114I+V141E+S216P+L227G+T231R+N233R+P256T;
N33Q+G38W+G91T+T114I+G163K+E210D+T231R+N233R+P256T;
D27I+N33Q+G91T+D96E+K98T+T114I+G163K+E210D+T231R+N233R+P256T;
N33Q+G91T+D96E+K98T+T114I+T231R+N233R+G163S;
N33Q+G38W+G91T+T114I+G163K+E210V+T231R+N233R;
Q4P+D27R+N33Q+G91N+N94R+D111A+R205I+L206F+S216P+L227G+T231R+N233R+P256T;
N33Q+G91T+D96E+K98T+T114I+G163K+E210D+T231R+N233R;
D27R+N33Q+T37K+N71I+G91N+N94R+K98I+D111A+S216P+L227G+T231R+N233R+P256T;
Q4H+D27R+N33Q+G91N+N94R+D111A+V154L+S216P+L227G+T231R+N233R+P256T;
N33Q+G91T+D96E+K98T+T114I+G163S+E210V+T231R+N233R+D254K+P256A;
N33Q+G91T+T114I+G163K+E210D+T231R+N233R+D254G+P256A;
D27R+N33Q+L52I+V60E+G91N+N94R+D111A+T114I+V168M+E210D+S216P+L227G+T231R+N233R+P256T;
D27R+N33Q+G91N+N94R+D111A+T114I+R179T+S216P+L227G+T231R+N233R+P256T;
D27R+A30V+N33Q+G91N+N94R+G109A+D111A+G190D+S216P+L227G+T231R+N233R+P256T;
D27R+N33Q+G91N+N94R+K98I+D111A+N162S+S216P+L227G+T231R+N233R+P256T;
N26H+D27R+N33Q+G91N+N94R+D111A+V154F+G190C+S216P+L227G+T231R+N233R+P256T;
D27N+N33Q+G91T+T114I+G163S+E210D+T231R+N233R+P256T;
D27R+N33Q+G91N+N94R+D111A+S216P+L227G+T231R+N233R;
D27R+N33Q+T37K+N71I+G91N+N94R+K98I+D111A+S216P+L227G+T231R+N233R+P256T;
D27R+N33Q+G91T+T114I+G163W+E210D+T231R+N233R;
D27R+N33Q+G91N+N94R+K98I+D111A+S216P+L227G+T231R+N233R+D254S; and
N33Q+G91T+K98I+T114I+G163K+T231R+N233R+D254S; and
N33Q+G91T+K98I+G163K+T231R+N233R+D254S+P256L.

In a most preferred embodiment, the lipase of the invention is selected from amongst lipases having the following substitutions, preferably sets of substitutions, as compared to the lipase of SEQ ID NO: 2:
D27R+N33Q+E43K+K46M+I90V+G91N+N94R+D111A+T114I+S216P+L227G+T231R+N233R+P256T;
G23E+D27R+N33Q+L52R+G91N+N94R+D111A+T114I+V141E+S216P+L227G+T231R+N233R+P256T;
N33Q+G38W+G91T+T114I+G163K+E210D+T231R+N233R+P256T;
D27I+N33Q+G91T+D96E+K98T+T141I+G163K+E210D+T231R+N233R+P256T;
N33Q+G91T+D96E+K98T+T114I+T231R+N233R+G163S;
N33Q+G38W+G91T+T114I+G163K+E210V+T231R+N233R;
Q4P+D27R+N33Q+G91N+N94R+D111A+R205I+L206F+S216P+L227G+T231R+N233R+P256T;
N33Q+G91T+D96E+K98T+T114I+G163K+E210D+T231R+N233R; and
N33Q+G91T+K98I+T114I+G163K+T231R+N233R+D254S.

Variants of the lipase of amino acids 1-269 of SEQ ID NO: 2 with the above-listed substitutions (each of the three embodiments) all have an improved in vitro digestion performance, i.e., an improved stability at pH 3 in the presence of pepsin, more in particular an improved residual activity measured on PNP-palmitate at pH 8.0 and 20° C. (or room temperature) after incubation for 3 hours at pH 3.0 and 20° C. (or room temperature) in the presence of 75 ug/mL pepsin, preferably an improved % residual activity (% RA) as determined by the method of Example 8. In particular embodiments, the % RA is at least 30, at least 50, at least 70, at least 80, or at least 90%. An improvement ratio may be defined as the ratio of % RA of the lipase in question to the % RA of the reference lipase. This improvement ratio preferably is at least 1.5, 2.0, 2.5, 3.0, 3.5, 4.0, 4.5, or at least 4.5. The improvement ratio can be calculated from the results in Table 10 by dividing the % RA of the lipase in question with the % RA of the reference lipase (e.g., the lipase of SEQ ID NO: 2, or SEQ ID NO: 1, or another reference lipase, as desired).

The lipases of the invention may have a bile salt ratio improvement vs reference of at least 1.2, 1.4, 1.6, 1.8, or at least 2.0. More preferably the lipases of the invention may have a bile salt ratio improvement vs reference of at least 2.2, 2.5, 2.8, or at least 3.0. Even more preferably the lipases of the invention may have a bile salt ratio improvement vs reference of at least 3.2, 3.4, 3.6, 3.8, or at least 4.0. These ratios may also be referred to as, e.g., 3×, 3-fold, or 300%, all corresponding to a ratio of 3.0— and vice versa for other ratios.

In a particular embodiment, the lipase of the invention is selected from amongst lipases having the following substitutions, preferably sets of substitutions, as compared to the lipase of SEQ ID NO: 2:

D27V+N33Q+G91A+N94R+D111A+G163K+L227F+T231R+N233R+Q249R+D254S:

N33Q+G91A+N94K+D111A+G163K+L227F+T231R+N233R+Q249R;

G23E+D27R+N33Q+L52R+G91N+N94R+D111A+T114I+V141E+S216P+L227G+T231R+N233R+P256T;

D27R+N33Q+E43K+K46M+190V+G91N+N94R+D111A+T114I+S216P+L227G+T231R+N233R+P256T;

G23E+D27R+N33Q+L52R+G91N+N94R+D111A+T114I+V141E+S216P+L227G+T231R+N233R+P256T

D27R+N33Q+E43K+K46M+190V+G91N+N94R+D111A+T114I+S216P+L227G+T231R+N233R+P256T;

N33Q+G91T+T114I+E210V+D254K+P256A;

N33Q+G91T+D96E+K98T+T114I+G163S+E210V+D254K+P256A;

L52I+V60E+T114I+V168M+E210D;

D27R+N33Q+A49T+G91N+N94R+D111A+Y138F+G163R+S216P+L227G+T231R+N233R+P256T;

D27R+N33Q+I76T+G91N+N94R+R108M+D111A+S216P+L227G+T231R+N233R+P256T; and

D27R+N33Q+E43K+K46M+I90V+G91N+N94R+D111A+T114I+S216P+P227G+T231R+N233R+P256T.

More preferably, the lipase of the invention is selected from amongst lipases having the following substitutions, preferably sets of substitutions, as compared to the lipase of SEQ ID NO: 2:

D27V+N33Q+G91A+N94R+D111A+G163K+L227F+T231R+N233R+Q249R+D254S;

N33Q+G91A+N94K+D111A+G163K+L227F+T231R+N233R+Q249R;

G23E+D27R+N33Q+L52R+G91N+N94R+D111A+T114I+V141E+S216P+L227G+T231R+N233R+P256T;

D27R+N33Q+E43K+K46M+I90V+G91N+N94R+D111A+T114I+S216P+L227G+T231R+N233R+P256T;

G23E+D27R+N33Q+L52R+G91N+N94R+D111A+T114I+V141E+S216P+L227G+T231R+N233R+P256T;

D27R+N33Q+E43K+K46M+I90V+G91N+N94R+D111A+T114I+S216P+L227G+T231R+N233R+P256T; and

N33Q+G91T+T114I+E210V+D254K+P256A.

Even more preferably, the lipase of the invention is selected from amongst lipases having the following substitutions, preferably sets of substitutions, as compared to the lipase of SEQ ID NO: 2:

D27V+N33Q+G91A+N94R+D111A+G163K+L227F+T231R+N233R+Q249R+D254S;

N33Q+G91A+N94K+D111A+G163K+L227F+T231R+N233R+Q249R;

G23E+D27R+N33Q+L52R+G91N+N94R+D111A+T114I+V141E+S216P+L227G+T231R+N233R+P256T;

D27R+N33Q+E43K+K46M+I90V+G91N+N94R+D111A+T114I+S216P+L227G+T231R+N233R+P256T;

G23E+D27R+N33Q+L52R+G91N+N94R+D111A+T114I+V141E+S216P+L227G+T231R+N233R+P256T; and

N33Q+G91T+T114I+E210V+D254K+P256A.

In a most preferred embodiment, the lipase of the invention is selected from amongst lipases having the following substitutions, preferably sets of substitutions, as compared to the lipase of SEQ ID NO: 2:

G23E+D27R+N33Q+L52R+G91N+N94R+D111A+T114I+V141E+S216P+L227G+T231R+N233R+P256T.

Variants of the lipase of amino acids 1-269 of SEQ ID NO: 2 with the above-listed substitutions (each of the four embodiments) all have an improved in vitro digestion performance, i.e., an improved activity on PNP-Oleate at pH 5.0 in the presence of 2 mM bile salts, more in particular an improved bile salt ratio as determined by the method in Example 9.

In a further particular embodiment, the lipase of the invention is selected from amongst lipases having the following substitutions, preferably sets of substitutions, as compared to the lipase of SEQ ID NO: 2:

N33Q+G91T+G163K+T231R+N233R+D254G;

N33Q+G91T+G163K+T231R+N233R+D254S; and

N11R+N33Q+G91T+G163K+T231R+N233R+D254S.

A most preferred lipase comprises the following substitutions, preferably sets of substitutions, as compared to the lipase of SEQ ID NO: 2:

N11R+N33Q+G91T+G163K+T231R+N233R+D254S.

In a particular embodiment, the lipase of the invention has an improved activity at low pH. In an activity context, low pH means a pH in the range of from 4 to 7, e.g. pH 4.0, 4.5, 5.0, 5.5, 6.0, 6.5, or 7.0. A preferred low pH is pH 6.0. In preferred embodiments, the activity at pH 6.0 is determined: i) at 37° C.; ii) with the substrate of trilinolein, preferably in a concentration of 8 mM; iii) with bile salts present during the incubation of enzyme and substrate, preferably in a concentration of 10 mM; iv) using as assay buffer 100 mM imidazole, 100 mM acetate, 100 mM malonic acid, pH 6.0; v) with $CaCl_2$ being present during the incubation of enzyme and substrate, preferably in a concentration of 1 mM; and/or vi) with an amount of purified lipase corresponding to 0.01 mg EP/mL (EP=enzyme protein, based on $A_{280)}$). In additional preferred embodiments, vii) the enzyme is diluted before the assay (e.g., in order to obtain an appropriate concentration for assay purposes) in 5 mM $NaH_2PO_4$ pH 7.0; iix) enzyme and substrate are incubated for 30 minutes; ix) enzyme and substrate are incubated in micro titer plates (MTP), and preferably shaken with 700 rpm; x) the enzymatic reaction is stopped with a stop solution, preferably (2.2% Triton-X100, 0.22 M Phosphoric acid), more preferably including pepsin (70 mg/l); xi) the free fatty acids generated as a result of the enzyme reaction are determined by an enzymatic color test, such as NefaC; and/or xii) the improvement in activity at pH 6.0 is indicated relative to the activity under the same conditions of a reference lipase such as the lipase having amino acids 1-269 of SEQ ID NO: 1 or 2, preferably 2, or relative to variant LV2934. For more details regarding the test method, please refer to Example 3. Particular examples of lipase variants of an improved activity at pH 6.0 are (relative to the lipase having amino acids 1-269 of SEQ ID NO: 2): LVA049, LVA349, LVA023, LVA099, SEQ ID NO: 1, LVA061, LV2934, LV1330, LVA043, LVA041, LVA012, LV1857, and LV1855 (see Table 1 for their structure). The LVA049, LVA349, LVA023, and LVA099 lipase variants are particularly preferred (improved also as compared to the SEQ ID NO: 1 lipase). The LVA049 and LVA349 lipase variants are even more preferred. A most preferred lipase, from a pH-activity point of view, is the LVA049 lipase variant.

In another particular embodiment, the lipase of the invention has an improved stability at low pH. In a stability context, low pH means a pH in the range of from 2 to 6, e.g., pH 2.0, 2.5, 3.0, 3.5, 4.0, 4.5, 5.0, 5.5, or 6.0. A preferred low pH is 3.0. The stability of a purified lipase enzyme is determined by incubating the enzyme at 37° C. at the desired pH (e.g., 3.0) for 1, 15, 45, and 120 minutes, following which residual lipase activity is measured on p-Nitrophenyl caprylate at pH 8 and room temperature (RT). In preferred embodiments, i) the buffer used for the stability pre-incubation (stability buffer) is 200 mM imidazole, 200 mM acetate, 200 mM malonic acid, adjusted to the desired pH (e.g., 3.0); ii) the enzymes are first diluted in 20 mM $NaH_2PO_4$ pH 7.0, 0.01% Triton-X100 to working solutions of 0.4 or 0.8 mg enzyme protein per ml, preferably based on $A_{280}$, iii) the enzyme concentration during the pre-incubation is 0.05 or 0.1 mg enzyme protein per ml, and for this dilution the buffer is preferably enzyme dilution buffer: 20 mM acetate pH 6, 0.01% Triton-X100; iv) the pre-incubation is in micro titer plates (MTP) with shaking, preferably with 700 rpm; v) for the subsequent determination of residual activity (RA), enzyme-containing aliquots withdrawn from the pre-incubation step are diluted at least 20 times in the following residual activity buffer (RA buffer): 200 mM Tris (tris-hydroxymethyl aminomethan, 2-amino-2-hydroxymethyl-1,3-propandiol, pH 8, 0.4% Triton-X100, 1 mM $CaCl_2$; vi) the residual activity is measured on p-Nitrophenyl caprylate at pH 8.0 and RT and is measured by way of kinetics (velocity; rate) at 405 nm for 5 minutes; vii) the % residual activity is calculated as follows: The rate within each pH for each withdraw (1, 15, 45, 120 minutes; or 1, 60, 120 minutes) is subtracted the rate for no enzyme control, if applicable with bile salts or pepsin (see below iix) and ix)), and this corrected rate is then divided by the highest value within each pH and multiplied by 100. Optionally, the enzymes are pre-incubated iix) in the presence of bile salts, preferably in a concentration of 10 mM, and/or ix) in the presence of pepsin (70 mg/l). For more details regarding this test method, please refer to Example 4.

In further particular embodiments, the lipase of the invention has a % residual activity, determined as described above and in Example 4, of at least 60, 65, 70, 72, 74, 76, 78, 80, 82, 84, 86, 88, 90, or 92 after 120 minutes of incubation at pH 3.0 in buffer.

In further particular embodiments, the lipase of the invention has a % residual activity, determined as described above and in Example 4, of at least 82, 83, 84, 85, 86, 87, 88, or at least 89 after 60 minutes of incubation at pH 3.0 in buffer.

In still further particular embodiments, the lipase of the invention has a % residual activity, determined as described above and in Example 4, of at least 35, 40, 45, 50, 55, 60, 65, 70, 72, 74, 76, 78, 80, 82, 84, 86, 88, 90, 92, or 94 after 45 minutes of incubation at pH 3.0 in the presence of pepsin.

In still further particular embodiments, the lipase of the invention has a % residual activity, determined as described above and in Example 4, of at least 20, 30, 40, 50, 60, 70, 80, 82, 84, 86, 88, or at least 89 after 60 minutes of incubation at pH 3.0 in the presence of pepsin.

In still further particular embodiments, the lipase of the invention has a % residual activity, determined as described above and in Example 4, of at least 2, 4, 6, 8, 10, 20, 30, 40, 50, 60, 70, or at least 71 after 120 minutes of incubation at pH 3.0 in the presence of pepsin.

In still further particular embodiments, the lipase of the invention has a % residual activity, determined as described above and in Example 4, of at least 8, 10, 12, 14, 16, 18, 20, 22, 24, 26, 28, 30, 32, 34, 36, 38, 40, 42, 44, 46, 48, or 50 after 15 minutes of incubation at pH 3.0 in the presence of bile salt.

Particular examples of lipase variants of an improved stability at pH 3.0 are (relative to the lipase having the sequence of amino acids 1-269 of SEQ ID NO: 2): LV2934, LVA043, LVA049, LV1855, LV1865, LV1874, LV1889, LV1857, LVA012, LVA023, LVA041, LVA061, and LVA099. Particularly preferred lipases having an improved stability at pH 3.0 in the presence of pepsin are the following: LVA043, LV1855, LV1865, LV1874, LV1889, LV1857, LVA012, and LVA099. Further examples of lipases having an improved stability at pH 3.0 in the presence of pepsin are the following: LVA147, LVA315, LVA317, LVA319, and LVA714. These are improved as compared to either of the lipases of SEQ ID NO: 2, SEQ ID NO: 1, and LV2934. Another particularly preferred lipase variant which has an improved stability at pH 3.0 in the presence of bile salts is LVA349. See Table 1 and Example 4 for the structure of these lipase variants.

In another particular embodiment, which may be particularly useful for less purified lipase preparations, e.g. for screening purposes, the stability at pH 3.0 is measured as follows: First the enzyme is pre-incubated for 3 hours at pH 3.0 and room temperature in the presence of 75 ug/mL pepsin, and then the residual lipase activity is measured in a rate assay monitoring activity over time. In preferred embodiments, i) the substrate for the residual activity assay is 4-nitrophenol palmitate, preferably 1 mM PNP-Palmitate, 1.2% Triton-X100, 4 mM $CaCl_2$, 100 mM TRIS, pH 8.0; ii) for the residual activity assay, $OD_{405}$ readings are taken from 15 minutes after substrate addition and until 18 hours after substrate addition; iii) $OD_{405}$ readings are expressed as mOD (milli OD) per hour; iv) data that falls in the linear range are collected and the residual lipase activity of each pepsin-treated sample compared with the residual lipase activity of the corresponding untreated sample; v) % residual activity (% RA) is calculated by dividing the rate of the treated condition by the rate of the untreated condition and multiplying the result by 100. See Example 8 for more details. The following variants have an improved stability at pH 3.0 in the presence of pepsin, as compared to the lipase having the sequence of amino acids 1-269 of SEQ ID NO: 2: The lipase having amino acids 1-269 of SEQ ID NO: 1, LVAR0002b, LVAR0003, LVAR0011a, LVAR0013, LVAR0014, LVAR0015, LVAR0016, LVAR0017, LVAR0045, LVAR0046, LVAR0047, LVAR0048, LVAR0050, LVAR0051, LVAR0052, LVAR0053, LVAR0054, LVAR0055, LVAR0056, LVAR0057, LVAR0058, LVAR0059, LVAR0061, LVAR0062, LVAR0063, LVAR0064, LVAR0065, LVAR0066, LVAR0067, LVAR0068, LVAR0069, LVAR0070, LVAR0071, LVAR0072, LVAR0101, LVAR0102, and LVAR0106. Preferred variants are: LVAR0011a, LVAR0013, LVAR0017, LVAR0046, LVAR0052, LVAR0055, LVAR0061, LVAR0063, LVAR0068, LVAR0070, LVAR0071, LVAR0072, LVAR0014, LVAR0015, LVAR0057, LVAR0101, LVAR0102, and LVAR0106. Particularly preferred lipase variants are: LVAR0014, LVAR0015, LVAR0057, LVAR0101, LVAR0102, and LVAR0106. The structure of these variants is shown in Tables 6 and 9.

In another particular embodiment, the lipase of the invention is stable in the presence of pepsin, e.g. in the presence of 70 mg/ml pepsin, preferably for 15, 45, 60, and/or 120 minutes at a desired pH (e.g. pH 2.5, 3.0, 3.5, 4.0, 4.5, 5.0, 5.5, or 6.0) and 37° C. For more details, see the above section addressing Example 4.

In a still further particular embodiment, the lipase of the invention is stable in the presence of bile salts, e.g. in the presence of 10 mM bile salts, preferably for 15, 45, and/or 120 minutes at a desired pH (e.g. pH 2.5, 3.0, 3.5, 4.0, 4.5, 5.0, 5.5, or 6.0) and 37° C. For more details, see the above section addressing Example 4.

In a still further particular embodiment, the lipase of the invention has an improved phospholipase activity, as compared to a reference lipase such as the lipase having the sequence of amino acids 1-269 of SEQ ID NO: 2, or the lipase having the sequence of amino acids 1-269 of SEQ ID NO: 1. The phospholipase activity may be determined as follows: i) the purified enzyme is diluted in enzyme dilution buffer (20 mM Na-Acetate, 0.01% w/w Triton-X100, pH 5.0) to 5 mgEP/ml, e.g. based on $A_{280}$; ii) the activity on 1-myristoyl-2-palmitoyl-sn-glycero-3-phosphocholine is determined, preferably at 40° C. and for 20 minutes; iii) the liberated free fatty acids are determined and quantified by MALDI-TOF MS, preferably after mixture with 20 mg/mL 2,5-dihydrobenzoic acid in 50% MeOH, 0.1% TFA (matrix); iii) the relative signal intensities (area under each peak) of the MS peaks are used for the calculation of the distribution between Phospholipase A1 and A2 activity.

Lipases with an improved % undigested phospholipid left after hydrolysis as compared to a reference lipase such as the lipase having amino acids 1-269 of SEQ ID NO: 2, or the lipase having amino acids 1-269 of SEQ ID NO: 1, have an improve phospholipase activity.

Particular examples of lipase variants with improved phospholipase activity as compared to SEQ ID NO: 2 are the following: LV1889, LVA023, LV1330, LV1855, LV1865, LV1874, LV1889, LVA043, LVA049, LV1857, and LV1232. Preferred lipases are LV1232 and LV1889.

In a still further particular embodiment, the lipase of the invention has an improved performance in an in vitro digestion model as compared to the lipase having amino acids 1-269 of SEQ ID NO: 2, the lipase having amino acids 1-269 of SEQ ID NO: 1, and/or as compared to LV2934 (the deglycosylated variant N33Q of SEQ ID NO: 1). The in vitro model makes use of Diet I, or Diet II, which are described in the Experimental part. In brief, 100 ul of diet is mixed with 20 ul pepsin (700 mg/ml) and 30 ul lipase (duplicate of 4 concentrations) in the well of a microtiter plate, which is incubated for 1 hour at 37° C. with shaking (750 rpm) before adding 25 ul buffer (0.8 M MES (2-[N-morpholino]ethanesulfonic acid), 0.8 M sodium acetate, 0.8 M imidazole, pH 7.0) and 20 ul bile salts (100 mM) resulting in a pH of 5.7 to 6.0. The plate is then incubated 2 hours at 37° C. with agitation before stopping the reaction by adding 50 ul 10% Triton-X100 in 1 M phosphoric acid. After diluting 125-250 times in 1% Triton-X100 the amount of free fatty acids is determined using a colorimetric kit, such as the NEFA C kit, as described in Example 3.

Examples of lipases of an improved performance in vitro are: LVAR0003, LVAR0045, LVAR0046, LVAR0047, LVAR0050, LVAR0051, LVAR0052, LVAR0053, LVAR0054, LVAR0056, LVAR0057, LVAR0061, LVAR0062, LVAR0063, LVAR0064, LVAR0065, LVAR0067, LVAR0069, and LVAR0072. Other examples are: LVAR0074, LVAR0076, LVAR0077, LVAR0078, LVAR0079, LVAR0080, LVAR0086, LVAR0088, LVAR0091, LVAR0094, LVAR0095, LVAR0096, LVAR0099, LVAR0101, LVAR0102, LVAR0103, LVAR0104, LVAR0106, and LVAR0108. Preferred examples are: LVAR0003, LVAR0013, LVAR0032, LVAR0050, LVAR0058, and LVAR0069. More preferred are: LVAR0063, LVAR0067, LVAR0069, LVAR0079, LVAR0080, LVAR0094, LVAR0095, LVAR0096, LVAR0099, LVAR0101, LVAR0102, LVAR0103, LVAR0104, LVAR0106, and LVAR0108. Most preferred are LVAR0094, LVAR0099, LVAR0095, and LVAR0106.

In a still further particular embodiment, the lipase of the invention has an improved performance in vivo. The in vivo performance may be estimated in a lipase screening test in female Göttingen minipigs (Ellegaard) with induced Pancreatic Exocrine Insufficiency (PEI), as described in Example 10, and/or in a full in vivo digestibility trial as described in Example 11. The performance may be improved relative to the lipase having amino acids 1-269 of SEQ ID NO: 2, the lipase having amino acids 1-269 of SEQ ID NO: 1, and/or LV2934 being deglycosylated variant N33Q of the lipase having amino acids 1-269 of SEQ ID NO: 1. For more details of this test, please see Example 10.

The lipase of the invention preferably comprises at least one of the following substitutions: N26I, D27Q, D27R, D27Y, P29T, A30T, A30V, T321, N33Q, N33T, N33Y, P42L, E43D, E43K, E43M, E43V, A49T, L69I, E87K, E99D, E99K, E99P, E99S, E99T, G163K, S216P, L227G, T231R, N233R, D234K, E239V.

The lipase of the invention preferably comprises at least one of the following substitutions: N26I, D27Q, D27R, D27Y, P29T, A30T, A30V, T32I, N33Q, N33T, N33Y, P42L, E43D, E43K, E43M, E43V, A49T, E56C, E56S, D57A, D57G, D57N, V60L, L69I, E87K, G91A, G91E, G91N, G91R, G91S, G91T, G91V, G91W, L93F, N94K, N94R, N94S, D96E, D96G, D96L, D96N, D96S, D96V, D96W, D96Y, L97M, L97Q, K981, E99D, E99K, E99P, E99S, E99T, D111A, D111S, T114I, L147S, G163K, E210D, S216P, L227G, T231R, N233R, D234K, E239V, Q249R, N251S, D254N, P256T, G263Q, L264A, I265T, G266D, T267A, and/or L269N.

In a particular embodiment, the lipase of the invention is not: (i) the lipase having amino acids 1-269 of SEQ ID NO: 1; (ii) variant N33Q of the lipase of (i); (iii) amino acids −5-269 (−5 to +269), −4-269 (−4 to +269), −3-269 (−3 to +269), −2-269 (−2 to +269), −1-269 (−1 to +269), and 2-269 of SEQ ID NO: 1; (iv) variant N33Q of any one of the sequences of (iii); any one of embodiments (i), (ii), (iii), and/or (iv) with an amino-terminal methionine residue, (v) any one of embodiments (i), (ii), (iii), (iv), and/or (v) with a polyhistidine tract; (vi) any one of embodiments (i), (ii), (iii), (iv), (v) and/or (vi) with at least one conservative substitution as defined on p. 5, lines 4-18 of WO 2006/136159; (vii) a fragment of any one of the previous embodiments as defined on p. 6, lines 4-14 of WO 2006/136159; (iix) a specific mixture of variants as defined on p. 6, line 34 to p. 7, line 11 of WO 2006/136159; and/or not (ix) a lipase specifically disclosed for pharmaceutical use in WO 2006/136159.

Particularly preferred lipases of the invention are: LV1232, LV1855, LV1857, LV1865, LV1874, and LV1889.

Other particularly preferred lipases of the invention are the following lipases, which are variants of a parent lipase, and comprise (T231R+N233R) and in addition at least one of the following substitutions: N26I, D27Q, D27R, D27Y, A30V, T32I, N33Y, P42L, E43K, E43M, E43V, A49T, E56A, E56C, E56K, E56R, E56S, D57A, D57G, D57N, E87K, G91E, G91N, G91R, G91V, G91W, L93F, N94K, N94R, D96G, D96L, D96N, D96S, D96V, D96W, D96Y, L97M, L97Q, K98I, E99K, E99P, E99S, E99T, D111A, D111S, T114I, L147S, G163K, S216P, L227G, D234K, E239V, Q249R, D254N, G2630, L264A, 1265T, G266D, and/or L269N.

Ligase, Protease, Amylase

The following ligases are also included within the scope of the present invention: Any one of the lipases claimed and disclosed herein, comprising in addition any one of the following N-terminal extensions: SPIRR, PIRR, IRR, RR, and R, corresponding to amino acids −5 to −1 of SEQ ID NO: 2, −4 to −1 of SEQ ID NO: 2, −3 to −1 of SEQ ID NO: 2, −2 to −1 of SEQ ID NO: 2, and −1 of SEQ ID NO: 2, respectively. Also any mixture of any of these N-terminal versions is specifically included herein.

In a particular embodiment, the specific activity of the lipase of the invention is at least 50% of the specific activity of the lipase having amino acids 1-269 of SEQ ID NO: 2. In additional particular embodiments, the specific activity of the variant lipase is at least 60, 70, 75, 80, 85, 90, or at least 95% of the specific activity of the lipase having amino acids 1-269 of SEQ ID NO: 2. The specific activity may be measured using any of the lipase assays of Example 1 herein, but is preferably measured in LU/mg enzyme protein using the LU-assay of Example 1, and determining enzyme protein content, e.g. as described in Example 2 ($A_{280}$ and GPMAW), or using amino acid analysis. In an amino acid analysis, the peptide bonds of the lipase sample are subjected to acid hydrolysis, followed by separation and quantification of the released amino acids, e.g. on a Biochrom 20 Plus Amino Acid Analyser, commercially available from Bie & Berntsen A/S, Sandbaekvej 5-7, DK-2610 Roedovre, Denmark, according to the manufacturer's instructions. The amount of each individual amino acid is determined by reaction with ninhydrin.

In still further particular embodiments, the lipase of the invention is used in combination with an additional lipase. Examples of additional lipases are mammalian lipases, and microbial lipases. A preferred mammalian lipase is pancreas extract, e.g. from swine or ox, such as pancreatin. The pancreatin may be used in the form of an uncoated (raw) product, or in the form of a formulated product (enteric coated (to provide resistance against gastric acid), or non-functionally coated (coated, but not to provide resistance against gastric acid)). Pancreatin potentially comprises still further enzymatic active constituents like pancreatic protease and/or pancreatic amylase. The microbial lipase may be, e.g., based on or derived from a bacterial or fungal lipase. Bacterial lipases can be derived from, e.g., *Bacillus* or *Pseudomonas*, fungal lipases can be derived from, e.g., strains of *Rhizopus, Candida*, or *Humicola*, such as *Rhizopus delemar, Rhizopus javanicus, Rhizopus oryzae*, or *Humicola lanuginosa*, in particular either of the products Lipase D2™ or Lipase D Amano 2000™ (lipase, EC 3.1.1.3) which are commercially available from Amano Pharmaceuticals, Japan.

The lipase of the invention may be used in combination with a protease, with or without an amylase as described below. The term "protease" is defined herein as an enzyme that hydrolyses peptide bonds. It includes any enzyme belonging to the EC 3.4 enzyme group (including each of the thirteen subclasses thereof, these enzymes being in the following referred to as "belonging to the EC 3.4.-.- group").

Examples of proteases are mammalian proteases, and microbial proteases. A preferred mammalian protease is pancreas extract, e.g. from swine or ox, such as pancreatin. The pancreatin may be used in the form of an uncoated (raw) product, or in the form of a formulated product (enteric coated, or non-functionally coated). Pancreatin potentially comprises still further enzymatic active constituents like pancreatic lipase, BSSL (Bile Salt Stimulated Lipase), and/or pancreatic amylase.

The microbial protease may be, e.g., based on or derived from bacterial or fungal strains. The protease may in particular be derived from a strain of Aspergillus, such as *Aspergillus oryzae* or *Aspergillus melleus*, in particular the product Prozyme 6™ (neutral, alkaline protease EC 3.4.21.63) which is commercially available from Amano Pharmaceuticals, Japan. Examples of bacterial proteases are proteases from *Bacillus* and *Nocardiopsis*, such as the *Bacillus licheniformis* protease having the amino acid sequence of amino acids 1-274 of SEQ ID NO: 3, the *Nocardiopsis* sp. protease having the amino acid sequence of amino acids 1-188 of SEQ ID NO: 4, or the *Nocardiopsis dassonviellei* subsp. *dassonvillei* protease having the amino acid sequence of amino acids 1-188 of SEQ ID NO: 5. The protease of amino acids 1-274 of SEQ ID NO: 3 may, e.g., be prepared as described in WO 2006/136160. The proteases of amino acids 1-188 of SEQ ID NO: 4-5 may, e.g., be prepared as described in WO 2001/58276, or in WO 2004/111224.

In a preferred embodiment, the protease of the invention is at least 70% identical to a protease having, or comprising, either of (i) amino acids 1-274 of SEQ ID NO: 3, (ii) amino acids 1-188 of SEQ ID NO: 4, and/or (iii) amino acids 1-188 of SEQ ID NO: 5. In additional preferred embodiments of either of (i), (ii) or (iii), the degrees of identity is at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments of either of (i), (ii), or (iii), the degrees of identity is at least about 50%, 51%, 52%, 53%, 54%, 55%, 56%, 57%, 58%, 59%, 60%, 61%, 62%, 63%, 64%, 65%, 66%, 67%, 68%, or at least 69%.

The lipase of the invention, with or without a protease as described above, may also be used in combination with an amylase.

In the present context, an amylase is an enzyme that catalyzes the endo-hydrolysis of starch and other linear and branched oligo- and polysaccharides. The amylose part of starch is rich in 1,4-alpha-glucosidic linkages, while the amylopectin part is more branched containing not only 1,4-alpha- but also 1,6-alpha-glucosidic linkages. In a particular embodiment, the amylase is an enzyme belonging to the EC 3.2.1.1 group.

In particular embodiments, the amylase is a mammalian amylase or a microbial amylase. An example of a mammalian amylase is pancreas extract, e.g. from swine or ox, such as pancreatin. The pancreatin may be used in the form of an uncoated (raw) product, or in the form of a formulated product (enteric coated, or non-functionally coated). Pancreatin potentially comprises still further enzymatic active constituents like pancreatic protease and/or pancreatic lipase. The microbial amylase may be, e.g., based on or derived from bacterial or fungal strains, such as *Bacillus, Pseudomonas, Aspergillus*, or *Rhizopus*.

The amylase may in particular be derived from a strain of *Aspergillus*, such as *Aspergillus niger, Aspergillus oryzae* or *Aspergillus melleus*, for example either of the products Amylase A1™ derived from *Aspergillus oryzae* which is commercially available from Amano Pharmaceuticals, Japan, or Amylase EC™ derived from *Aspergillus melleus* which is commercially available from Extract-Chemie, Germany.

Preferred amylases are (i) an amylase comprising amino acids 1-481 of SEQ ID NO: 6 (such as amino acids 1-481, 1-484, or 1-486 thereof), amino acids 1-481 of SEQ ID NO: 7, and/or amino acids 1-483 of SEQ ID NO: 8. In a preferred embodiment, the amylase is an amylase having, or comprising an amino acid sequence being, at least 70% identical to either of (i) amino acids 1-481 of SEQ ID NO: 6, (ii) amino acids 1-481 of SEQ ID NO: 7, and/or (iii) amino acids 1-483 of SEQ ID NO: 8. The amylases of SEQ ID NOs: 6-8 may, e.g., be prepared as described in co-pending WO 2006/136161. In additional preferred embodiments of either of (i), (ii), or (iii), the degrees of identity are at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments of either of (i), (ii), or (iii), the degrees of identity are at least 50%, 51%, 52%, 53%, 54%, 55%, 56%, 57%, 58%, 59%, 60%, 61%, 62%, 63%, 64%, 65%, 66%, 67%, 68%, or at least 69%.

Generally, the lipase, protease, and amylase enzymes (hereinafter "the enzyme(s)," viz. the enzymes of the invention) may be natural or wild-type enzymes (obtained from animals, in particular mammals, for example human or swine enzymes; from plants, or from microorganisms), but also any mutants, variants, fragments etc. thereof exhibiting the desired enzyme activity, as well as synthetic enzymes, such as shuffled, hybrid, or chimeric enzymes, and consensus enzymes.

In a specific embodiment, the enzyme(s) are low-allergenic variants, designed to invoke a reduced immunological response when exposed to animals, including man. The term immunological response is to be understood as any reaction by the immune system of an animal exposed to the enzyme(s). One type of immunological response is an allergic response leading to increased levels of IgE in the exposed animal. Low-allergenic variants may be prepared using techniques known in the art. For example the enzyme(s) may be conjugated with polymer moieties shielding portions or epitopes of the enzyme(s) involved in an immunological response. Conjugation with polymers may involve in vitro chemical coupling of polymer to the enzyme(s), e.g. as described in WO 96/17929, WO 98/30682, WO 98/35026, and/or WO 99/00489. Conjugation may in addition or alternatively thereto involve in vivo coupling of polymers to the enzyme(s). Such conjugation may be achieved by genetic engineering of the nucleotide sequence encoding the enzyme(s), inserting consensus sequences encoding additional glycosylation sites in the enzyme(s) and expressing the enzyme(s) in a host capable of glycosylating the enzyme(s), see, e.g., WO 00/26354. Another way of providing low-allergenic variants is genetic engineering of the nucleotide sequence encoding the enzyme(s) so as to cause the enzymes to self-oligomerize, effecting that enzyme monomers may shield the epitopes of other enzyme monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the enzyme(s) by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

In particular embodiments, the enzyme(s) are (i) stable at pH 2-8, preferably also at pH 3-7, more preferably at pH 4-6; (ii) active at pH 4-9, preferably 4-8; (iii) stable against degradation by pepsin and other digestive proteases (such as pancreas proteases, i.e., mainly trypsin and chymotrypsin); and/or (iv) stable and/or active in the presence of bile salts.

The term "in combination with" refers to the combined use according to the invention of the lipase, protease and/or amylase. The combined use can be simultaneous, overlapping, or sequential, these three terms being generally interpreted in the light of the prescription made by the physician.

The term "simultaneous" refers to circumstances under which the enzymes are active at the same time, for example when they are administered at the same time as one or more separate pharmaceutical products, or if they are administered in one and the same pharmaceutical composition.

The term "sequential" refers to such instances where one and/or two of the enzymes are acting first, and the second and/or third enzyme subsequently. A sequential action can be obtained by administering the enzymes in question as separate pharmaceutical formulations with desired intervals, or as one pharmaceutical composition in which the enzymes in question are differently formulated (compartmentalized), for example with a view to obtaining a different release time, providing an improved product stability, or to optimizing the enzyme dosage.

The term "overlapping" refers to such instances where the enzyme activity periods are neither completely simultaneous nor completely sequential, viz. there is a certain period in which the enzymes are both, or all, active.

The term "a", for example when used in the context of the protease, lipase, and/or amylase of the invention, means at least one. In particular embodiments, "a" means "one or more," or "at least one", which again means one, two, three, four, five etc.

The activity of the enzyme(s) of the invention can be measured using any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 4, 5, 6, 7, or 8, and temperatures of 30, 35, 37, or 40° C.

Examples of suitable enzyme assays are included in the experimental part. Other examples are the FIP or Ph.Eur. assays for protease and amylase activity. These assays are, e.g., described in co-pending applications WO 2006/136160 and WO 2006/136161, respectively.

Medicament

In the present context, the term "medicament" means a compound, or mixture of compounds, that treats, prevents and/or alleviates the symptoms of disease, preferably treats and/or alleviates the symptoms of disease. The medicament may be prescribed by a physician, or it may be an over-the-counter product.

Pharmaceutical Compositions

Isolation, purification, and concentration of the enzyme(s) of the invention may be carried out by conventional means. For example, they may be recovered from a fermentation broth by conventional procedures including, but not limited to, centrifugation, filtration, extraction, spray-drying, evaporation, or precipitation, and further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulphate precipitation), SDS-PAGE, or extraction (see, e.g., Protein Purification, J.-C. Janson and Lars Ryden, editors, VCH Publishers, New York, 1989).

For example, a variant of the lipase of SEQ ID NO: 2 such as the lipase of SEQ ID NO: 1 may, e.g., be prepared on the basis of U.S. Pat. No. 5,869,438 (in which SEQ ID NO: 1 is a DNA sequence encoding the lipase of SEQ ID NO: 2 herein), viz. by recombinant expression in a suitable host cell of a DNA sequence which is a modification of SEQ ID NO: 1 of the US patent, the modification reflecting the amino acid differences between SEQ ID NO: 1 and 2 herein. Such modifications can be made by site-directed mutagenesis, as is known in the art.

In a particular embodiment, concentrated solid or liquid preparations of each of the enzyme(s) are prepared separately. These concentrates may also, at least in part, be separately formulated, as explained in more detail below.

In a further particular embodiment, the enzyme(s) are incorporated in the pharmaceutical compositions of the invention in the form of solid concentrates. The enzyme(s) can be brought into the solid state by various methods as is known in the art. For example, the solid state can be either crystalline, where the enzyme molecules are arranged in a highly ordered form, or a precipitate, where the enzyme molecules are arranged in a less ordered, or disordered, form.

Crystallization may, for example, be carried out at a pH close to the pI of the enzyme(s) and at low conductivity, for example 10 mS/cm or less, as described in EP 691982. In a particular embodiment, the lipase for use according to the invention is a crystalline lipase, which can be prepared as described in Example 1 of EP 600868 B1. The lipase crystals may furthermore be cross-linked as described in WO 2006/044529.

Various precipitation methods are known in the art, including precipitation with salts, such as ammonium sulphate, and/or sodium sulphate; with organic solvents, such as ethanol, and/or isopropanol; or with polymers, such as PEG (Poly Ethylene Glycol). In the alternative, the enzyme(s) can be precipitated from a solution by removing the solvent (typically water) by various methods known in the art, e.g. lyophilization, evaporation (for example at reduced pressure), and/or spray drying.

In a further particular embodiment, the solid concentrate of the enzyme(s) has a content of active enzyme protein of at least 50% (w/w) by reference to the total protein content of the solid concentrate. In still further particular embodiments, the content of active enzyme protein, relative to the total protein content of the solid concentrate is at least 55, 60, 65, 70, 75, 80, 85, 90, or at least 95% (w/w). The protein content can be measured as is known in the art, for example by densitometer scanning of coomassie-stained SDS-PAGE gels, e.g. using a GS-800 calibrated densitometer from BIO-RAD; by using a commercial kit, such as Protein Assay ESL, order no. 1767003, which is commercially available from Roche; or on the basis of the method described in Example 8 of WO 01/58276.

Preferably, the enzyme protein (e.g., lipase enzyme protein) constitutes at least 50%, more preferably at least 55, 60, 65, 70, 75, 80, 85, 90, 92, 94, 95, 96, or at least 97% of the protein spectrum of the solid enzyme concentrate for use according to the invention, as measured by densitometer scanning of a coomassie-stained SDS-PAGE gel. Such enzymes may be designated "isolated", "purified", or "purified and isolated" enzymes or polypeptides. For the lipase expressed in Aspergillus and comprising a mixture of various N-terminal forms as explained in Example 5 of WO 2006/136159, the relevant band on an SDS-PAGE gel is located corresponding to a molecular weight of 34-40 kDa. For a non-glycosylated variant such as N33Q of SEQ ID NO: 1 (LV2934), the relevant band is located at around 30 kDa.

A pharmaceutical composition of the invention comprises the enzyme(s), preferably in the form of concentrated enzyme preparations, more preferably solid concentrates, together with at least one pharmaceutically acceptable auxiliary, or subsidiary, material such as (i) at least one carrier and/or excipient; or (ii) at least one carrier, excipient, diluent, and/or adjuvant. Non-limiting examples of, optional, other ingredients, all pharmaceutically acceptable, are disintegrators, lubricants, buffering agents, moisturizing agents, preservatives, flavouring agents, solvents, solubilizing agents, suspending agents, emulsifiers, stabilizers, propellants, and vehicles.

Generally, depending i.a. on the medical indication in question, the composition of the invention may be designed for all manners of administration known in the art, preferably including enteral administration (through the alimentary canal). Thus, the composition may be in solid, semi-solid, liquid, or gaseous form, such as tablets, capsules, powders, granules, microspheres, ointments, creams, foams, solutions, suppositories, injections, inhalants, gels, lotions, and aerosols. The medical practitioner will know to select the most suitable route of administration and of course avoid potentially dangerous or otherwise disadvantageous administration routes.

The following methods and auxiliary materials are therefore also merely exemplary and are in no way limiting.

For solid oral preparations, the enzyme(s) can be used alone or in combination with appropriate additives to make pellets, micropellets, tablets, microtablets, powders, granules or capsules, for example, with conventional carriers, such as lactose, mannitol, corn starch, or potato starch; with excipients or binders, such as crystalline, or microcrystalline, cellulose, cellulose derivatives, acacia, corn starch, or gelatins; with disintegrators, such as corn starch, potato starch, or sodium carboxymethylcellulose; with lubricants, such as carnauba wax, white wax, shellac, waterless colloid silica, polyethylene glycol (PEGs, also known under the term macrogol) from 1500 to 20000, in particular PEG4000, PEG6000, PEG 8000, povidone, talc, monolein, or magnesium stearate; and if desired, with diluents, adjuvants, buffering agents, moistening agents, preservatives such as methylparahydroxybenzoate (E218), colouring agents such as titanium dioxide (E171), and flavouring agents such as saccharose, saccharin, orange oil, lemon oil, and vanillin. Oral preparations are examples of preferred preparations for treatment of the medical indication of PEI.

The enzyme(s) can also, quite generally, be formulated into liquid oral preparations, by dissolving, suspending, or emulsifying them in an aqueous solvent such as water, or in non-aqueous solvents such as vegetable or other similar oils, synthetic aliphatic acid glycerides, esters of higher aliphatic acids, propylene glycol, polyethylene glycol such as PEG4000, or lower alcohols such as linear or ramified C1-C4 alcohols, for example 2-propanol; and if desired, with conventional subsidiary materials or additives such as solubilizers, adjuvants, diluents, isotonic agents, suspending agents, emulsifying agents, stabilizers, and preservatives.

Furthermore, the enzyme(s) can generally be made into suppositories for rectal administration by mixing with a variety of bases such as emulsifying bases or water-soluble bases. The suppository can include vehicles such as cocoa butter, carbowaxes and polyethylene glycols, which melt at body temperature, yet are solidified at room temperature.

The use of liposomes as a delivery vehicle is another method of possible general interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will normally be neutral or acidic lipids, such as cholesterol, phosphatidyl serine, phosphatidyl glycerol, and the like. For preparing the liposomes, the procedure described by Kato et al., 1991, *J. Biol. Chem.* 266:3361 may be used.

Unit dosage forms for oral or rectal administration such as syrups, elixirs, powders, and suspensions may be provided wherein each dosage unit, for example, teaspoonful, tablespoonful, capsule, tablet or suppository, contains a predetermined amount of the enzyme(s). Similarly, unit dosage forms for injection or intravenous administration may comprise the enzyme(s) in a composition as a solution in sterile water, normal saline, or another pharmaceutically acceptable carrier.

The term "unit dosage form", as used herein, refers to physically discrete units suitable as unitary dosages for human and animal subjects, each unit containing a predetermined quantity of enzyme(s) in an amount sufficient to produce the desired effect.

In a particular embodiment, the pharmaceutical composition of the invention is for enteral, preferably oral, administration.

In further particular embodiments, the oral composition is (i) a liquid composition containing crystals of the enzyme(s); (ii) a liquid suspension of sediments of (highly) purified enzyme(s); (iii) a gel containing the enzyme(s) in solid or solubilized form; (iv) a liquid suspension of immobilized enzyme(s) or of enzymes adsorbed to particles and the like; or (v) a solid composition in the form of enzyme(s)-containing powder, pellets, granules, or microspheres, if desired in the form of tablets, capsules, or the like, that are optionally coated, for example with an acid-stable coating.

In another particular embodiment of the composition, the enzyme(s) are compartmentalized, viz. separated from each other, for example by means of separate coatings.

In a still further particular embodiment of the composition, the protease is separated from other enzyme components of the composition, such as the lipase, and/or the amylase.

The dosage of the enzyme(s) will vary widely, depending on the specific enzyme(s) to be administered, the frequency of administration, the manner of administration, the severity of the symptoms, and the susceptibility of the subject to side effects, and the like. Some of the specific enzymes may be more potent than others.

Examples of solid oral preparations of the enzyme(s) of the invention comprise: (i) a lipase of the invention; (ii) a protease having at least 70% identity to a protease selected from the group consisting of a) a protease having amino acids 1-274 of SEQ ID NO: 3, b) a protease having amino acids 1-188 of SEQ ID NO: 4, and c) a protease having amino acids 1-188 of SEQ ID NO: 5; and/or (iii) an amylase having at least 70% identity to an amylase selected from the group consisting of a) an amylase having amino acids 1-481 of SEQ ID NO: 6, b) an amylase having amino acids 1-481 of SEQ ID NO: 7, and c) an amylase having amino acids 1-483 of SEQ ID NO: 8; wherein preferably the anticipated daily clinical dosages of the enzymes of (i), (ii), and (iii) are as follows (all in mg enzyme protein per kg of bodyweight (bw)): For the lipase of (i): 0.01-1000, 0.05-500, 0.1-250, or 0.5-100 mg/kg bw; for the amylase of (ii): 0.001-250, 0.005-100, 0.01-50, or 0.05-10 mg/kg bw; for the protease of (iii): 0.005-500, 0.01-250, 0.05-100, or 0.1-50 mg/kg bw.

A preferred example of solid oral preparations of the enzyme(s) of the invention comprise: (i) a lipase of the invention, and (ii) an amylase comprising amino acids 1-481 of SEQ ID NO: 6, and/or (iii) a protease comprising, preferably having, amino acids 1-274 of SEQ ID NO: 3.

Examples of anticipated daily clinical dosages of the enzymes of (i), (ii), and (iii) are as follows (all in mg enzyme protein per kg of bodyweight (bw)): For the lipase of (i): 0.1-250, 0.5-100, or 1-50 mg/kg bw; for the amylase of (ii): 0.01-50, 0.05-10, or 0.1-5 mg/kg bw; for the protease of (iii): 0.05-100, 0.1-50, or 0.5-25 mg/kg bw.

The amide (peptide) bonds, as well as the amino and carboxy termini, may be modified for greater stability on oral administration. For example, the carboxy terminus may be amidated.

Particular embodiments of pharmaceutical compositions of the invention, suitable for the treatment of digestive disorders, PEI, pancreatitis, cystic fibrosis, diabetes type I, and/or diabetes type II, may be prepared by incorporating the enzyme(s) of the invention into pellets. The pellets may generally comprise from 10-90% (w/w, relative to the dry weight of the resulting pellets) of a physiologically acceptable organic polymer, from 10-90% (w/w, relative to the dry weight of the resulting pellets) of cellulose or a cellulose derivative, and from 80-20% (w/w, relative to the dry weight of the resulting pellets) of the enzyme(s), the total amount of organic polymer, cellulose or cellulose derivative and enzyme(s) making up to 100% in each case.

The physiologically acceptable organic polymer can be selected from the group consisting of polyethylene glycol 1500, polyethylene glycol 2000, polyethylene glycol 3000, polyethylene glycol 4000, polyethylene glycol 6000, polyethylene glycol 8000, polyethylene glycol 10000, polyethylene glycol 20000, hydroxypropyl methylcellulose, polyoxyethylene, copolymers of polyoxyethylene-polyoxypropylene and mixtures of said organic polymers. Polyethylene glycol 4000 is preferred as physiologically acceptable organic polymer.

The cellulose or a cellulose derivative can e.g. be selected from cellulose, cellulose acetate, cellulose fatty acid ester, cellulose nitrates, cellulose ether, carboxymethyl cellulose, ethyl cellulose, hydroxyethyl cellulose, hydroxypropyl cellulose, methyl cellulose, methyl ethylcellulose and methylhydroxypropyl cellulose. Cellulose, in particular microcrystalline cellulose is preferred as cellulose or cellulose derivative.

The resulting pellets may be coated with a suitable enteric coating, other non functional coating or be used directly without such coating. Further, the resulting pellets may be filled in capsules like hard gelatin capsules or gelatin free capsules of a suitable size for therapy of a disorder or disease as described in more detail above. In an embodiment of the invention, pellets produced from different enzyme types, in particular from lipase, protease and/or amylase may be filled into said capsules. While filling the capsules with the different enzyme types, the dosing of the single enzyme types (viz. lipase, protease or amylase) may be adapted to specific needs of a certain indication group or a certain patient subgroup by adding a specified amount of any of lipase, protease and/or amylase to the capsules, i.e., capsules may be produced which vary in their specific ratios of lipase:protease:amylase.

Preferred pharmaceutical compositions of the lipase of the invention are described in WO 2005/092370, in particular formulations comprising the preferred exhibients mentioned therein. In a particularly preferred embodiment, the pharmaceutical composition comprises a macrogolglyceride mixture of mono-, di- and tri-acylglycerides and polyethylene glycol (PEG) mono- and di-esters of aliphatic C6-C22 carboxylic acids, and also possibly small proportions of glycerol and free polyethylene glycol.

The polyethylene glycol (PEG) contained in the macrogolglyceride mixtures is preferably PEG which has on average 6 to at most 40 ethylene oxide units per molecule or a molecular weight of between 200 and 2000.

One further aspect of the invention provides for the pharmaceutical composition of the enzyme(s) of the invention to comprise a system consisting of surfactant, co-surfactant and lipophilic phase, the system having an LVB value (Hydrophilic-Lipophilic Balance) greater than or equal to 10 and a melting point greater than or equal to 30° C. In a preferred embodiment, the system has an LVB value of 10 to 16, preferably of 12 to 15, and has a melting point of between 30 and 600° C., preferably between 40 and 500° C. In particular, the system characterised by LVB value and melting point is a mixture of mono-, di- and triacylgylcerides and mono- and diesters of polyethylene glycol (PEG) with aliphatic carboxylic acids with 8 to 20, preferably 8 to 18, carbon atoms, whereby the polyethylene glycol preferably has about 6 to about 32 ethylene oxide units per molecule, and the system optionally contains free glycerin and/or free polyethylene glycol. The LVB value of such a system is preferably regulated by the chain length of the PEG. The melting point of such a system is regulated by the chain length of the fatty acids, the chain length of the PEG and the degree of saturation of the fatty-acid chains, and hence the starting oil for the preparation of the macrogolglyceride mixture.

"Aliphatic C8-C18 carboxylic acids" designates mixtures in which caprylic acid (C8), capric acid (C10), lauric acid (C12), myristic acid (C14), palmitic acid (C16) and stearic acid (C18) are contained in a significant and variable proportion, if these acids are saturated, and the corresponding unsaturated C8-C18 carboxylic acids. The proportions of these fatty acids may vary according to the starting oils.

Such a mixture of mono-, di- and triacylgylcerides and mono- and diesters of polyethylene glycol (PEG) with aliphatic carboxylic acids with 8 to 18 carbon atoms can for example be obtained by a reaction between a polyethylene glycol with a molecular weight of between 200 and 1500 and a starting oil, the starting oil consisting of a triglyceride mixture with fatty acids which are selected from the group containing caprylic acid, capric acid, lauric acid, myristic acid, palmitic acid, stearic acid, oleic acid and linolenic acid, individually or as a mixture. Optionally, the product of such a reaction may also contain small proportions of glycerin and free polyethylene glycol.

Such mixtures are commercially available for example under the trade name Gelucire®. One advantageous embodiment of the invention provides that, of the products known under the trade name Gelucire®, in particular "Gelucire® 50/13" and/or "Gelucire® 44/14" represent suitable mixtures for use in the pharmaceutical preparations according to the invention.

Gelucire® 50/13 is a mixture with mono-, di- and triacylglycerides and mono- and diesters of polyethylene glycol, with palmitic acid (C16) and stearic acid (C18) at 40% to 50% and 48% to 58%, respectively making up the major proportion of bound fatty acids. The proportion of caprylic acid (C8) and capric acid (C10) is less than 3% in each case, and the proportion of lauric acid (C12) and myristic acid (C14) in each case is less than 5%.

Gelucire® 44/14 is a mixture with mono-, di- and triacylgylcerides and mono- and diesters of polyethylene glycol, the respective proportions of palmitic acid (C16) being 4 to 25%, stearic acid (C18) 5 to 35%, caprylic acid (C8) less than 15%, capric acid (C10) less than 12%, lauric acid (C12) 30 to 50% and myristic acid (C14) 5 to 25%. Gelucire® 44/14 can for example be prepared by an alcoholysis/esterification reaction using palm kernel oil and polyethylene glycol 1500.

A preferred embodiment of the present invention provides for a pharmaceutical composition of the enzyme(s) of the invention which comprises a system containing a mixture of mono-, di- and triacyl-glycerides and polyethylene glycol mono- and diesters of aliphatic C8-C18 carboxylic acids and also possibly small proportions of glycerin and free polyethylene glycol, the system having a melting point between 40° C. and 55° C. and an LVB value in the range between 12 and 15. More preferred, the system has a melting point between 44° C. and 50° C. and an LVB value in the range from 13-14. Alternatively, the system has a melting point around 44° C. and an LVB value of 14, or the system has a melting point around 50° C. and an LVB value of 13.

Methods of Treatment

The lipase for use according to the invention, optionally in combination with a protease, and/or an amylase (the enzyme(s) of the invention), is useful in the therapeutic, and/or prophylactic, treatment of various diseases or disorders in animals. The term "animal" includes all animals, and in particular human beings. Examples of animals are non-ruminants, and ruminants, such as sheep, goat, and cattle, e.g. beef cattle, and cow. In a particular embodiment, the animal is a non-ruminant animal. Non-ruminant animals include mono-gastric animals, e.g. horse, pig (including, but not limited to, piglets, growing pigs, and sows); poultry such as turkey, duck and chicken (including but not limited to broiler chicks, layers); young calves; pets such as cat, and dog; and fish (including but not limited to salmon, trout, tilapia, catfish and carps; and crustaceans (including but not limited to shrimps and prawns). In a particular embodiment the animal is a mammal, more in particular a human being.

For example, the enzyme(s) are useful in the treatment of digestive disorders like maldigestion or dyspepsia that are often caused by a deficient production and/or secretion into the gastrointestinal tract of digestive enzymes normally secreted from the stomach, and the pancreas.

Further, the enzyme(s) are particularly useful in the treatment of PEI. PEI can be verified using, i.a., the Borgström test (JOP. J Pancreas (Online), 2002; 3(5):116-125), and it may be caused by diseases and conditions such as pancreatic cancer, pancreatic and/or gastric surgery, e.g. total or partial resection of the pancreas, gastrectomy, post gastrointestinal bypass surgery (e.g. Billroth II gastroenterostomy); chronic pancreatitis; Shwachman Diamond Syndrome; ductal obstruction of the pancreas or common bile duct (e.g. from neoplasm); and/or cystic fibrosis (an inherited disease in which a thick mucus blocks the ducts of the pancreas). The enzyme(s) may also be useful in the treatment of acute pancreatitis.

The effect of the enzyme(s) on digestive disorders can be measured as generally described in EP 0600868, in which Example 2 describes an in vitro digestibility test for measuring lipase stability under gastric conditions, and Example 3 an in vitro digestibility test for lipase activity in the presence of bile salts. Corresponding tests can be set up for the protease and amylase. Also WO 02/060474 discloses suitable tests, for example (1) an in vitro test for measuring lipid digestion in a swine test feed, and (2) an in vivo trial with pancreas insufficient swine in which the digestibility of fat, protein and starch is measured.

As another example, the enzyme(s) are useful in the treatment of Diabetes mellitus type I, and/or type II, in particular for adjuvant treatment in a diabetes therapy of digestive disorders usually accompanying this disease, with a view to diminishing late complications.

The effect on Diabetes mellitus of the enzyme(s) may be determined by one or more of the methods described in WO 00/54799, for example by controlling the level of glycosylated haemoglobin, the blood glucose level, hypoglycemic attacks, the status of fat-soluble vitamins like vitamins A, D and E, the required daily dosage of insulin, the body-weight index, and hyper glycaemic periods.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Particular Embodiments

The invention also relates to a lipase, preferably for use as a medicament, which lipase, as compared to the sequence of amino acids 1-269 of SEQ ID NO:2, comprises the substitutions of any one of claims 1-2 and 5-9, such as substitutions N33Q, T231R, and N233R, as well as at least one additional substitution selected from the following:

E1*,D,N; Q4H,P,R; D5E; N8L,Q; Q9H; F10L; N11C,D,H, L,P,Q,R,S; G23E; N26A,H,I; D27I,N,Q,R,S,V; P29T; A30T,V; T37K,M; G38A,D,F,H,I,K,L,M,N,P,Q,S,T,W,Y; N39H,S; E43K; K46M; A49T; L52I, R; E56K,Q,R,S; D57G,N; V60E,S; G61R; V63R; A68V; L69I; N71I, S; N73Q,Y; I76T; R84E; I86F,L; E87A,H,K,R; I90L,V; G91A,C,E,F,K,L,M,N,S,T,V,W,Y; L93*,F; N94*,K,Q,R, S; F95*; D96*,E,G,N,R,S,W,Y; L97M,Q; K98I,T; E99D; N101Q; D102E,G,Y; R108M; G109A; D111A,E,N,S; G112A; T114I; S115L; W117C,D,E,F,G,H,I,K,L,P,S,T,V, Y; D122E,N; Q126L; V128A; D130H; H135D; P136H; Y138F; V141E,L; A150V; V154F,I,L; A155V; G156R; G161A,E; N162G,S,T; G163A,C,D,E,H,I,K,L,M,N,P,Q, R,S,T,V,W,Y; D167E; V168M; V176A,D,F,G,H,I,K,M,N, Q,T,W; G177A; R179T; L185M; G190C,D; N200Q,S; R205I; L206F; E210D,R,V,Y; S216P; E219D; G225P; T226N; L227F,G; P229R; E239D; G240L; D242E; T244S; G246A; Q249R; N251Q,S; D254A,G,I,K,L,M,N, R,Q,S,Y; I255A,F; P256A,F,G,H,I,L,M,N,Q,S,T,V,W,Y; and L269F,H; said lipase furthermore:

(a) having at least 50% identity to the sequence of amino acids 1 to 269 of SEQ ID NO: 2;

(b) being encoded by a polynucleotide that hybridizes under very low (preferably low, medium, medium-high, high, or most preferably very high) stringency conditions with (i) the coding sequence of SEQ ID NO: 1 of U.S. Pat. No. 5,869,438 which is hereby incorporated by reference (a DNA sequence encoding the lipase of SEQ ID NO: 2 herein), or (ii) a full-length complementary strand of (i); and/or (c) being a variant comprising in addition a substitution, deletion, and/or insertion of one or more (e.g., several) amino acids of the mature polypeptide of SEQ ID NO: 1, preferably of a conservative nature.

Very low to very high stringency conditions are defined as prehybridization and hybridization at 42° C. in 5×SSPE, 0.3% SDS, 200 microg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

Amino acid changes of a conservative nature do not significantly affect the folding and/or activity of the protein, and include small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

The invention furthermore relates to a variant of a parent lipase, preferably for use as a medicament, which variant comprises an alteration at one or more positions, said positions corresponding to one or more positions in the parent enzyme wherein:

(a) the alteration(s) are independently (i) an insertion of an amino acid immediately downstream of the position, (ii) a deletion of the amino acid which occupies the position, and/or (iii) a substitution of the amino acid which occupies the position;

(b) the alterations are selected from the alterations of any one of claims 1-2 and 5-9;

(c) the variant has lipase activity; and (d) each position corresponds to a position of the amino acid sequence of the enzyme having the amino acid sequence of SEQ ID NO: 2.

In a particular embodiment, the variant, and/or the parent has at least 50% identity to the sequence of amino acids 1 to 269 of SEQ ID NO: 2.

The total number of alterations in the variant preferably is twenty-two, twenty-one, twenty, nineteen, eighteen, seventeen, or sixteen. More preferably the total number of alterations is fifteen, even more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one.

A variant may be produced by shuffling one or more polynucleotides encoding one or more homologous parent lipases. The term "shuffling" means recombination of nucleotide sequence(s) between two or more homologous nucleotide sequences resulting in recombined nucleotide sequences (i.e., nucleotide sequences having been subjected to a shuffling cycle) having a number of nucleotides exchanged, in comparison to the starting nucleotide sequence.

The following variants of the lipase of SEQ ID NO: 2 are examples of lipases of claim 6 and 9:

| | |
|---|---|
| LVA012 = LVA013 | D27R + N33Q + G91A + D96E + L97Q + D111A + T231R + N233R + P256T; |
| LVA023 | N33Q + E210D + T231R + N233R; |
| LVA041 | N33Q + D111A + T231R + N233R; |
| LVA043 | N33Q + G91T + T231R + N233R; |
| LVA055 | N33Q + E219D + T231R + N233R; |
| LVA060 | N33Q + W117L + T231R + N233R; |
| LVA061 | D27Q + N33Q + T231R + N233R; |
| LVA063 | N33Q + G91T + T231R + N233R; |
| LVA089 | D27S + N33Q + G91A + D96E + L97Q + D111A + S216P + T231R + N233R + P256T; |
| LVA094 | D27R + N33Q + G91N + N94R + D111A + T231R + N233R + P256T; |
| LVA099 | D27R + N33Q + G91T + N94S + D111A + S216P + L227G + T231R + N233R + P256T; |
| LVA103 | Q4R + N33Q + T231R + N233R; |
| LVA113 | N33Q + T231R + N233R + Q249R; |
| LVA120 | N33Q + D96W + T231R + N233R; |
| LVA129 | D27V + N33Q + V60S + D96W + T231R + N233R + Q249R; |
| LVA130 | D27V + N33Q + V60S + T231R + N233R + Q249R; |
| LVA139 | Q9H + N33Q + D102E + T231R + N233R; |
| LVA140 | N33Q + D111E + T231R + N233R; |
| LVA143 | N33Q + D122E + T231R + N233R; |
| LVA147 | D27R + N33Q + G91N + N94R + D111A + S216P + L227G + T231R + N233R + P256T; |
| LVA162 | N33Q + D167E + T231R + N233R; |
| LVA179 | N33Q + G91N + T231R + N233R; |
| LVA180 | N33Q + T231R + N233R + P256T; |
| LVA182 | D27R + N33Q + G91A + L93* + N94* + F95* + D96* + D111A + T231R + N233R + P256T; |
| LVA185 | N11R + N33Q + T231R + N233R; |
| LVA198 | N33Q + N39H + T231R + N233R; |
| LVA202 | N33Q + P229R + T231R + N233R; |
| LVA206 | D27R + N33Q + G91N + N94R + D111A + G163K + S216P + L227G + T231R + N233R + P256T; |
| LVA208 | N33Q + G91T + G163K + T231R + N233R; |
| LVA210 | D27R + N33Q + G91A + D96E + L97Q + D111A + S216P + L227G + T231R + N233R +P256T; |
| LVA211 | D27R + N33Q + G91A + D96E + L97Q + D111A + S216P + T231R + N233R + P256T; |
| LVA214 | N33Q + E87A + T231R + N233R; |
| LVA216 | N33Q + E56Q + T231R + N233R; |
| LVA217 | N33Q + E210V + T231R + N233R; |
| LVA218 | N33Q + E56K + T231R + N233R; |
| LVA220 | N33Q + T231R + N233R + D254G; |
| LVA221 | N33Q + D96S + T231R + N233R; |
| LVA222 | N33Q + D122N + T231R + N233R; |
| LVA228 | N26A + N33Q + T231R + N233R; |
| LVA229 | N33Q + N162T + T231R + N233R; |
| LVA230 | N33Q + A150V + N162G + T231R + N233R; |
| LVA231 | N33Q + I90L + G163L + T231R + N233R; |
| LVA234 | N33Q + T231R + N233R + G240L; |
| LVA238 | D27R + N33Q + G91A + D96E + D111A + T231R + N233R + D254G + P256T; |
| LVA241 | D27R + N33Q + G91A + N94S + D111A + T231R + N233R + P256T; |
| LVA243 | N33Q + N200S + T231R + N233R; |
| LVA245 | N33Q + N39S + T231R + N233R; |
| LVA247 | N33Q + E210R + T231R + N233R; |
| LVA248 | N33Q + N39H + T231R + N233R + D254R; |
| LVA249 | N33Q + T231R + N233R + D254R; |
| LVA250 | N33Q + N94R + T231R + N233R; |
| LVA252 | N33Q + D96R + T231R + N233R; |
| LVA254 | D27N + N33Q + T231R + N233R; |
| LVA256 | D27N + N33Q + E56R + T231R + N233R; |
| LVA257 | N33Q + L227F + T231R + N233R; |
| LVA272 | N33Q + N73Y + G225P + T231R + N233R; |
| LVA273 | N33Q + G225P + T231R + N233R; |
| LVA275 | N33Q + T231R + N233R + D254S; |
| LVA277 | N33Q + D96G + T231R + N233R; |
| LVA279 | N33Q + D96N + T231R + N233R + D254S; |
| LVA280 | N33Q + T231R + N233R + D254G; |
| LVA281 | N33Q + D130H + T231R + N233R; |
| LVA284 | N33Q + E87A + T231R + N233R; |
| LVA287 | N33Q + T231R + N233R + E239D; |

-continued

| | |
|---|---|
| LVA307 | N33Q + D111A + T231R + N233R + D254G; |
| LVA308 | N33Q + E210V + T231R + N233R + D254S; |
| LVA310 | N11R + N33Q + E210V + T231R + N233R + D254S; |
| LVA315 | N33Q + G91T + G163K + T231R + N233R + D254G; |
| LVA317 | N33Q + G91T + G163K + T231R + N233R + D254S; |
| LVA319 | N11R + N33Q + G91T + G163K + T231R + N233R + D254S; |
| LVA325 | Q4R + D27R + N33Q + G91T + N94S + D111A + S216P + L227G + T231R + N233R + P256T; |
| LVA327 | N33Q + G91T + N94S + D111A + V176I + T231R + N233R; |
| LVA330 | Q4R + D27R + N33Q + G91T + N94S + D111A + E210D + S216P + L227G + T231R + N233R + P256T; |
| LVA331 | Q4R + D27Q + N33Q + G91T + N94S + D111A + S216P + L227G + T231R + N233R + P256T; |
| LVA333 | N33Q + G91T + N94S + D111A + T231R + N233R + P256T; |
| LVA334 | N33Q + G177A + T231R + N233R; |
| LVA338 | N33Q + T231R + N233R + G246A; |
| LVA341 | D27N + N33Q + G91T + G163K + T231R + N233R + D254S; |
| LVA345 | D27Q + N33Q + G91T + G163K + E219D + T231R + N233R; |
| LVA347 | N33Q + G91T + E219D + T231R + N233R; |
| LVA349 | K98I + T231R + N233R + N251S; |
| LVA353 | N33Q + G163R + T231R + N233R; |
| LVA355 | N33Q + G163N + T231R + N233R; |
| LVA357 | N33Q + G163C + T231R + N233R; |
| LVA359 | N33Q + G163Q + T231R + N233R; |
| LVA360 = LVA415 | N33Q + G163E + T231R + N233R; |
| LVA362 | N33Q + G163H + T231R + N233R; |
| LVA364 | N33Q + G163I + T231R + N233R; |
| LVA368 | N33Q + G163P + T231R + N233R; |
| LVA370 | N33Q + G163D + T231R + N233R; |
| LVA371 | N33Q + G91K + T231R + N233R; |
| LVA373 | N33Q + G91M + T231R + N233R; |
| LVA375 | N33Q + G91F + T231R + N233R; |
| LVA379 | N33Q + G91S + T231R + N233R; |
| LVA381 | N33Q + G91W + T231R + N233R; |
| LVA383 | N33Q + G91Y + T231R + N233R; |
| LVA387 | N33Q + G163T + T231R + N233R; |
| LVA389 | N33Q + G163W + T231R + N233R; |
| LVA391 | N33Q + G163Y + T231R + N233R; |
| LVA393 | N33Q + G163V + T231R + N233R; |
| LVA399 | N33Q + G91C + T231R + N233R; |
| LVA411 | N33Q + G91Y + Q126L + T231R + N233R; |
| LVA412 | N33Q + G91M + G161E + T231R + N233R; |
| LVA413 = LVA414 | N33Q + V128A + T231R + N233R; |
| LVA416 | N33Q + G163V + L185M + T231R + N233R; |
| LVA417 | N33Q + G38A + T231R + N233R; |
| LVA420 | N33Q + G163A + T231R + N233R; |
| LVA421 | N33Q + G91T + N94S + D111A + T231R + N233R; |
| LVA437 | N33Q + G38A + G163A + T231R + N233R; |
| LVA438 | N33Q + G163M + T231R + N233R; |
| LVA440 | N33Q + G91V + T231R + N233R; |
| LVA442 | N33Q + D111A + T231R + N233R + Q249R; |
| LVA444 | N33Q + D111A + T231R + N233R + D254S; |
| LVA449 | D27R + N33Q + G91A + D96E + L97Q + D111A + T231R + N233R + D254S + P256T; |
| LVA450 | D27R + N33Q + G91A + D96E + L97Q + D111A + T231R + N233R + D254G + P256T; |
| LVA451 | N33Q + G91T + N94R + T231R + N233R + D254S; |
| LVA453 | N33Q + G91T + N94R + D111A + W117L + T231R + N233R; |
| LVA454 | N33Q + W117L + T231R + N233R + D254S; |
| LVA456 | N33Q + T231R + N233R + P256T; |
| LVA458 | N33Q + T231R + N233R + D242E; |
| LVA460 | N33Q + E87R + T231R + N233R; |
| LVA461 | N33Q + E56R + T231R + N233R; |
| LVA463 | N33Q + N162G + T231R + N233R; |
| LVA464 | N33Q + G91L + T231R + N233R; |
| LVA468 | N33Q + E87H + T231R + N233R; |
| LVA470 | N33Q + D96N + T231R + N233R + Q249R; |
| LVA471 | N33Q + G91T + N94R + T231R + N233R + D254S; |
| LVA472 | N33Q + L227F + T231R + N233R + D254S; |
| LVA473 | D27R + N33Q + G91T + D96E + L97Q + D111A + T231R + N233R + D254S + P256T; |
| LVA474 | N33Q + G163A + T231R + N233R; |

-continued

| | |
|---|---|
| LVA480 | D27R + N33Q + G91T + D96E + D111A + T231R + N233R + D254S + P256T; |
| LVA482 | N33Q + G91T + N94R + T231R + N233R; |
| LVA483 | N33Q + T231R + N233R + D254A; |
| LVA484 | N33Q + T231R + N233R + D254N; |
| LVA486 | N33Q + T231R + N233R + D254Q; |
| LVA488 | N33Q + T231R + N233R + D254I; |
| LVA490 | N33Q + T231R + N233R + D254L; |
| LVA492 | N33Q + T231R + N233R + D254K; |
| LVA494 | N33Q + T231R + N233R + D254M; |
| LVA503 | N33Q + S216P + L227G + T231R + N233R + Q249R; |
| LVA505 | D27V + N33Q + V60S + G91T + D96W + T231R + N233R + Q249R; |
| LVA506 | N33Q + D96N + L227G + T231R + N233R + Q249R; |
| LVA507 | D27R + N33Q + L227G + T231R + N233R; |
| LVA509 | D27R + N33Q + L227G + T231R + N233R + Q249R; |
| LVA512 | N33Q + E219D + L227G + T231R + N233R + Q249R; |
| LVA513 | D27Q + N33Q + L227G + T231R + N233R + Q249R; |
| LVA516 | N33Q + W117L + L227G + T231R + N233R + Q249R; |
| LVA518 | D5E + N33Q + W117L + L227G + T231R + N233R + Q249R; |
| LVA519 | D27Q + N33Q + E219D + L227G + T231R + N233R + Q249R; |
| LVA520 | N33Q + D96E + E219D + L227G + T231R + N233R + Q249R; |
| LVA523 | D27R + N33Q + E56K + G91N + N94R + D111A + S216P + L227G + T231R + N233R + P256T; |
| LVA526 | D27R + N33Q + E56Q + D57N + G91N + N94R + D111A + S216P + L227G + T231R + N233R + P256T; |
| LVA527 | D27R + N33Q + E56Q + D57N + G91N + N94R + D111S + S216P + L227G + T231R + N233R + D254S + P256T; |
| LVA530 | D27R + N33Q + E56S + G91N + N94R + D111A + S216P + L227G + T231R + N233R + P256T; |
| LVA532 | D27R + N33Q + G91N + N94R + D111A + S216P + L227G + T231R + N233R + D254S + P256T; |
| LVA535 | D27R + N33Q + G91N + N94R + D111A + S216P + L227G + T231R + N233R + D254S + P256T; |
| LVA540 | D27R + N33Q + G91N + N94R + D111S + A155V + S216P + L227G + T231R + N233R + D254S + P256T; |
| LVA542 | D27R + N33Q + G91N + N94R + D111S + S216P + L227G + T231R + N233R + D254S + P256T; |
| LVA547 | N33Q + D111A + T231R + N233R + D254S; |
| LVA548 | N33Q + D111A + W117L + T231R + N233R + D254S; |
| LVA553 | N33Q + T231R + N233R + P256A; |
| LVA555 | N33Q + T231R + N233R + P256N; |
| LVA561 | N33Q + T231R + N233R + P256G; |
| LVA562 | N33Q + T231R + N233R + P256H; |
| LVA564 | N33Q + T231R + N233R + P256L; |
| LVA565 | N33Q + T231R + N233R + P256M; |
| LVA566 | N33Q + T231R + N233R + P256S; |
| LVA567 | N33Q + T231R + N233R + P256W; |
| LVA569 | N33Q + T231R + N233R + P256Y; |
| LVA576 | N33Q + T231R + N233R + P256F; |
| LVA578 | N33Q + T231R + N233R + P256V; |
| LVA580 | N33Q + G91M + G163W + T231R + N233R; |
| LVA581 | N33Q + G91M + G163T + T231R + N233R; |
| LVA582 | N33Q + G91M + G163D + T231R + N233R; |
| LVA583 | N33Q + G91K + G163W + T231R + N233R; |
| LVA586 | N33Q + G91T + G163W + T231R + N233R; |
| LVA602 | N33Q + V176N + T231R + N233R; |
| LVA604 | N33Q + V176D + T231R + N233R; |
| LVA614 | N33Q + W117F + T231R + N233R; |
| LVA620 | N33Q + G91T + N94S + D111A + V176I + T231R + N233R + D254S; |
| LVA622 | N33Q + V176I + T231R + N233R; |
| LVA623 | N33Q + D111N + T231R + N233R; |
| LVA627 | N33Q + D111N + G225P + T231R + N233R; |
| LVA629 | N33Q + D111N + S216P + T231R + N233R; |
| LVA631 | D27R + N33Q + G91T + N94R + D111A + S216P + L227G + T231R + N233R; |
| LVA632 | N33Q + G91M + G163P + T231R + N233R; |
| LVA634 | N33Q + G91T + G163A + T231R + N233R; |
| LVA639 | N33Q + W117D + T231R + N233R; |
| LVA640 | N33Q + W117H + T231R + N233R; |
| LVA649 = LVA650 | N33Q + W117C + T231R + N233R; |
| LVA651 | N33Q + W117K + T231R + N233R; |
| LVA653 | N33Q + W117V + T231R + N233R; |
| LVA656 | N11S + N33Q + T231R + N233R; |
| LVA658 | N33Q + W117E + V176K + T231R + N233R; |

-continued

| | |
|---|---|
| LVA659 | N33Q + W117G + T231R + N233R; |
| LVA664 | N33Q + W117P + T231R + N233R; |
| LVA665 | N33Q + W117S + T231R + N233R; |
| LVA666 | N33Q + W117T + T231R + N233R; |
| LVA667 | N33Q + W117I + T231R + N233R; |
| LVA670 | D27R + N33Q + L227G + T231R + N233R + Q249R + D254S; |
| LVA672 | N33Q + S115L + T231R + N233R; |
| LVA675 | N33Q + G38A + G91T + G163K + T231R + N233R + D254S; |
| LVA696 | N33Q + V176M + T231R + N233R; |
| LVA697 | N33Q + V176H + T231R + N233R; |
| LVA700 | N33Q + V176A + T231R + N233R; |
| LVA702 | D27V + N33Q + L227F + T231R + N233R + Q249R; |
| LVA705 | N33Q + W117Y + T231R + N233R; |
| LVA707 | N33Q + W117Y + V176D + T231R + N233R; |
| LVA713 | D27V + N33Q + G91A + N94R + D111A + G163K + L227F + T231R + N233R + Q249R; |
| LVA714 = LVAR714 | D27V + N33Q + G91A + N94R + D111A + G163K + L227F + T231R + N233R + Q249R + D254S; |
| LVA715 | D27R + N33Q + P136H + L227G + T231R + N233R + Q249R + D254S; |
| LVA718 | N11R + N33Q + T231R + N233R + T244S; |
| LVA721 | N33Q + G91T + D96N + D111A + V176I + T231R + N233R + D254S; |
| LVA722 | N33Q + G91T + N94S + D111A + V176I + T231R + N233R + D254S; |
| LVA723 | N33Q + G161A + T231R + N233R; |
| LVA731 | N33Q + G38I + G177A + T231R + N233R; |
| LVA732 | N33Q + N101Q + T231R + N233R; |
| LVA733 | N33Q + N94Q + T231R + N233R; |
| LVA734 | N33Q + G161A + T231R + N233R; |
| LVA736 | N11Q + N33Q + T231R + N233R; |
| LVA738 | N8Q + N33Q + T231R + N233R; |
| LVA740 | N33Q + T231R + N233R + N251Q; |
| LVA743 | N33Q + N200Q + T231R + N233R; |
| LVA744 | N33Q + G177A + T231R + N233R; |
| LVA746 | N33Q + N73Q + T231R + N233R; |
| LVA749 | N33Q + I86L + T231R + N233R; |
| LVA753 | N33Q + K98I + G163K + T231R + N233R; |
| LVA754 | D27R + N33Q + G91T + D96E + D111A + G163K + T231R + N233R + D254S + P256T; |
| LVA755 | D27R + N33Q + G91T + D96E + D111A + G163A + T231R + N233R + D254S + P256T; |
| LVA770 | D27R + N33Q + S216P + L227G + T231R + N233R + Q249R; |
| LVA771 | N33Q + K98I + G163K + N200Q + T231R + N233R + N251S; |
| LVA772 | N33Q + G38S + G163K + T231R + N233R; |
| LVA773 | D27R + N33Q + G38A + G91T + D96E + D111A + T231R + N233R + D254S + P256T; |
| LVA774 | N33Q G38Y T231R N233R; |
| LVA777 | D27R + N33Q + G91T + N94R + D111A + S216P + L227G + T231R + N233R + P256T; |
| LVA778 | D27R + N33Q + G91T + N94R + D111A + S216P + L227G + T231R + N233R + P256T; |
| LVA782 | N33Q + G38N + N73Q + T231R + N233R; |
| LVA783 | N33Q + G38D + R84E + T231R + N233R; |
| LVA784 | N33Q + G38Q + T231R + N233R; |
| LVA786 | N33Q + G38I + T231R + N233R; |
| LVA788 | N33Q + G38K + T231R + N233R; |
| LVA792 | N33Q + G38F + T231R + N233R; |
| LVA799 | N33Q + G38H + N200Q + T231R + N233R + N251S; |
| LVA800 | N33Q + G38L + T231R + N233R; |
| LVA801 | N33Q + G38M + T231R + N233R; |
| LVA803 | N33Q + G38F + T231R + N233R; |
| LVA804 | N33Q + G38P + T231R + N233R; |
| LVA805 | N33Q + G38T + T231R + N233R; |
| LVA806 | N11R + N33Q + G91T + W117I + G163K + T231R + N233R + D254S; |
| LVA808 | D27R + N33Q + G38A + G91T + D96E + D111A + G163K + T231R + N233R + D254S + P256T; |
| LVA809 | N11R + N33Q + G91T + W117I + G163K + T231R + N233R + D254S; |
| LVA811 | D27R + N33Q + G38A + G91T + D96E + D111A + G163A + T231R + N233R + D254S + P256T; |
| LVA813 | D27R + N33Q + V176Q + L227G + T231R + N233R + Q249R + D254S; |
| LVA814 | N33Q + W117I + V176Q + T231R + N233R + P256A; |
| LVA816 | N33Q + G38A + G163A + T231R + N233R + P256A; |

-continued

| | |
|---|---|
| LVA817 | N33Q + W117I + V176Q + T231R + N233R; |
| LVA818 | N33Q + G177A + T231R + N233R + G246A; |
| LVA819 | E1N + N33Q + T231R + N233R; |
| LVA821 | N33Q G38H T231R N233R; |
| LVA829 | N33Q + G91A + N94K + D111A + G163K + L227F + T231R + N233R + Q249R + D254S; |
| LVA830 | N11R + N33Q + G91T + G163K + V176Q + T231R + N233R + D254S; |
| LVA831 | N33Q + K98I + T231R + N233R; |
| LVA834 | D27R + N33Q + W117I + V176Q + L227G + T231R + N233R + Q249R + D254S; |
| LVA835 | N11R + N33Q + G38A + G91T + G163K + T231R + N233R + D254S; |
| LVA839 | N33Q + G163W + T231R + N233R; |
| LVA841 | N33Q + G38A + G163A + T231R + N233R; |
| LVA842 | D27R + N33Q + G91T + D96E + L97Q + D111A + T231R + N233R + D254S + P256T; |
| LVA844 | N33Q + T231R + N233R + D254Q; |
| LVA846 | N11R + N33Q + G91T + S115L + G163K + T231R + N233R + D254S; |
| LVA847 | N11R + N33Q + G91T + G163K + V176W + T231R + N233R + D254S; |
| LVA848 = LVA849 | N33Q + G163D + T231R + N233R; |
| LVA850 | N33Q + G163P + T231R + N233R; |
| LVA853 | E1D + N33Q + G91T + N94R + D111A + W117L + T231R + N233R + D254S; |
| LVA857 | N33Q + G91T + N94R + D111A + W117L + V176W + T231R + N233R; |
| LVA860 | Q4P + D27R + N33Q + G91N + N94R + D111A + L206F + S216P + L227G + T231R + N233R + P256T; |
| LVA862 | D27R + N33Q + T37K + N71I + G91N + N94R + K98I + D111A + S216P + L227G + T231R + N233R + P256T; |
| LVA863 | D27R + N33Q + E43K + K46M + I90V + G91N + N94R + D111A + T114I + S216P + L227G + T231R + N233R + P256T; |
| LVA865 | N33Q + W117S + T231R + N233R; |
| LVA866 | N33Q + G61R + V63R + G156R + V176W + T231R + N233R + P256I; |
| LVA869 | N33Q + D96N + G156R + V176W + T231R + N233R; |
| LVA871 | N33Q + G156R + V176W + T231R + N233R + Q249R; |
| LVA873 | N33Q + G91T + N94S + D111A + G163T + V176W + T231R + N233R; |
| LVA875 | N33Q + G91T + N94S + D111A + S115L + G163T + V176I + T231R + N233R; |
| LVA877 | N11R + D27R + N33Q + E56Q + D57N + G91N + N94R + D111S + G163T + S216P + L227G + T231R + N233R + D254S + P256T; |
| LVA878 | D27R + N33Q + E56Q + D57N + G91N + N94R + D111S + G163T + S216P + L227G + T231R + N233R + D254S + P256T; |
| LVA880 | N11R + D27R + N33Q + E56Q + D57N + G91N + N94R + D111S + S216P + L227G + T231R + N233R + D254S + P256T; |
| LVA882 | D27R + N33Q + E56Q + D57N + G91N + N94R + D111S + S216P + L227G + T231R + N233R + D242E + D254S + P256T; |
| LVA883 | D27R + N33Q + G38A + E56Q + D57N + G91N + N94R + D111S + S216P + L227G + T231R + N233R + D254S + P256T; |
| LVA888 | Q4R + D27Q + N33Q + G91T + N94S + E99D + D111A + E210D + S216P + L227G + T231R + N233R + P256L; |
| LVA890 | N33Q + G38A + G91T + G163A + T231R + N233R + D254S; |
| LVA892 | N33Q + G38A + G163A + T231R + N233R + D254I; |
| LVA896 | N11R + N33Q + I90L + G163L + T231R + N233R; |
| LVA897 | N11R + N33Q + I90L + G163L + T231R + N233R + D254S; |
| LVA899 | N11R + N33Q + E56Q + G91T + G163K + V176Q + T231R + N233R + D254S; |
| LVA904 | N11R + D27R + N33Q + G91T + D96E + D111A + G163K + T231R + N233R + D254S + P256T; |
| LVA906 | N11R + N33Q + G38A + G91T + G112A + G163A + T231R + N233R + D254S; |
| LVA907 | N11R + N33Q + G91T + G163K + E210D + T231R + N233R + D254S; |
| LVA913 | N11R + N33Q + G91T + G163K + T231R + N233R + D254I; |
| LVA915 | N11R + N33Q + G91T + G163K + V176T + T231R + N233R + D254S; |

-continued

| | |
|---|---|
| LVA917 | N11R + N33Q + G91T + G163P + T231R + N233R + D254S; |
| LVA919 | N11R + N33Q + G91M + G163T + T231R + N233R + D254S; |
| LVA921 | N11R + N33Q + G38A + G91T + G163K + V176D + T231R + N233R + D254S; |
| LVA925 | N33Q + E56Q + G156R + V176W + T231R + N233R; |
| LVA927 | E1D + N33Q + G38A + G91T + N94R + D111A + W117L + V176W + T231R + N233R; |
| LVA928 | N33Q + G163K + G177A + T231R + N233R + G246A; |
| LVA929 | N11R + N33Q + E56Q + G91T + G163K + T231R + N233R + D254S; |
| LVA930 | N11R + N33Q + I90L + G163K + T231R + N233R + D254S; |
| LVA933 | D27R + N33Q + E56Q + D57N + G91N + N94R + D111S + S216P + L227G + T231R + N233R + Q249R + D254S + P256T; |
| LVA934 | D27R + N33Q + E56Q + D57N + G91N + N94R + D111S + S216P + E219D + L227G + T231R + N233R + D254S + P256T; |
| LVA941 | N11R + N33Q + I90L + G91T + N94S + D96E + G163K + T231R + N233R + D254S; |
| LVA942 | N11R + N33Q + G91T + G163K + V176I + T231R + N233R + D254S; |
| LVA943 | N11R + N33Q + G91T + G163K + V176Q + T231R + N233R + D254S; |
| LVA944 | N11R + N33Q + G91T + G163A + V176T + T231R + N233R + D254S; |
| LVA945 | N11R + N33Q + G91T + G163L + V176I + T231R + N233R + D254S; |
| LVA946 | N11R + N33Q + G91T + G163L + V176T + T231R + N233R + D254S; |
| LVA947 | N11R + N33Q + G91T + G163L + T231R + N233R + D254S; |
| LVA948 | N11R + N33Q + G91T + G163P + T231R + N233R + D254S; |
| LVA949 | N11R + N33Q + G91T + G163P + V176I + T231R + N233R + D254S; |
| LVA950 | N11R + N33Q + G91T + G163L + T231R + N233R + D254S + P256N; |
| LVA952 | D27R + N33Q + E56Q + D57N + G91N + N94R + D111S + G163T + S216P + L227G + T231R + N233R + Q249R + D254S + P256T; |
| LVA953 | Q4R + D27Q + N33Q + G91T + N94S + E99D + D111A + G163A + E210V + S216P + L227G + T231R + N233R + P256L; |
| LVA954 | Q4R + D27Q + N33Q + G91T + N94S + E99D + D111A + V176I + E210V + S216P + L227G + T231R + N233R + P256L; |
| LVA959 | N33Q + E210Y + T231R + N233R + D254Y + I255F; |
| LVA961 | N33Q + L93F + D102Y + T231R + N233R; |
| LVA962 | D27R + N33Q + L227G + T231R + N233R + Q249R + D254S; |
| LVA964 | N11S + N33Q + T231R + N233R; |
| LVA966 | N11R + N33Q + T231R + N233R; |
| LVA968 | N33Q + G38A + G91T + G163K + T231R + N233R + D254S; |
| LVA969 | N33Q + W117Y + V176T + T231R + N233R; |
| LVA970 | N8L + N11R + N33Q + G91T + G163K + T231R + N233R + D254S; |
| LVA972 | E1N + N33Q + G38A + G91T + G163P + V176F + T231R + N233R; |
| LVA973 | N11R + N33Q + G38A + G91T + G163P + V176G + T231R + N233R + D254S; |
| LVA976 | N11R + N33Q + G91T + G163K + T231R + N233R + D254A + P256F; |
| LVA977 | N11R + N33Q + G91T + G163K + T231R + N233R + P256F; |
| LVA978 | N11R + N33Q + G91T + G163K + T231R + N233R + D254S + P256F; |
| LVA979 | N11R + N33Q + G38A + G91T + G156R + G163K + V176T + T231R + N233R + D254S; |
| LVA980 | N33Q + G91K + D96S + G163T + T231R + N233R + Q249R; |
| LVA981 | N11R + N33Q + G91T + G163N + T231R + N233R + D254S; |
| LVA983 | N11R + N33Q + G91T + G163T + T231R + N233R + D254S; |
| LVA984 | N11R + N33Q + G91T + G163W + T231R + N233R + D254S; |

-continued

| | |
|---|---|
| LVA985 | N11R + N33Q + G91K + G163K + T231R + N233R + D254S; |
| LVA987 | N11R + G23E + N33Q + G91T + G163K + T231R + N233R + D254S; |
| LVA988 | N11R + N33Q + G91T + V141E + G163K + T231R + N233R + D254S; |
| LVA989 | N11R + N33Q + L52R + G91T + G163K + T231R + N233R + D254S; |
| LVA990 | N11R + N33Q + G91T + V141L + G163K + T231R + N233R + D254S; |
| LVA991 | N11R + N33Q + T37K + G91T + G163K + T231R + N233R + D254S; |
| LVA993 | N11R + N33Q + A68V + G91T + G163K + T231R + N233R + D254S; |
| LVA994 | N11R + N33Q + G91T + G163A + V176I + T231R + N233R + D254S; |
| LVA995 | N11R + N33Q + T37M + G91T + G163P + V176T + T231R + N233R + D254S; |
| LVA997 | N11R + N33Q + G91T + G163L + T231R + N233R + D254S; |
| LVA998 | N11R + N33Q + G91T + G163K + T231R + N233R + D254S + P256I; |
| LVA999 | N33Q + G38S + G156R + G163K + V176W + T231R + N233R; |
| LVA1000 | N11R + D27R + N33Q + E56Q + D57N + G91N + N94R + D111S + G163K + S216P + L227G + T231R + N233R + D254S + P256T; |
| LVA1002 | N11R + N33Q + G38A + G91T + G163P + V176G + T231R + N233R + D254S; |
| LVA1003 | N11R + N33Q + G38A + G91T + G163Q + V176G + T231R + N233R + D254S; |
| LVA1004 | N11R + N33Q + G38A + G91T + G163T + V176G + T231R + N233R + D254S; |
| LVA1005 | N11R + N33Q + G38A + G91T + N94R + G163P + V176G + T231R + N233R + D254S; |
| LVA1006 | E1* + N11R + N33Q + G38A + G91N + N94R + G163P + V176G + T231R + N233R + D254S; |
| LVA1007 | E1N + N11R + N33Q + G38A + G91T + G163P + V176F + T231R + N233R; |
| LVA1008 | E1N + F10L + N11R + N33Q + G38A + G91T + G163P + V176F + T231R + N233R; |
| LVA1009 | E1N + N33Q + G38A + G91T + G163P + V176F + T231R + N233R + D254S; |
| LVA1010 | E1N + N33Q + G38A + G91T + D111A + G163P + V176F + T231R + N233R; |
| LVA1011 | E1N + N33Q + G38A + G91T + G163P + V176F + L227F + T231R + N233R; |
| LVA1012 | E1N + N11R + N33Q + G38A + G91T + D111A + G163P + V176F + T231R + N233R; |
| LVA1013 | E1N + N33Q + G38A + G91T + G163P + V176F + L227F + T231R + N233R + D254S; |
| LVA1014 | E1N + N33Q + G38A + G91T + G163P + V176F + T231R + N233R + D254S + I255A + P256Q; |
| LVA1015 | E1N + N11R + N33Q + G38A + G91T + D111A + G163P + V176F + T231R + N233R + D254S; |
| LVA1017 | N33Q + G156R + V176W + T231R + N233R + P256I; |
| LVA1018 | N33Q + G91T + N94S + D111A + G156R + G163T + V176W + T231R + N233R; |
| LVA1019 | N33Q + G91T + N94S + D111A + G156R + G163T + V176I + T231R + N233R; |
| LVA1021 | N11R + N33Q + G38A + G91T + D102G + S115L + G163K + T231R + N233R + D254S + P256T; |
| LVA1023 | N11R + N33Q + G38A + G91T + S115L + G163K + T231R + N233R + D254S + P256T; |
| LVA1027 | E1N + N11R + N33Q + G91T + G163A + T231R + N233R + G246A + D254S; |
| LVA1028 | N11R + D27R + N33Q + D57G + G91T + D96E + D111A + G163K + T231R + N233R + D254S + P256T; |
| LVA1029 | N33Q + D96N + G156R + V176W + T231R + N233R + Q249R; |
| LVA1031 | N33Q + I86F + L93F + D102Y + E210Y + L227F + T231R + N233R + D254Y + I255F + L269F; |
| LVA1032 | N33Q + I86F + L93F + D102Y + E210Y + L227F + T231R + N233R + D254Y + I255F; |
| LVA1033 | N11C + N33Q + G91T + G163K + T231R + N233R + D254S; |
| LVA1034 | N11L + N33Q + G91T + G163K + T231R + N233R + D254S; |
| LVA1035 | N11H + N33Q + G91T + G163K + T231R + N233R + D254S; |

-continued

| | |
|---|---|
| LVA1036 | N11D + N33Q + G91T + G163K + T231R + N233R + D254S; |
| LVA1037 | N11R + N33Q + G91T + D96W + G163K + T231R + N233R + D254S; |
| LVA1038 | D27R + N33Q + G91T + D96E + L97Q + D111A + G163K + T231R + N233R + D254S + P256T; |
| LVA1040 | N11P + N33Q + G91T + G163K + T231R + N233R + D254S; |
| LVA1041 | Q4R + D27N + N33Q + G38A + G91T + N94S + E99D + D111A + V176I + E210V + S216P + L227G + T231R + N233R + P256L; |
| LVA1044 | N11R + N33Q + E56Q + G163K + T231R + N233R + D254S; |
| LVA1045 | N11R + N33Q + G91T + G163A + T231R + N233R + D254S; |
| LVA1046 | N11R + N33Q + G91T + G163P + T231R + N233R + D254S; |
| LVA1048 | N11R + N33Q + G91T + G163K + L227G + P229R + T231R + N233R + D254S; |
| LVAR0074 | N33Q + E87K + T231R + N233R; |
| LVAR0076 | N33Q + N94K + T231R + N233R; |
| LVAR0077 | N33Q + D96Y + T231R + N233R; |
| LVAR0079 | N33Q + K98I + T231R + N233R; |
| LVAR0080 | A30V + N33Q + K98I + T231R + N233R; |
| LVAR0086 | N33Q + E87K + D96E + T231R + N233R; |
| LVAR0088 | N26I + N33Q + T231R + N233R; |
| LVAR0091 | A30T + N33Q + T231R + N233R; |
| LVAR0094 | N33Q + G91V + T231R + N233R; |
| LVAR0095 | N33Q + G91A + T231R + N233R; |
| LVAR0096 | N33Q + G91V + L97M + T231R + N233R; |
| LVAR0099 | N33Q + K98I + T231R + N233R; |
| LVAR0101 | N33Q + L69I + G91E + T231R + N233R; |
| LVAR0102 | P29T + N33Q + T231R + N233R; |
| LVAR0103 | N33Q + G91V + T231R + N233R; |
| LVAR0104 | N33Q + K98I + T231R + N233R; |
| LVAR0106 | N33Q + G91E + T231R + N233R; |
| LVAR0108 | N33Q + N94K + T231R + N233R; |
| LVAR204 | D27R + N33Q + G91N + N94R + K98I + D111A + N162S + S216P + L227G + T231R + N233R + P256T; |
| LVAR205 | D27R + N33Q + T37K + N71I + G91N + N94R + K98I + D111A + S216P + L227G + T231R + N233R + P256T; |
| LVAR207 | D27R + N33Q + N39S + G91N + N94R + D111A + S216P + L227G + T231R + N233R + P256T; |
| LVAR208 | D27R + N33Q + I76T + G91N + N94R + R108M + D111A + S216P + L227G + T231R + N233R + P256T; |
| LVAR209 | D27R + N33Q + L52I + V60E + G91N + N94R + D111A + T114I + V168M + E210D + S216P + L227G + T231R + N233R + P256T; |
| LVAR214 | Q4P + D27R + N33Q + G91N + N94R + D111A + R205I + L206F + S216P + L227G + T231R + N233R + P256T; |
| LVAR215 | Q4H + D27R + N33Q + G91N + N94R + D111A + V154L + S216P + L227G + T231R + N233R + P256T; |
| LVAR216 | D27R + N33Q + G91N + N94R + D111A + V154I + S216P + L227G + T231R + N233R + P256T; |
| LVAR218 | D27R + N33Q + N71S + G91N + N94R + D111A + H135D + S216P + L227G + T231R + N233R + P256T; |
| LVAR219 | D27R + N33Q + G91N + N94R + K98I + D111A + S216P + L227G + T231R + N233R + P256T; |
| LVAR220 | D27R + N33Q + G91N + N94R + L97M + D111A + S216P + T226N + L227G + T231R + N233R + P256T + L269H; |
| LVAR223 | D27R + N33Q + G91N + N94R + D111A + T114I + R179T + S216P + L227G + T231R + N233R + P256T; |
| LVAR225 | D27R + N33Q + G91N + N94R + D111A + S216P + L227G + T231R + N233R |
| LVAR226 | G23E + D27R + N33Q + L52R + G91N + N94R + D111A + T114I + V141E + S216P + L227G + T231R + N233R + P256T; |
| LVAR230 | D27R + N33Q + E43K + K46M + I90V + G91N + N94R + D111A + T114I + S216P + L227G + T231R + N233R + P256T; |
| LVAR231 | D27R + A30V + N33Q + G91N + N94R + G109A + D111A + G190D + S216P + L227G + T231R + N233R + P256T; |
| LVAR234 | D27R + N33Q + A49T + G91N + N94R + D111A + Y138F + G163R + S216P + L227G + T231R + N233R + P256T; |
| LVAR235 | N26H + D27R + N33Q + G91N + N94R + D111A + V154F + G190C + S216P + L227G + T231R + N233R + P256T; |

-continued

| | |
|---|---|
| LVAR277 | N33Q + G91T + D96E + K98T + T114I + G163S + E210V + T231R + N233R + D254K + P256A; |
| LVAR280 | N33Q + G91T + D96E + K98T + T114I + T231R + N233R + G163S; |
| LVAR281 | N33Q + G91T + D96E + K98T + T114I + G163K + E210D + T231R + N233R; |
| LVAR282 | N33Q + G91T + T114I + G163K + E210D + T231R + N233R + D254G + P256A; |
| LVAR283 | D27R + N33Q + G91T + T114I + G163W + E210D + T231R + N233R; |
| LVAR284 | D27N + N33Q + G91T + T114I + G163S + E210D + T231R + N233R + P256T; |
| LVAR285 | N33Q + G91T + T114I + G163K + E210D + T231R + N233R; |
| LVAR286 | N33Q + G38W + G91T + T114I + G163K + E210V + T231R + N233R; |
| LVAR287 | N33Q + G38W + G91T + T114I + G163K + E210D + T231R + N233R + P256T; |
| LVAR288 | D27I + N33Q + G91T + D96E + K98T + T114I + G163K + E210D + T231R + N233R + P256T; |
| LVAR290 | N33Q + G91T + T114I + E210V + T231R + N233R + D254K + P256A; |
| LVAR828 = LVA828 | N33Q + G91A + N94K + D111A + G163K + L227F + T231R + N233R + Q249R; |
| LVAR861 | G23E + D27R + N33Q + L52R + G91N + N94R + D111A + T114I + V141E + S216P + L227G + T231R + N233R + P256T; |
| LVAR863 | D27R + N33Q + E43K + K46M + I90V + G91N + N94R + D111A + T114I + S216P + L227G + T231R + N233R + P256T; |
| LVAR955 | N33Q + G91T + K98I + T114I + G163K + T231R + N233R + D254S; |
| LVAR956 | N33Q + G91T + K98I + G163K + T231R + N233R + D254S + P256L; |
| LVA957 | N33Q + G91T + T114I + G163K + T231R + N233R + D254S + P256L; |
| LVAR1042 | G23E + D27R + N33Q + L52R + G91N + N94R + D111A + T114I + V141E + S216P + L227G + T231R + N233R + P256T; and |
| LVAR1043 | D27R + N33Q + E43K + K46M + I90V + G91N + N94R + D111A + T114I + S216P + L227G + T231R + N233R + P256T. |

The following are additional particular embodiments of the invention (the lipase of SEQ ID NO: 1 is variant (T231R+N233R) of the lipase of amino acids 1-269 of SEQ ID NO: 2):

1. A lipase for use as a medicament, wherein the lipase is a variant of a parent lipase, which variant (a) has at least 50% identity to amino acids 1 to 269 of SEQ ID NO: 2; and (b) has lipase activity; and (c) comprises at least one substitution selected from the following substitutions: N26I, D27Q, D27R, D27Y, P29T, A30T, A30V, T32I, N33Q, N33T, N33Y, P42L, E43D, E43K, E43M, E43V, A49T, E56A, E56C, E56K, E56R, E56S, D57A, D57A, D57G, D57N, V60L, L69I, E87K, G91A, G91E, G91N, G91R, G91S, G91T, G91V, G91W, L93F, N94K, N94R, N94S, D96E, D96G, D96L, D96N, D96S, D96V, D96W, D96Y, L97M, L97Q, K98I, E99D, E99K, E99P, E99S, E99T, D111A, D111S, T114I, L147S, G163K, E210D, S216P, L227G, T231R, N233R, D234K, E239V, Q249R, N251S, D254N, P256T, G263Q, L264A, 1265T, G266D, T267A, and L269N, wherein each position corresponds to a position of amino acids 1 to 269 of SEQ ID NO: 2; and (d) with the proviso that the variant is not (i) the lipase having amino acids 1-269 of SEQ ID NO: 1, and not (ii) variant N33Q of the lipase of (i).
2. A lipase for use as a medicament, wherein the lipase is a variant of a parent lipase, which variant (a) has at least 50% identity to amino acids 1 to 269 of SEQ ID NO: 2; and (b) has lipase activity; and (c) comprises substitutions T231R and N233R and furthermore at least one substitution selected from the following substitutions: N26I, D27Q, D27R, D27Y, P29T, A30T, A30V, T321, N33Q, N33T, N33Y, P42L, E43D, E43K, E43M, E43V, A49T, E56A, E56C, E56K, E56R, E56S, D57A, D57G, D57N, V60L, L69I, E87K, G91A, G91E, G91N, G91R, G91S, G91T, G91V, G91W, L93F, N94K, N94R, N94S, D96E, D96G, D96L, D96N, D96S, D96V, D96W, D96Y, L97M, L97Q, K98I, E99D, E99K, E99P, E99S, E99T, D111A, D111S, T114I, L147S, G163K, E210D, S216P, L227G, D234K, E239V, Q249R, N251S, D254N, P256T, G263Q, L264A, I265T, G266D, T267A, and L269N, wherein each position corresponds to a position of amino acids 1 to 269 of SEQ ID NO: 2; and (d) with the proviso that the lipase is not variant N33Q of amino acids 1-269 of SEQ ID NO: 1.
3. A lipase for use as a medicament, wherein the lipase is a variant of a parent lipase, which variant (a) has at least 50% identity to amino acids 1 to 269 of SEQ ID NO: 2; and (b) has lipase activity; and (c) comprises at least one substitution in at least one of positions 30, 42, 114, and/or 163, wherein each position corresponds to a position of amino acids 1 to 269 of SEQ ID NO: 2.
4. A lipase for use as a medicament, wherein the lipase is a variant of a parent lipase, which variant (a) has at least 50% identity to amino acids 1 to 269 of SEQ ID NO: 2; and (b) has lipase activity; and (c) comprises at least one substitution selected from the following substitutions: A30T, A30V, P42L, T114I, and G163K, wherein each position corresponds to a position of amino acids 1 to 269 of SEQ ID NO: 2.
5. A lipase for use as a medicament, wherein the lipase is a variant of a parent lipase, which variant (a) has at least 50% identity to amino acids 1 to 269 of SEQ ID NO: 2; and (b) has lipase activity; and (c) is selected from the following variants:

| | |
|---|---|
| LVA012: | D27R + N33Q + G91A + D96E + L97Q + D111A + T231R + N233R + P256T, |
| LVA023: | N33Q + E210D + T231R + N233R, |
| LVA041: | N33Q + D111A + T231R + N233R, |
| LVA043: | N33Q + G91T + T231R + N233R, |
| LVA049: | N33Q + G163K + T231R + N233R, |
| LVA061: | D27Q + N33Q + T231R + N233R, |
| LVA099: | D27R + N33Q + G91T + N94S + D111A + S216P + L227G + T231R + N233R + P256T, |
| LVA349: | K98I + T231R + N233R + N251S, |
| LV1232: | G91A + D96W + E99K + G263Q + L264A + I265T + G266D + T267A + L269N, |
| LV1330: | N33Q + D96S + T231R + N233R + Q249R, |
| LV1855: | D27R + G91A + D111A + S216P + L227G + P256T, |
| LV1857: | D27R + G91N + N94R + D111A + S216P + L227G + P256T, |
| LV1865: | D27R + G91T + N94S + D111A + S216P + L227G + P256T, |
| LV1874: | D27R + G91S + D111A + S216P + L227G + P256T, |
| LV1889: | D27R + G91T + D96N + D111A + S216P + L227G + P256T, |
| LVAR0002b | T32I + G91V + T231R + N233R, |
| LVAR0003: | K98I + T231R + N233R, |
| LVAR0011a | G91A + T231R + N233R, |
| LVAR0013: | G91V + T231R + N233R, |
| LVAR0014 | N33Y + G91W + N94K + T231R + N233R, |
| LVAR0015 | P42L + D57N + G91E + T231R + N233R, |
| LVAR0016 | K98I + T231R + N233R, |
| LVAR0017 | V60L + G91V + T231R + N233R, |
| LVAR0032: | D57G + L93F + T231R + N233R, |
| LVAR0045: | A49T + E56R + E87K + E99S + T231R + N233R, |
| LVAR0046: | E99T + T114I + D254N + T231R + N233R, |
| LVAR0047: | D27Y + E87K + D96L + E99P + T231R + N233R, |
| LVAR0048 | E43K + E56S + E87K + T231R + N233R, |
| LVAR0050: | E56S ++ E87K + D96L + E99D + T231R + N233R, |
| LVAR0051: | E56A + D57A + T114I + T231R + N233R, |
| LVAR0052: | G91E + T231R + N233R, |
| LVAR0053: | E56K + D96G + D111A + T231R + N233R, |

-continued

| | |
|---|---|
| LVAR0054: | E87K + D111S + T231R + N233R, |
| LVAR0055 | E43V + G91R + T231R + N233R, |
| LVAR0056: | E56S + E87K + T231R + N233R, |
| LVAR0057: | E87K + G91E + T231R + N233R, |
| LVAR0058: | D27Y + E87K + T231R + N233R, |
| LVAR0059 | E43M + E87K + D96L + E99P + T231R + N233R, |
| LVAR0061: | E56K + E87K + D111A + T231R + N233R, |
| LVAR0062: | E87K + E99P + T231R + N233R, |
| LVAR0063: | E87K + D96L + E99P + T231R + N233R, |
| LVAR0064: | E56C + E87K + T231R + N233R, |
| LVAR0065: | E56R + E87K + D96L + T231R + N233R, |
| LVAR0066 | E43D + E56A + D57A + E87K + D111A + T231R + N233R, |
| LVAR0067: | E56K + E87K + D96L + E99P + T231R + N233R, |
| LVAR0068 | E87K + L147S + T231R + N233R, |
| LVAR0069: | D27Y + E87K + D96L + E99P + T231R + N233R, |
| LVAR0070 | E43D + E87K + D96L + E99P + E239V + T231R + N233R, |
| LVAR0071 | E43K + E56A + E87K + D234K + T231R + N233R, |
| LVAR0072: | D96V + D111A + T231R + N233R, |
| LVAR0074: | N33Q + E87K + T231R + N233R, |
| LVAR0076: | N33Q + N94K + T231R + N233R, |
| LVAR0077: | N33Q + D96Y + T231R + N233R, |
| LVAR0078: | N33T + E43V + E56K + D96G + T231R + N233R, |
| LVAR0079: | N33Q + K98I + T231R + N233R, |
| LVAR0080: | A30V + N33Q + K98I + T231R + N233R, |
| LVAR0086: | N33Q + E87K + D96E + T231R + N233R, |
| LVAR0088: | N26I + N33Q + T231R + N233R, |
| LVAR0091: | A30T + N33Q + T231R + N233R, |
| LVAR0094: | N33Q + G91V + T231R + N233R, |
| LVAR0095: | N33Q + G91A + T231R + N233R, |
| LVAR0096: | N33Q + G91V + L97M + T231R + N233R, |
| LVAR0099: | N33Q + K98I + T231R + N233R, |
| LVAR0101: | N33Q + L69I + G91E + T231R + N233R, |
| LVAR0102: | P29T + N33Q + T231R + N233R, |
| LVAR0103: | N33Q + G91V + T231R + N233R, |
| LVAR0104: | N33Q + K98I + T231R + N233R, |
| LVAR0106: | N33Q + G91E + T231R + N233R, and |
| LVAR0108: | N33Q + N94K + T231R + N233R, |

wherein each position corresponds to a position of amino acids 1 to 269 of SEQ ID NO: 2.

6. A lipase being a variant of a parent lipase, which variant (a) has at least 50% identity to amino acids 1 to 269 of SEQ ID NO: 2; and (b) has lipase activity; and (c) comprises at least one substitution in at least one of positions 30, 42, 114, and/or 163, wherein each position corresponds to a position of amino acids 1 to 269 of SEQ ID NO: 2.
7. A lipase being a variant of a parent lipase, which variant (a) has at least 50% identity to amino acids 1 to 269 of SEQ ID NO: 2; and (b) has lipase activity; and (c) comprises at least one of the following substitutions: D27Y, P29T, A30T, A30V, T32I, N33T, N33Y, P42L, D57A, D57N, G91V, T114I, G163K, N251S, wherein each position corresponds to a position of amino acids 1 to 269 of SEQ ID NO: 2.
8. A lipase being a variant of a parent lipase, which variant (a) has at least 50% identity to amino acids 1 to 269 of SEQ ID NO: 2; and (b) has lipase activity; and (c) is selected from the following variants:

| | |
|---|---|
| LVA012: | D27R + N33Q + G91A + D96E + L97Q + D111A + T231R + N233R + P256T, |
| LVA023: | N33Q + E210D + T231R + N233R, |
| LVA041: | N33Q + D111A + T231R + N233R, |
| LVA043: | N33Q + G91T + T231R + N233R, |
| LVA049: | N33Q + G163K + T231R + N233R, |
| LVA061: | D27Q + N33Q + T231R + N233R, |
| LVA099: | D27R + N33Q + G91T + N94S + D111A + S216P + L227G + T231R + N233R + P256T, |
| LVA349: | K98I + T231R + N233R + N251S, |
| LV1232: | G91A + D96W + E99K + G263Q + L264A + I265T + G266D + T267A + L269N, |
| LV1330: | N33Q + D96S + T231R + N233R + Q249R, |
| LV1855: | D27R + G91A + D111A + S216P + L227G + P256T, |
| LV1857: | D27R + G91N + N94R + D111A + S216P + L227G + P256T, |
| LV1865: | D27R + G91T + N94S + D111A + S216P + L227G + P256T, |
| LV1874: | D27R + G91S + D111A + S216P + L227G + P256T, |
| LV1889: | D27R + G91T + D96N + D111A + S216P + L227G + P256T, |
| LVAR0002b | T32I + G91V + T231R + N233R, |
| LVAR0003: | K98I + T231R + N233R, |
| LVAR0011a | G91A + T231R + N233R, |
| LVAR0013: | G91V + T231R + N233R, |
| LVAR0014 | N33Y + G91W + N94K + T231R + N233R, |
| LVAR0015 | P42L + D57N + G91E + T231R + N233R, |
| LVAR0016 | K98I + T231R + N233R, |
| LVAR0017 | V60L + G91V + T231R + N233R, |
| LVAR0032: | D57G + L93F + T231R + N233R, |
| LVAR0045: | A49T + E56R + E87K + E99S + T231R + N233R, |
| LVAR0046: | E99T + T114I + D254N + T231R + N233R, |
| LVAR0047: | D27Y + E87K + D96L + E99P + T231R + N233R, |
| LVAR0048 | E43K + E56S + E87K + T231R + N233R, |
| LVAR0050: | E56S ++ E87K + D96L + E99D + T231R + N233R, |
| LVAR0051: | E56A + D57A + T114I + T231R + N233R, |
| LVAR0052: | G91E + T231R + N233R, |
| LVAR0053: | E56K + D96G + D111A + T231R + N233R, |
| LVAR0054: | E87K + D111S + T231R + N233R, |
| LVAR0055 | E43V + G91R + T231R + N233R, |
| LVAR0056: | E56S + E87K + T231R + N233R, |
| LVAR0057: | E87K + G91E + T231R + N233R, |
| LVAR0058: | D27Y + E87K + T231R + N233R, |
| LVAR0059 | E43M + E87K + D96L + E99P + T231R + N233R, |
| LVAR0061: | E56K + E87K + D111A + T231R + N233R, |
| LVAR0062: | E87K + E99P + T231R + N233R, |
| LVAR0063: | E87K + D96L + E99P + T231R + N233R, |
| LVAR0064: | E56C + E87K + T231R + N233R, |
| LVAR0065: | E56R + E87K + D96L + T231R + N233R, |
| LVAR0066 | E43D + E56A + D57A + E87K + D111A + T231R + N233R, |
| LVAR0067: | E56K + E87K + D96L + E99P + T231R + N233R, |
| LVAR0068 | E87K + L147S + T231R + N233R, |
| LVAR0069: | D27Y + E87K + D96L + E99P + T231R + N233R, |
| LVAR0070 | E43D + E87K + D96L + E99P + E239V + T231R + N233R, |
| LVAR0071 | E43K + E56A + E87K + D234K + T231R + N233R, |
| LVAR0072: | D96V + D111A + T231R + N233R, |
| LVAR0074: | N33Q + E87K + T231R + N233R, |
| LVAR0076: | N33Q + N94K + T231R + N233R, |
| LVAR0077: | N33Q + D96Y + T231R + N233R, |
| LVAR0078: | N33T + E43V + E56K + D96G + T231R + N233R, |
| LVAR0079: | N33Q + K98I + T231R + N233R, |
| LVAR0080: | A30V + N33Q + K98I + T231R + N233R, |
| LVAR0086: | N33Q + E87K + D96E + T231R + N233R, |
| LVAR0088: | N26I + N33Q + T231R + N233R, |
| LVAR0091: | A30T + N33Q + T231R + N233R, |
| LVAR0094: | N33Q + G91V + T231R + N233R, |
| LVAR0095: | N33Q + G91A + T231R + N233R, |
| LVAR0096: | N33Q + G91V + L97M + T231R + N233R, |
| LVAR0099: | N33Q + K98I + T231R + N233R, |
| LVAR0101: | N33Q + L69I + G91E + T231R + N233R, |
| LVAR0102: | P29T + N33Q + T231R + N233R, |
| LVAR0103: | N33Q + G91V + T231R + N233R, |
| LVAR0104: | N33Q + K98I + T231R + N233R, |
| LVAR0106: | N33Q + G91E + T231R + N233R, and |
| LVAR0108: | N33Q + N94K + T231R + N233R, |

wherein each position corresponds to a position of amino acids 1 to 269 of SEQ ID NO: 2.

9. The lipase of any one of embodiments 1-8, in combination with a protease or an amylase, for use as a medicament.
10. The lipase of any one of embodiments 1-8, in combination with a protease and an amylase, for use as a medicament.
11. The lipase in combination with a protease and/or an amylase according to embodiment 9 or 10, wherein (i) the protease has at least 70% identity to a protease selected from the group consisting of a) a protease having amino acids 1-274 of SEQ ID NO: 3, b) a protease having amino acids 1-188 of SEQ ID NO: 4, and c) a protease having amino acids 1-188 of SEQ ID NO: 5; (ii) the amylase has at least 70% identity to an amylase selected from the group consisting of a) an amylase having amino acids 1-481 of SEQ ID NO: 6, b) an amylase having amino acids 1-481 of SEQ ID NO: 7, and c) an amylase having amino acids 1-483 of SEQ ID NO: 8.

12. Use of a lipase or a mixture of lipases as defined in any one of embodiments 1-8 for the manufacture of a medicament for the treatment of digestive disorders, pancreatic exocrine insufficiency, pancreatitis, cystic fibrosis, diabetes type I, and/or diabetes type II.
13. The use of embodiment 12, further comprising the use of a protease or an amylase.
14. The use of embodiment 12, further comprising the use of a protease and an amylase.
15. The use of embodiment 13 or 14, wherein the protease and/or amylase are as defined in embodiment 11.
16. A lipase as defined in any one of embodiments 1-8 for use in the treatment of digestive disorders, pancreatic exocrine insufficiency, pancreatitis, cystic fibrosis, diabetes type I, and/or diabetes type II.
17. The lipase of embodiment 16, in combination with a protease or an amylase.
18. The lipase of embodiment 16, in combination with a protease and an amylase.
19. The lipase of embodiment 16 or 17, wherein the protease and/or amylase are as defined in embodiment 11.
20. A pharmaceutical composition comprising a lipase or a mixture of lipases as defined in any one of embodiments 1-8, together with at least one pharmaceutically acceptable auxiliary material.
21. The composition of embodiment 20, further comprising a protease or an amylase.
22. The composition of embodiment 20, further comprising a protease and an amylase.
23. The composition of embodiment 21 or 22, wherein the protease and/or amylase are as defined in embodiment 11.
24. A method for the treatment of digestive disorders, pancreatic exocrine insufficiency, pancreatitis, cystic fibrosis, diabetes type I, and/or diabetes type II, by administering a therapeutically effective amount of a lipase or a mixture of lipases as defined in any one of embodiments 1-8.
25. The method of embodiment 24, further comprising administering a therapeutically effective amount of a protease or an amylase.
26. The method of embodiment 24, further comprising administering a therapeutically effective amount of a protease and an amylase.
27. The method of embodiment 25 or 26, wherein the protease and/or amylase are as defined in embodiment 11.

Various references are cited herein, the disclosures of which are incorporated by reference in their entireties.

EXAMPLES

Chemicals used were commercial products of at least reagent grade. De-ionized water is from the Milli-Q system (QPAK1, Millipore, catalogue no. CPMQ004R1).

Example 1

Enzyme Assays

Assays for lipase, protease and amylase activity of porcine pancreatin have been published by the FIP (Federation Internationale Pharmaceutique) as well as the European Pharmacopoeia and the United States Pharmacopeia. 1 FIP-unit=1 Ph.Eur.-unit (European Pharmacopoeia). The assays are described in, e.g.: Fédération Internationale Pharmaceutique, Scientific Section: International Commission for the standardisation of pharmaceutical enzymes. a) "Pharmaceutical Enzymes," Editors: R. Ruyssen and A. Lauwers, E. Story Scientia, Ghent, Belgium (1978), b) European Pharmacopoeia. See also Deemester et al in Lauwers A, Scharpé S (eds): Pharmaceutical Enzymes, New York, Marcel Dekker, 1997, p. 343-385. Appropriate enzyme standards can be procured from: International Commission on Pharmaceutical Enzymes, Centre for Standards, Harelbekestraat 72, B-9000 Ghent.

The lipase FIP assay as well as other suitable assays for lipase, protease and amylase is described below.

Ligase FIP Assay

For measuring lipolytic activity of pancreatin the method published in the European Pharmacopoeia 5.1 was used. Unless otherwise stated, for determination of the lipolytic activity of microbial lipases the assay for Rhizopus oryzae lipase published by the FIP was used.

Ligase pNP Assay

Substrate: para-Nitro-Phenyl (pNP) Valerate

Assay pH: 7.7

Assay temperature: 40° C.

Reaction time: 25 min

The digested product with yellow colour has a characteristic absorbance at 405 nm. Its quantity is determined by spectrophotometry. The lipase activity may be determined relative to an enzyme standard of known activity. The activity may be expressed in Lipolase Units (LU). One LU (Lipolase Unit) is the amount of enzyme which releases 1 mmol titratable butyric acid per minute under the above standard conditions. 1 KLU=1000 LU. A more detailed assay description, AF95/6-GB (Lipase/Esterase—pH-STAT Method on a Tributyrin Substrate (LU)), as well as a LU standard, is available on request from Novozymes A/S, Krogshoejvej 36, DK-2880 Bagsvaerd, Denmark.

Lipase LU Assay

In this assay, the lipase-catalysed degradation of 0.16 M tributyrin (glycerol tributyrate, Merck 1.01958.000) at pH 7.00 and 30° C. (±1° C.) is followed by pH-stat titration of released butyric acid with 0.025 M degassed, $CO_2$-free sodium hydroxide (Sodium hydroxide titrisol, Merck 9956). The consumption of the titrant is recorded as a function of time.

The substrate is emulsified with a 0.6% w/v Gum arabic emulsifier (20.0 g Gum Arabic, 89.5 g NaCl, 2.05 g $KH_2PO_4$, add water to 1.5 l, leave until completely dissolved, add 2700 ml glycerol, adjust pH to 4.5. 90 ml of tributyrin is mixed with 300 ml gum arabic emulsifier and 1410 ml demineralised water and homogenised for 3 minutes using e.g. a Silverson emulsifier L4RT at 7000 rpm and then adjusted to pH 4.75). Lipase-samples are diluted first in 0.1 M glycin buffer pH 10.8, next in demineralized water, aiming at an activity level of 1.5-4.0 LU/ml. 15 ml of the emulsified substrate solution is poured into the titration vessel. 1.0 ml sample solution is added, and pH is maintained at 7.0 during the titration. The amount of titrant added per minute to maintain a constant pH is measured. The activity calculation is based on the mean slope of the linear range of the titration curve. A standard of known activity may be used as a level check.

1 LU (lipase unit) is the amount of enzyme which releases 1 micro mole titratable butyric acid per minute under the assay conditions given above. 1 kLU (kilo Lipase Unit)=1000 LU.

A more detailed assay description, EB-SM-0095.02, is available on request from Novozymes A/S, Krogshoejvej 36, DK-2880 Bagsvaerd, Denmark.

Lipase pH Stat Assay

This assay is based on the lipase-catalysed release of fatty acids from an olive oil emulsion in the presence of 0.65 mM bile salts. The substrate is emulsified with gum arabic as emulsifier (175 g olive oil emulsified with 630 ml gum arabic solution (474.6 g gum arabic, 64 g calcium chloride in 4000 ml water) for 15 min in a blender; after cooling to room temperature, pH is adjusted to pH 6.8-7.0 using 4 M NaOH).

For the determination, 19 ml of the emulsion and 10 ml bile salts solution (492 mg bile salts are dissolved in water and filled up to 500 ml) are mixed in the reaction vessel and heated to 36.9° C. to 37.5° C. Reaction is started by addition of 1.0 ml of enzyme solution. The released acid is titrated automatically at pH 7.0 by addition of 0.1 M sodium hydroxide for a total of 5 min. The activity is calculated from the slope of the titration curve between the 1st and the 5th minute. For calibration, a standard is measured at three different levels of activity.

Protease Suc-AAPF-pNA Assay

Substrate: Suc-AAPF-pNA (Sigma S-7388).

Assay buffer: 100 mM succinic acid, 100 mM HEPES (Sigma H-3375), 100 mM CHES (Sigma C-2885), 100 mM CABS (Sigma C-5580), 1 mM $CaCl_2$, 150 mM KCl, 0.01% Triton-X100 (a nonionic surfactant having the molecular formula: $C_{14}H_{22}O(C_2H_4O)_n$ where the average number of ethylene oxide units per molecule is around 9 or 10, CAS #: 9002-93-1) adjusted to pH 9.0 with HCl or NaOH.

Assay temperature: 25° C.

300 microliters diluted protease sample was mixed with 1.5 ml of the assay buffer and the activity reaction was started by adding 1.5 ml pNA substrate (50 mg dissolved in 1.0 ml DMSO and further diluted 45× with 0.01% Triton-X100) and, after mixing, the increase in $A_{405}$ was monitored by a spectrophotometer as a measurement of the protease activity. The protease samples were diluted prior to the activity measurement in order to ensure that all activity measurements fell within the linear part of the dose-response curve for the assay.

Protease AU Assay

Denatured haemoglobin (0.65% (w/w) in urea-containing 6.7 mM $KH_2PO_4$/NaOH buffer, pH 7.50) is degraded at 25° C. for 10 minutes by the protease and un-degraded haemoglobin is precipitated with trichloroacetic acid (TCA) and removed by filtration. The TCA-soluble haemoglobin degradation products in the filtrate are determined with Folin & Ciocalteu's phenol reagent (1 volume of Folin-Ciocalteu Phenol Reagent Merck 9001.0500 to 2 volumes of demineralised water), which gives a blue colour with several amino acids (being measured at 750 nm). The activity unit (AU) is measured and defined by reference to a standard. The denatured haemoglobin substrate may be prepared as follows: 1154 g urea (Harnstoff, Merck 8487) is dissolved in 1000 ml demineralised water, 240.3 g NaOH is added and then, slowly, 63.45 g haemoglobin (Merck 4300) is added, followed by 315.6 g $KH_2PO_4$, and demineralised water ad 3260 g. pH is adjusted to 7.63. More details and a suitable Alcalase standard are available on request from Novozymes A/S, Krogshoejvej 36, DK-2880 Bagsvaerd, Denmark (assay no. EB-SM-0349.01).

Amylase

Substrate: Phadebas tablets (Pharmacia Diagnostics; cross-linked, insoluble, blue-coloured starch polymer, which is mixed with bovine serum albumin and a buffer substance, and manufactured into tablets)

Assay Temperature: 37° C.

Assay pH: 4.3 (or 7.0, if desired)

Reaction time: 20 min

After suspension in water the starch is hydrolyzed by the alpha-amylase, giving soluble blue fragments. The absorbance of the resulting blue solution, measured at 620 nm, is a function of the alpha-amylase activity. The alpha-amylase activity may be determined relative to a standard of known activity, e.g. expressed in Fungal alpha-Amylase Units (FAU). One FAU is the amount of enzyme which breaks down 5.26 g starch (Merck, Amylum solubile Erg. B. 6, Batch 9947275) per hour at the standard assay conditions. A more detailed assay description, APTSMYQI-3207, and a FAU standard, is available on request from Novozymes A/S, Krogshoejvej 36, DK-2880 Bagsvaerd, Denmark.

Example 2

Lipase Variants with Improved Phospholipase Activity

DNA encoding the lipase variants shown in Table 1 below was transformed into *Aspergillus oryzae* strain ToC1512 (described in WO 2005/070962), using the method described in Example 22 of U.S. Pat. No. 5,869,438, except that PyrG selection was used (described in WO 2004/069872) instead of AMDS selection. Spores of the Aspergillus oryzae host were taken from an agar slant and used for inoculation of 10 ml YPM (10 g yeast extract, Difco+20 g Peptone, Difco, water to 1 L, is autoclaved; add sterile filtered maltose to 2% (w/w)). Inoculated tubes were incubated at 30° C. for three days in a New Brunswick Scientific Innova 2300 shaker at 180 rpm. Supernatants were harvested by filtering cultures with Mira-Cloth (Calbiochem) followed by sterile filtration with 0.45 um (micro meter) filters. The lipase variants were purified as generally described in Example 23 of U.S. Pat. No. 5,869,438.

TABLE 1

Lipase variants I

| Variant designation | Substitutions as compared to SEQ ID NO: 2 |
|---|---|
| LVA012 | D27R + N33Q + G91A + D96E + L97Q + D111A + T231R + N233R + P256T |
| LVA023 | N33Q + E210D + T231R + N233R |
| LVA041 | N33Q + D111A + T231R + N233R |
| LVA043 | N33Q + G91T + T231R + N233R |
| LVA049 | N33Q + G163K + T231R + N233R |
| LVA061 | D27Q + N33Q + T231R + N233R |
| LVA099 | D27R + N33Q + G91T + N94S + D111A + S216P + L227G + T231R + N233R + P256T |
| LVA103 | Q4R + N33Q + T231R + N233R |
| LVA120 | N33Q + D96W + T231R + N233R |
| LVA349 | K98I + T231R + N233R + N251S |
| LV1330 | N33Q + D96S + T231R + N233R + Q249R |
| LV1855 | D27R + G91A + D111A + S216P + L227G + P256T |
| LV1857 | D27R + G91N + N94R + D111A + S216P + L227G + P256T |
| LV1865 | D27R + G91T + N94S + D111A + S216P + L227G + P256T |
| LV1874 | D27R + G91S + D111A + S216P + L227G + P256T |
| LV1889 | D27R + G91T + D96N + D111A + S216P + L227G + P256T |
| LV2934 | N33Q + T231R + N233R |

The following lipases were used for comparison and were also prepared as described above:

The wild type lipase from *Humicola lanuginosa DSM* 1800 having the sequence of amino acids 1-269 of SEQ ID NO: 2 and described for pharmaceutical use in, e.g., U.S. Pat. No. 5,614,189), and the (T231R+N233R)-variant thereof having amino acids 1-269 of SEQ ID NO: 1, described for pharmaceutical use in WO 2006/136159.

The following lipase serves as a positive control (positive for phospholipase activity):

Variant LV1232 with the following substitutions as compared to SEQ ID NO: 2: G91A+D96W+E99K+G263Q+L264A+1265T+G266D+T267A+L269N.

These lipases were tested for phospholipase activity as described in the following. Enzymes:

The enzyme samples were diluted in enzyme dilution buffer (20 mM Na-Acetate, 0.01% w/w Triton-X100, pH 5.0) to 5 mg/mL (mg of enzyme protein (EP) per ml). The enzyme concentrations were determined on the basis of $A_{280}$ and the calculated molar absorption coefficient (program GPMAW (Lighthouse Data, Odense, Denmark; available on the Internet at welcome.to/gpmaw; see also Gill and von Hippel, 1989, Calculation of protein extinction coefficients from amino acid sequence data, *Anal. Biochem.* 182: 319-326).

Substrate:

A solution of the substrate 1-myristoyl-2-palmitoyl-sn-glycero-3-phosphocholine (in what follows "phosphatidylcholine"), which is commercially available from Avanti Polar Lipids Inc., 700 Industrial Park Drive, Alabaster, Ala. 35007, US, catalogue no. 850445) was prepared as follows:

1 137.5 mg phosphatidylcholine is dissolved in 750 uL (microliter) de-ionized water
2 Stir 1 h at room temperature
3 Add 37.5 uL 0.32 M $CaCl_2$
4 Stir for 1-2 minutes
5 Add 375 uL 16 mM sodium deoxycholate
6 Add 750 uL de-ionized water
7 Stir for 30 minutes at room temperature Enzyme Reaction:

1 Transfer 100 uL substrate to 2 mL-eppendorf tubes
2 Add 5 uL enzyme, diluted to 5 mg/mL as described above
3 Incubate for 20 minutes at 40° C., 1000 rpm in an eppendorf thermomixer
4 Transfer 10 uL reaction mixture to a new eppendorf tube and add 990 uL 50% methanol (MeOH), 0.1% (w/w) trifluoroacetic acid (TFA)
5 This is analysed by MALDI-TOF MS (Matrix-Assisted Laser Desorption/Ionization Time-Of-Flight mass spectrometry), after mixing with this matrix: 20 mg/mL 2,5-dihydrobenzoic acid in 50% MeOH, 0.1% TFA A substrate control was included, in which 5 uL enzyme dilution buffer was added instead of enzyme in step 2. Four independent determinations were made for each sample in step 5. The MALDI-TOF MS apparatus used was a Voyager DE PRO instrument with positive ionisation in reflector mode with external calibration (Calmix 2, Applied Biosystems).

By choosing a glycerol-based substrate with ester-bonded acids of different length it is possible to distinguish between enzymatic specificities (attack at the 1-position or 2-position) by measuring the mass of the digested glycerol backbone. The masses of the various possible digested glycerol backbones are:

| | |
|---|---|
| 706 Da | Phosphatidylcholine |
| 496 Da | A1 hydrolysis (phosphatidylcholine minus myristoyl (C14) in position 1) |
| 468 Da | A2 hydrolysis (phosphatidylcholine minus palmitoyl (C16) in position 2) |
| 258 Da | A1 and A2 hydrolysis (undegraded phosphatidylcholine minus C14 and C16) |

Results:

The relative signal intensities (area under each peak) of the MS peaks representing Mw's of 706, 496, 468, and 258Da are used as basis for the calculation of the distribution between Phospholipase A1 and A2 (PLA1- and PLA2-) activity.

The results, from two different experiments (I and II), are shown in Tables 2 and 3 below.

Generally, a signal intensity of above 10-15% of A1/A2 relative to A2/A1 may indicate either true dual activity or an impure sample.

TABLE 2

Experiment I: Phospholipase activity of lipase variants

| Enzyme tested | Distribution of activity PLA-1 % | PLA-2 % | % undigested phospholipid left after hydrolysis |
|---|---|---|---|
| SEQ ID NO: 1 | 72 | 28 | 44 |
| SEQ ID NO: 2 | 78 | 22 | 42 |
| LVA012 | 66 | 34 | 65 |
| LVA023 | 78 | 22 | 40 |
| LVA041 | 79 | 21 | 55 |
| LVA061 | 73 | 27 | 46 |
| LVA099 | 71 | 29 | 45 |
| LVA103 | 69 | 31 | 68 |
| LVA349 | 80 | 20 | 46 |
| LVA120 | 75 | 25 | 47 |
| LV1889 | 63 | 37 | 26 |
| LV2934 | 60 | 40 | 62 |
| LV1232 | 68 | 32 | 1.4 |
| Substrate control | | | 82 |

TABLE 3

Experiment II: Phospholipase activity of lipase variants

| Enzyme tested | Distribution of activity PLA-1 % | PLA-2 % | % undigested phospholipid left after hydrolysis |
|---|---|---|---|
| SEQ ID NO: 1 | 73 | 27 | 82 |
| LV1330 | 86 | 15 | 54 |
| LV1855 | 84 | 16 | 58 |
| LV1865 | 78 | 22 | 65 |
| LV1874 | 84 | 17 | 56 |
| LV1889 | 89 | 11 | 4.6 |
| LVA043 | 82 | 18 | 51 |
| LVA049 | 82 | 18 | 50 |
| LV1857 | 86 | 14 | 42 |
| LV1232 | 91 | 9.3 | 1.3 |
| Substrate control | | | 100 |

Conclusion:

All lipases tested have phospholipase activity to some extent, primarily as PLA1-activity. The positive control, LV1232, showed a high phospholipase activity in both experiments.

The prior art lipases of SEQ ID NOS: 1 and 2 showed almost the same performance as regards phospholipase activity when tested in the same experiment (Experiment I), leaving approximately 44% and 42%, respectively, undigested phospholipid after hydrolysis.

It is contemplated that the following lipase variants have an improved phospholipase activity as compared to SEQ ID NO: 2: LV1232, LV1889 and LVA023 (Experiment I), and LV1232, LV1330, LV1855, LV1865, LV1874, LV1889, LVA043, LVA049, and LV1857 (Experiment II). Variant LV1232 and LV1889 in particular show a very much improved phospholipase activity in both experiments.

Example 3

Lipase Variants with Improved Activity at pH 6

A number of the purified lipase variants shown in Table 1 above were tested for activity at pH 6 in the presence of 10 mM bile salt. Like in Example 1, the lipases of SEQ ID NO: 2 and 1 were included for comparison.

Chemicals and Reagents:

Assay buffer pH 6: 100 mM imidazole, 100 mM acetate, 100 mM malonic acid, pH 6.0

Enzyme dilution buffer: 5 mM $NaH_2PO_4$ pH 7.0

7 mM $CaCl_2$ (Merck, 1.02382.0500)

Bile salts (80 mM): Lipase activating bile salt mixture from Solvay Pharmaceuticals, batch 176.01-PA-7374

Trilinolein (glyceryl trilinoleate, Sigma T9517)

Pepsin: (Merck VL 317492437, catalogue no. 1.0792.0001)

Stop solution: 10% Triton-X100, 1 M Phosphoric acid.

Substrate:

Substrate working emulsion was prepared as followed:

1. Mix 2.188 mL bile salts (80 mM) with 6.68 mL de-ionized water.
2. Add 0.133 mL Trilinolein (glyceryl trilinoleate, Sigma T9517).
3. Mix 1 minute with ultraturex mixer (yellow line DI 25 basic) at room temperature.

This gives a working emulsion of substrate with 19.44 mM bile salts and 15.56 mM Trilinolein.

Enzymes:

The enzyme samples were diluted in 5 mM $NaH_2PO_4$ pH 7.0 to 0.07 mg/mL (mg of enzyme protein per ml). The enzyme concentrations were based on $A_{280}$. Enzymes were two-fold diluted in 5 mM $NaH_2PO_4$ (six dilutions made in total and no enzyme/buffer control). These dilutions give the following final concentrations of enzyme in the wells: 0.01 mg/ml, 0.05, 0.025, 0.0125, 0.0625, 0.03125, and 0.015625 mg/ml.

Assay Procedure:

1. Mix in Micro Titer Plates (MTP) 35 ul (micro liter) assay buffer with 25 ul 7 mM $CaCl_2$. Add 90 ul substrate working emulsion. Pre-incubate for 20 min at 37° C., 700 rpm.
2. Add 25 ul of the respective enzyme dilutions, and incubate 30 min at 37° C., 700 rpm (final volume 175 ul). Final concentration of bile salts and trilinolein is 10 mM and 8 mM, respectively, in MTP well.
3. Add 50 ul stop solution (10% Triton-X100, 1 M Phosphoric acid) and 25 ul pepsin (700 mg/l). Incubate 10 min at room temperature. The pepsin, which is a protease, is added in order to avoid re-activation of the lipase protein when the pH is increased in the subsequent procedure (the determination of free fatty acids (FFA)).
4. Dilute samples immediately 10 times in 1% Triton-X100 for detection of FFA by NefaC (Wako, Nefa C ACS-ACOD Method Enzymatic color test Code No: 999-75406).

Detection of free fatty acids by NefaC kit (Nefa C ACS-ACOD Method Enzymatic color test Code No: 999-75406):

1. Make solution A: Bottle R1a is dissolved with 10 ml of bottle R1 (from NefaC kit)

Make solution B: Bottle R2a is dissolved with 20 ml of bottle R2 (from NefaC kit)

2. Call Nefa C standard Oleic acid (28.2 mg/dl-1 mmol/L) is diluted in 1% Triton-X100 to obtain the following concentrations for NefaC standard: 1 mM, 0.5, 0.25, 0.125, 0.0625, 0.03125, and 0.015625 mM.
3. 25 ul standard/lipase sample is mixed with 50 ul solution A. Incubate 15 min at room temperature, 700 rpm.
4. Add 100 ul solution B, incubation 15 min room temperature, 700 rpm.

Results:

The concentration of FFA in mM is determined from the Nefa C standard curve. The lipase activity results are fitted to Michealis-Menten-like fit:

$$A=A0+A\max*[E]/([E]+K)$$

V0 is determined (mmol FFA/g enzyme/min), and the ratio to the V0 for the lipase of SEQ ID NO: 1 is determined. The lipase of SEQ ID NO: 1 and variant LV2934 (a non-glycosylated variant of SEQ ID NO: 1) were included on each MTP as controls.

The results, normalized to SEQ ID NO: 1, are shown in Table 4 below.

TABLE 4

Lipase activity at pH 6 on trilinoleate

| Enzyme tested | Relative V0 (mmol FFA/g enzyme/min) |
|---|---|
| SEQ ID NO: 2 | 0.35 |
| LVA049 | 1.45 |
| LVA349 | 1.10 |
| LVA023 | 1.06 |
| LVA099 | 1.02 |
| SEQ ID NO: 1 (I) | 1.00 |
| SEQ ID NO: 1 (II) | 1.00 |
| SEQ ID NO: 1 (III) | 1.00 |
| LVA061 | 0.90 |
| LV2934-I | 0.80 |
| LV2934-II | 0.77 |
| LV2934-III | 0.73 |
| LV1330 | 0.79 |
| LVA043 | 0.75 |
| LVA041 | 0.72 |
| LVA012 | 0.64 |
| LV1857 | 0.47 |
| LV1855 | 0.36 |
| LV1889 | 0.34 |
| LV1874 | 0.33 |
| LV1865 | 0.23 |

Conclusion:

On the basis of the above results it is contemplated that, except for LV1889, LV1874 and LV1865, all variants tested have a higher activity at pH 6 using trilinoleate substrate with 10 mM bile salts, as compared to the lipase of SEQ ID NO: 2.

The LVA049, LVA349, LVA023, and LVA099 lipase variants seem much better than the comparative lipase of SEQ ID NO: 2 in this respect, in fact better than the SEQ ID NO: 1 lipase. This is so in particular for the LVA049 and LVA349 lipase variants, more in particular for the LVA049 lipase variant.

Example 4

Lipase Variants with Improved Stability at pH 3

A number of the lipase variants listed in Table 1 above were tested for pH stability in the pH range of 2-8. Like in the previous Examples, the lipases of SEQ ID NO: 2 and 1 were included for comparison. The following variants of the lipase of SEQ ID NO: 2 were also tested:

| | |
|---|---|
| LVA147: | D27R + N33Q + G91N + N94R + D111A + S216P + L227G + T231R + N233R + P256T |
| LVA315: | N33Q + G91T + G163K + T231R + N233R + D254G |

-continued

| | |
|---|---|
| LVA317: | N33Q + G91T + G163K + T231R + N233R + D254S |
| LVA319: | N11R + N33Q + G91T + G163K + T231R + N233R + D254S |
| LVA714: | D27V + N33Q + G91A + N94R + D111A + G163K + L227F + T231R + N233R + Q249R + D254S |

Each enzyme was tested in duplicate, in two concentrations (0.05 and 1.0 mg enzyme protein/ml). In addition, the enzymes were tested with and without bile salts 10 mM, and with and without pepsin (70 mg/l).

In brief, the enzymes were incubated at 37° C. at the desired pH for 1, 15, 45, and 120 minutes (or for 1, 60, and 120 minutes), following which residual lipase activity was measured on p-Nitrophenyl caprylate at pH 8 and room temperature (RT).

Chemicals/Reagents:

Enzyme dilution buffer: 20 mM acetate pH 6, 0.01% Triton-X100.

Stability buffer: 200 mM imidazole, 200 mM acetate, 200 mM malonic acid, adjusted to pH 2.0, 3.0, 4.0, 5.0, 6.0, 7.0, and 8.0.

Residual activity buffer (RA buffer): 200 mM Tris (tris-hydroxymethyl aminomethan, 2-amino-2-hydroxymethyl-1,3-propandiol, CAS-number: 77-86-1) pH 8, 0.4% Triton-X100, 1 mM $CaCl_2$ pNP-caprylate (C8): Sigma N-0752

Pepsin (700 mg/l): Merck, VL 317492437 (1.0792.0001)

Bile salts (80 mM): Lipase activating bile salt mixture from Solvay Pharmaceuticals (batch 176.01-PA-7374)

Enzymes:

Enzymes were diluted in 20 mM $NaH_2PO_4$ pH 7.0, 0.01% Triton-X100 to working solutions of 0.4 or 0.8 mg enzyme protein per ml, based on $A_{280}$.

Stability Assay:

1) To each well of a microtiter plate (MTP) add 50 ul stability buffer, 20 ul 0.1% Triton-X100, 25 ul bile salts (80 mM) or 20 ul pepsin (700 mg/l) or de-ionized water. Add de-ionized water to a final volume of 175 ul per well. All samples are made in duplicate. Preheat at 37° C. for 20 min, 700 rpm.
2) Add 25 ul enzyme (final concentration 0.05 or 0.1 mg enzyme protein per ml). For each pH no enzyme controls with pepsin and bile salts are included, ie. 25 ul 20 mM $NaH_2PO_4$pH 7.0, 0.01% Triton-X100 is added to these wells. Incubate at 37° C. 700 rpm for 1, 15, 45 and 120 min.
3) Withdraw aliquots of 20 ul and dilute sample with 180 ul residual activity buffer pH 8.0, keep samples on ice.
4) Dilute sample (minimum dilution 20× to increase pH to 8). Make initial residual activity (RA) on 1 min samples pH 8, diluted 20×, 40×, 80×, 160×, and 320× to determine dilution required to obtain linearity in assay.
5) Measure RA with pNP-caprylate substrate at pH 8.0 as described below.

Substrate:

Substrate stock solution is prepared by mixing 14.2 ul p-Nitrophenyl caprylate (Sigma N-0752) with 1 ml 2-propanol. This stock solution is diluted 50× in residual activity buffer pH8.0 giving a working solution of which 150 ul is added to each well.

Procedure for Determining Residual Activity (RA):

1) Mix in new MTP 20 ul diluted sample and 150 ul substrate working solution.
2) Measure kinetics at 405 nm for 5 min (mix first time, read every 12 sec, room temperature).

Results:

The % residual activity is calculated as follows: The rate within each pH for each withdraw (1, 15, 45, 120 minutes) is subtracted the rate for no enzyme control with bile salts or pepsin. This corrected rate is then divided by the highest value within each pH and multiplied by 100.

Table 5 below shows the stability at pH 3 for those variants that are improved as compared to SEQ ID NO: 2 (in buffer, in the presence of pepsin, or in the presence of bile salts, respectively). Only the stability results at pH 3 are shown, as the most pronounced differences were observed at this pH.

TABLE 5

Lipase variant residual activity after pre-incubation at pH 3

| Lipase | Time Std. dev. | Buffer | Pepsin | Bile salts | Lipase | Time Std. dev. | Buffer | Pepsin | Bile salts |
|---|---|---|---|---|---|---|---|---|---|
| SEQ ID NO: 2 | 1 min | 100.0 | 100.0 | 100.0 | LVA049 | 1 min | 100.0 | | |
| | std dev | 2.6 | 9.6 | 1.1 | | std dev | 4.9 | | |
| | 15 min | 82.6 | 2.1 | 5.2 | | 15 min | 92.0 | | |
| | std dev | 1.2 | 0.7 | 4.6 | | std dev | 5.3 | | |
| | 45 min | 80.9 | 1.6 | 2.0 | | 45 min | 85.4 | | |
| | std dev | 2.9 | 0.8 | 1.7 | | std dev | 5.8 | | |
| | 120 min | 59.0 | −1.2 | −0.2 | | 120 min | 74.6 | | |
| | std dev | 4.9 | 1.2 | 0.3 | | std dev | 7.1 | | |
| SEQ ID NO: 1 | 1 min | 100.0 | 100.0 | 100.0 | LV1855 | 1 min | 100.0 | 100.0 | |
| | std dev | 3.1 | 2.2 | 6.5 | | std dev | 0.7 | 2.4 | |
| | 15 min | 72.2 | 1.1 | 39.2 | | 15 min | 92.1 | 90.4 | |
| | std dev | 0.5 | 0.1 | 0.2 | | std dev | 1.3 | 0.6 | |
| | 45 min | 62.2 | 0.1 | 20.5 | | 45 min | 90.6 | 67.5 | |
| | std dev | 0.3 | 0.0 | 3.1 | | std dev | 0.0 | 3.2 | |
| | 120 min | 59.2 | 0.0 | 10.5 | | 120 min | 88.4 | 31.5 | |
| | std dev | 1.3 | 0.0 | 1.4 | | std dev | 3.1 | 2.2 | |
| LV2934 | 1 min | 100.0 | | | LV1865 | 1 min | 100.0 | 100.0 | 100.0 |
| | std dev | 2.5 | | | | std dev | 3.8 | 0.4 | 0.7 |
| | 15 min | 84.9 | | | | 15 min | 92.5 | 85.0 | 50.2 |
| | std dev | 0.5 | | | | std dev | 0.4 | 0.9 | 1.3 |
| | 45 min | 73.9 | | | | 45 min | 92.8 | 66.5 | 36.4 |
| | std dev | 0.4 | | | | std dev | 0.1 | 1.1 | 0.4 |
| | 120 min | 62.6 | | | | 120 min | 92.7 | 30.3 | 14.6 |
| | std dev | 1.1 | | | | std dev | 0.7 | 0.5 | 1.3 |

TABLE 5-continued

| Lipase variant residual activity after pre-incubation at pH 3 | | | | | | | | | |
|---|---|---|---|---|---|---|---|---|---|
| Lipase | Time Std. dev. | Buffer | Pepsin | Bile salts | Lipase | Time Std. dev. | Buffer | Pepsin | Bile salts |
| LVA043 | 1 min | 100.0 | 100.0 | | LV1874 | 1 min | 100.0 | 100.0 | |
| | std dev | 3.4 | 1.5 | | | std dev | 7.0 | 3.8 | |
| | 15 min | 91.2 | 51.0 | | | 15 min | 84.9 | 72.3 | |
| | std dev | 2.7 | 9.6 | | | std dev | 1.4 | 5.1 | |
| | 45 min | 91.7 | 34.3 | | | 45 min | 89.7 | 60.5 | |
| | std dev | 3.4 | 6.1 | | | std dev | 2.6 | 1.9 | |
| | 120 min | 83.4 | 25.1 | | | 120 min | 87.9 | 23.6 | |
| | std dev | 3.1 | 5.1 | | | std dev | 1.7 | 1.9 | |
| LV1889 | 1 min | 100.0 | 100.0 | | LVA041 | 1 min | 100.0 | | |
| | std dev | 5.2 | 3.1 | | | std dev | 3.0 | | |
| | 15 min | 97.4 | 68.2 | | | 15 min | 85.3 | | |
| | std dev | 6.0 | 6.2 | | | std dev | 2.9 | | |
| | 45 min | 92.8 | 36.0 | | | 45 min | 80.1 | | |
| | std dev | 9.4 | 5.4 | | | std dev | 3.7 | | |
| | 120 min | 88.0 | 7.8 | | | 120 min | 69.6 | | |
| | std dev | 5.7 | 2.8 | | | std dev | 5.9 | | |
| LV1857 | 1 min | 100.0 | 100.0 | | LVA061 | 1 min | 100.0 | | |
| | std dev | 4.0 | 5.3 | | | std dev | 3.1 | | |
| | 15 min | 95.8 | 80.3 | | | 15 min | 87.8 | | |
| | std dev | 0.7 | 2.2 | | | std dev | 2.9 | | |
| | 45 min | 94.5 | 54.2 | | | 45 min | 83.0 | | |
| | std dev | 1.8 | 2.4 | | | std dev | 7.0 | | |
| | 120 min | 72.4 | 17.8 | | | 120 min | 77.6 | | |
| | std dev | 3.2 | 1.1 | | | std dev | 7.2 | | |
| LVA012 | 1 min | 100.0 | 100.0 | | LVA099 | 1 min | 100.0 | 100.0 | |
| | std dev | 6.0 | 1.4 | | | std dev | 4.0 | 2.8 | |
| | 15 min | 98.3 | 83.1 | | | 15 min | 93.3 | 93.8 | |
| | std dev | 6.4 | 1.0 | | | std dev | 3.7 | 1.4 | |
| | 45 min | 88.2 | 54.8 | | | 45 min | 89.9 | 95.2 | |
| | std dev | 4.6 | 1.3 | | | std dev | 3.4 | 1.2 | |
| | 120 min | 78.4 | 20.1 | | | 120 min | 74.7 | 94.0 | |
| | std dev | 5.5 | 1.7 | | | std dev | 9.0 | 2.4 | |
| LVA023 | 1 min | 100.0 | | | LVA349 | 1 min | | | 100.0 |
| | std dev | 3.1 | | | | std dev | | | 8.2 |
| | 15 min | 94.7 | | | | 15 min | | | 44.2 |
| | std dev | 5.2 | | | | std dev | | | 12.2 |
| | 45 min | 88.8 | | | | 45 min | | | 24.2 |
| | std dev | 5.5 | | | | std dev | | | 13.3 |
| | 120 min | 83.7 | | | | 120 min | | | 31.2 |
| | std dev | 7.2 | | | | std dev | | | 18.3 |
| LVA147 | 1 min | 100.0 | | | LVA714 | 1 min | 100.0 | 100.0 | |
| | std dev | 2.2 | | | | std dev | 2.9 | 0.9 | |
| | 60 min | 20.1 | | | | 60 min | 89.1 | 70.9 | |
| | std dev | 1.4 | | | | std dev | 0.5 | 3.3 | |
| | 120 min | 4.7 | | | | 120 min | 84.7 | 54.4 | |
| | std dev | 0.4 | | | | std dev | 0.5 | 3.6 | |
| LVA319 | 1 min | | 100.0 | | | | | | |
| | std dev | | 6.3 | | | | | | |
| | 15 min | | 68.4 | | | | | | |
| | std dev | | 8.2 | | | | | | |
| | 45 min | | 28.5 | | | | | | |
| | std dev | | 11.2 | | | | | | |
| | 120 min | | 6.3 | | | | | | |
| | std dev | | 4.8 | | | | | | |
| LVA315 | 1 min | | 100.0 | | LVA317 | 1 min | | 100.0 | |
| | std dev | | 4.8 | | | std dev | | 3.2 | |
| | 15 min | | 27.2 | | | 15 min | | 63.5 | |
| | std dev | | 9.1 | | | std dev | | 6.1 | |
| | 45 min | | 5.3 | | | 45 min | | 27.5 | |
| | std dev | | 5.0 | | | std dev | | 9.5 | |
| | 120 min | | 0.9 | | | 120 min | | 3.6 | |
| | std dev | | 1.0 | | | std dev | | 2.5 | |

Conclusion:

The following lipase variants have an improved stability at pH 3, compared to the lipase of SEQ ID NO: 2: LV2934, LVA043, LVA049, LV1855, LV1865, LV1874, LV1889, LV1857, LVA012, LVA023, LVA041, LVA061, LVA099, LVA147, and LVA714.

The following lipase variants have an improved stability at pH 3 with pepsin, compared to the lipase of SEQ ID NO: 2: LVA043, LV1855, LV1865, LV1874, LV1889, LV1857, LVA012, LVA099, LVA315, LVA317, LVA319, and LVA714.

The following variants have an improved stability at pH 3 with bile salts, compared to the lipase of SEQ ID NO: 2: LVA349.

Example 5

Micro-Purification of Lipase Variants

Additional lipase variants shown in Table 6 below were prepared as described in Example 2, up to and including the sterile filtration of the fermentation supernatant.

TABLE 6

Lipase variants II

| Variant designation | Substitutions as compared to SEQ ID NO: 2 |
|---|---|
| LVAR0003 | K98I + T231R + N233R |
| LVAR0013 | G91V + T231R + N233R |
| LVAR0032 | D57G + L93F + T231R + N233R |
| LVAR0045 | A49T + E56R + E87K + E99S + T231R + N233R |
| LVAR0046 | E99T + T114I + D254N + T231R + N233R |
| LVAR0047 | D27Y + E87K + D96L + E99P + T231R + N233R |
| LVAR0050 | E56S + E87K + D96L + E99D + T231R + N233R |
| LVAR0051 | E56A + D57A + T114I + T231R + N233R |
| LVAR0052 | G91E + T231R + N233R |
| LVAR0053 | E56K + D96G + D111A + T231R + N233R |
| LVAR0054 | E87K + D111S + T231R + N233R |
| LVAR0056 | E56S + E87K + T231R + N233R |
| LVAR0057 | E87K + G91E + T231R + N233R |
| LVAR0058 | D27Y + E87K + T231R + N233R |
| LVAR0061 | E56K + E87K + D111A + T231R + N233R |
| LVAR0062 | E87K + E99P + T231R + N233R |
| LVAR0063 | E87K + D96L + E99P + T231R + N233R |
| LVAR0064 | E56C + E87K + T231R + N233R |
| LVAR0065 | E56R + E87K + D96L + T231R + N233R |
| LVAR0067 | E56K + E87K + D96L + E99P + T231R + N233R |
| LVAR0069 | D27Y + E87K + D96L + E99P + T231R + N233R |
| LVAR0072 | D96V + D111A + T231R + N233R |
| LVAR0074 | N33Q + E87K + T231R + N233R |
| LVAR0076 | N33Q + N94K + T231R + N233R |
| LVAR0077 | N33Q + D96Y + T231R + N233R |
| LVAR0078 | N33T + E43V + E56K + D96G + T231R + N233R |
| LVAR0079 | N33Q + K98I + T231R + N233R |
| LVAR0080 | A30V + N33Q + K98I + T231R + N233R |
| LVAR0086 | N33Q + E87K + D96E + T231R + N233R |
| LVAR0088 | N26I + N33Q + T231R + N233R |
| LVAR0091 | A30T + N33Q + T231R + N233R |
| LVAR0094 | N33Q + G91V + T231R + N233R |
| LVAR0095 | N33Q + G91A + T231R + N233R |
| LVAR0096 | N33Q + G91V + L97M + T231R + N233R |
| LVAR0099 | N33Q + K98I + T231R + N233R |
| LVAR0101 | N33Q + L69I + G91E + T231R + N233R |
| LVAR0102 | P29T + N33Q + T231R + N233R |
| LVAR0103 | N33Q + G91V + T231R + N233R |
| LVAR0104 | N33Q + K98I + T231R + N233R |
| LVAR0106 | N33Q + G91E + T231R + N233R |
| LVAR0108 | N33Q + N94K + T231R + N233R |

The Sterile filtered lipase-containing culture supernatants were micro-purified using the following protocol:

To the wells of a filter plate (Unifilter 800, 25 um (micro meter) melt blown polypropylene filter, Whatman) approximately 50 ul (micro liter) XpressLine ProA chromatographic medium was added (commercially available from Upfront Chromatography A/S, Lersoe Parkalle 42, DK-2100 Copenhagen, Denmark). The chromatographic medium was equilibrated by adding 200 ul 1 M sodium acetate, pH 5.0. After 10 min agitation the equilibration buffer was removed by vacuum (Uni-Vac 3, Whatman). The equilibration step was repeated. Then 100 ul binding buffer (1 M sodium acetate, pH 5.0) and 400 ul culture supernatant were added and mixed with the chromatographic medium for 30 min. Non-bound material was removed by vacuum. The binding step was repeated. The chromatographic medium with bound lipase was washed 3 times with 200 ul washing buffer with decreasing buffer capacity (100/50/10 mM sodium acetate, pH 5.0). In each washing step the buffer was added, the plate was agitated 10 min, and the washing buffer was removed by vacuum. Finally, the bound lipase was eluted by adding two times 100 ul 100 mM Tris, 0.02% Brij 35 (Polyoxyethylen (23)laurylether), pH 9.0. For each elution step the plate was agitated 15 min before the eluted lipase was collected in a microtiter plate by vacuum.

Example 6

Determination of Concentration of Lipase Variants

Active Site Titration

The concentration of lipase variants which had been purified (conventionally purified as generally described in Example 2, and/or micro-purified as described in Example 6) were determined by burst active site titration as described in the following.

The purified lipase was diluted in 0.01% Triton-X100, if necessary, to get concentration below 5 uM (corresponding to 150 ug enzyme protein/ml). 100 ul purified lipase was mixed with approximately 100 ul of 40 uM of resorufin (ethyl resorufinyl heptylphosphonate; a lipase inhibitor) dissolved in 1 M Tris, 4 mM SDS (Sodium Dodecyl Sulphate), pH 9.0 in the well of a black microtiter plate. The precise concentration of resorufin is not important, it only has to be added in excess as compared to the 5 uM of lipase. Immediately after mixing, kinetics of fluorescence from liberated resorufin was measured every minute for 1-3 hours (until bursts were finalized) (excitation at 515 nm, emission at 590 nm, measured on a POLARstar fluorescence intensity measuring instrument from BMG LabTechnologies GmbH).

Measured fluorescence values are fitted to the equation:

$$F=F0+\text{Burst}*(1-\exp(-(t+dt)*\ln(2)/T½)+\text{Slope}*(t+dt)$$

where F is the measured fluorescence, F0 is the fluorescence background from inhibitor and lipase, t is the time since first fluorescence measurement, dt is the time from mixing of lipase with inhibitor to the first fluorescence measurement, Burst is the fluorescence burst, T½ is the half-time for the exponential burst, and Slope is the slope for the linear change in fluorescence, e.g. due to hydrolysis of lipase-ethyl heptylphosphonate complex and/or bleaching of resorufin.

The active lipase concentration was determined as the ratio between the calculated burst and the slope of a resorufin standard curve (0-4 uM; included on the microtiter plate).

Concentration Determination from $A_{280}$

The concentration of the purified lipase variants was also estimated from the absorbance at 280 nm using the extinction coefficient 1.24 $A_{280}$/mg.

Example 7

In vitro Test of Lipase Variants

The purified lipase variants were tested in an in vitro digestion model as described below.

Either of two diets (Diet I, and Diet II, respectively) was used in the in vitro model. The composition of Diet I is 34% (w/w) fat, 45% (w/w) carbohydrate, 2% (w/w) protein (the remainder water, salts, etc.). The composition of Diet II is: Fat 313, protein 146, and starch 358 (Nitrogen free Extract, NfE, may be calculated to 432), all in g/kg dry weight.

Diet I was prepared by mixing 247.2 g cow's milk (1.5% fat), 29.9 g olive oil, 87 g Calshake (commercially available from Fresenius Kabi and having an energy content of 2077 kJ/g, a protein content of 4.3 g milk protein/100 g, and a fat content of 24.4 g fat/100 g), and 9.9 g Methocel (Food Grade, E5 Premium LV FG (E464); Dow) using an UltraTurrex (YellowLine DI 25 basic) for 2 minutes. To reduce viscosity the diet was treated with 0.5 ug/ml of the SAVINASE 16.0 LEX protease (commercially available from Novozymes A/S, Krogshoejvej 36, DK-2880 Bagsvaerd, Denmark) at pH 8.0 for 4 hours at 50° C. The protease was then inactivated by reducing pH to 3 and incubating at 70° C. for 30 min, or 50° C. for 60 min.

Diet II consists of 73 g/kg (wet weight) poultry meal (Altromin), 73 g/kg pea meal, 73 g/kg casein (precipitated under acidic conditions, from Altromin), 290 g/kg wheat flour, 290 g/kg potato starch, 125 g/kg lard, 76 g/kg vitamins, minerals and trace elements, 375 g/kg cow's cream (33% fat).

100 ul of diet was mixed with 20 ul pepsin (Merck VL 317492437, catalogue no. 1.0792.0001, 700 mg/ml) and 30 ul lipase (duplicate of 4 concentrations) in the well of a microtiter plate. If the gastric step was to be run at pH 5, 10 ul buffer (0.8 M MES (2-[N-morpholino]ethanesulfonic acid), 0.8 M sodium acetate, 0.8 M imidazole, pH 7.0) was added, whereas no buffer was added if pH 3 was used for gastric step. The microtiter plate was incubated 1 hour at 37° C. with shaking (Eppendorf Thermomixer, 750 rpm) before adding 15 ul (if pH 5 used for gastric step), or 25 ul (if pH 3 used for gastric step) buffer (0.8 M MES (2-[N-morpholino]ethanesulfonic acid), 0.8 M sodium acetate, 0.8 M imidazole, pH 7.0) and 20 ul bile salts (50 g/l, corresponding to 100 mM, using an average molecular weight of 500 g/mol); Lipase activating bile salt mixture from Solvay Pharmaceuticals (batch 176.01-PA-7374)) resulting in a pH of 5.7 to 6.0. The plate was then incubated 2 hours at 37° C. with agitation before stopping the reaction by adding 50 ul 10% Triton-X100 in 1 M phosphoric acid. After diluting 125-250 times in 1% Triton-X100 the amount of free fatty acids was determined using a NEFA C kit from Wako Chemicals, as described in Example 3.

The dose response curves are fitted to the equation:

$$FFA=FFAmax*[E]/([E]+K)$$

where FFA is the amount of released free fatty acids, FFAmax is the maximal amount of free fatty acids that the lipases can liberate from the diet, [E] is the lipase concentration, and K is the lipase concentration that liberates half of FFAmax. Assuming that FFAmax is identical for the lipases an improvement factor (IF) is defined as:

$$IF=K(ref)/K(lipase)$$

where K(ref) is the concentration of a reference lipase that liberates half of FFAmax and K(lipase) is the lipase variant concentration that liberates half of FFAmax.

For the variants listed in Tables 7a and 8a below, as a reference lipase we have used the average of the lipase of SEQ ID NO: 1 and its deglycosylated variant N33Q (LV2934 in Table 1), i.e., K(ref)=½×(K(SEQ ID NO: 1)+K(LV2934)).

The lipase variants listed in Tables 7a and 8a below all have an improvement factor above 1.0. This means that a lower amount of these lipases is required in order to obtain a similar effect as compared to the reference lipase. The improvement factor of any lipase variant relative to, e.g., SEQ ID NO: 2 can be calculated as the improvement factor of the lipase variant in question relative to the reference lipase divided by the (constant) improvement factor of SEQ ID NO: 2 relative to the reference lipase, which is indicated in Table 7a below. When for example Active Site Titration (AST, Example 6) is used to determine the lipase concentration, and if the improvement factor for the variant in question is to be calculated relative to the lipase of SEQ ID NO: 2, one divides the average IF of the variant in question by the average IF of SEQ ID NO: 2 which is 0.88, preferably 0.9.

For the additional lipase variants listed in Tables 7b, 8b, 8c, and 8d below, the deglycosylated variant N33Q of SEQ ID NO: 1 (LV2934 in Table 1) was used as reference lipase. Each of these lipases have an improvement factor above 1.00 (average improvement factor minus the standard deviation). For the selection of the improved lipases, IF values and standard deviations were used with two decimals. These figures were subsequently rounded to one decimal.

TABLE 7a

Lipase variants with an improved performance in vitro (micro-purified)

| Enzyme tested | Improvement Factor (IF) AST | Improvement Factor (IF) $A_{280}$ |
|---|---|---|
| Diet I (pH 3 in gastric step) | | |
| SEQ ID NO: 2 | 0.9 +/− 0.1 | 0.9 +/− 0.2 |
| LVAR0003 | 1.9 +/− 0.4 | 2.4, 2.1 +/− 0.4 |
| LVAR0045 | 4.1 | — |
| LVAR0046 | 5.5 | — |
| LVAR0047 | 4.3 | — |
| LVAR0050 | 4.1 | — |
| LVAR0051 | 1.8 | — |
| LVAR0052 | 3.2 | — |
| LVAR0053 | 3.5 | — |
| LVAR0054 | 3.8 | — |
| LVAR0056 | 2.2 +/− 0.6 | — |
| LVAR0057 | 3.0 | — |
| LVAR0061 | 2.3 | — |
| LVAR0062 | 2.4 | — |
| LVAR0063 | 6.6 | — |
| LVAR0064 | 2.0 +/− 0.0 | — |
| LVAR0065 | 4.6 | — |
| LVAR0067 | 8.0 | — |
| LVAR0069 | 7.3 | — |
| LVAR0072 | 2.5 | — |
| Diet II (pH 3 in gastric step) | | |
| LVAR0074 | 3.3 | 2.2 |
| LVAR0076 | 5.0 | 3.2 |
| LVAR0077 | 4.5 | 2.5 |
| LVAR0078 | 2.9 | 1.5 |
| LVAR0079 | 6.7 | 7.7 |
| LVAR0080 | 7.1 | 5.9 |
| LVAR0086 | 4.3 | 2.7 |
| LVAR0088 | 1.8 | 3.1 |
| LVAR0091 | 5.2 | 4.3 |
| LVAR0094 | 11.0 | 10.5 |
| LVAR0095 | 9.3 | 11.5 |
| LVAR0096 | 8.3 | 6.6 |
| LVAR0099 | 11.1 | 11.8 |
| LVAR0101 | 8.1 | 8.2 |
| LVAR0102 | 6.0 | 4.1 |
| LVAR0103 | 7.5 | 4.3 |
| LVAR0104 | 7.9 | 5.9 |
| LVAR0106 | 10.0 | 9.7 |
| LVAR0108 | 6.1 | 6.5 |

— means "not determined"

TABLE 7b

Additional lipase variants with an improved performance in vitro

| Lipase | Substitutions as compared to SEQ ID NO: 2 | IF (AST) |
|---|---|---|
| Diet I pH 3 in gastric step | | |
| LVA129 | D27V + N33Q + V60S + D96W + T231R + N233R + Q249R | 5.7 +/− 2.0 |
| LVA130 | D27V + N33Q + V60S + T231R + N233R + Q249R | 1.5 +/− 0.4 |

TABLE 7b-continued

Additional lipase variants with an improved performance in vitro

| Lipase | Substitutions as compared to SEQ ID NO: 2 | IF (AST) |
|---|---|---|
| LVA139 | Q9H + N33Q + D102E + T231R + N233R | 2.4 +/− 1.2 |
| LVA140 | N33Q + D111E + T231R + N233R | 1.8 +/− 0.3 |
| LVA143 | N33Q + D122E + T231R + N233R | 1.8 +/− 0.5 |
| LVA147 | D27R + N33Q + G91N + N94R + D111A + S216P + L227G + T231R + N233R + P256T | 5.6 +/− 3.4 |
| LVA180 | N33Q + T231R + N233R + P256T | 2.3 +/− 0.7 |
| LVA182 | D27R + N33Q + G91A + L93* + N94* + F95* + D96* + D111A + T231R + N233R + P256T | 1.2 +/− 0.0 |
| LVA185 | N11R + N33Q + T231R + N233R | 1.9 +/− 0.7 |
| LVA198 | N33Q + N39H + T231R + N233R | 1.4 +/− 0.3 |
| LVA202 | N33Q + P229R + T231R + N233R | 1.5 +/− 0.5 |
| LVA206 | D27R + N33Q + G91N + N94R + D111A + G163K + S216P + L227G + T231R + N233R + P256T | 2.9 +/− 0.8 |
| LVA208 | N33Q + G91T + G163K + T231R + N233R | 4.6 +/− 2 |
| LVA210 | D27R + N33Q + G91A + D96E + L97Q + D111A + S216P + L227G + T231R + N233R + P256T | 1.3 +/− 0.3 |
| LVA211 | D27R + N33Q + G91A + D96E + L97Q + D111A + S216P + T231R + N233R + P256T | 4.3 +/− 1.2 |
| LVA238 | D27R + N33Q + G91A + D96E + D111A + T231R + N233R + D254G + P256T | 3.8 |
| LVA241 | D27R + N33Q + G91A + N94S + D111A + T231R + N233R + P256T | 1.8 |
| LVA243 | N33Q + N200S + T231R + N233R | 1.9 +/− 0.3 |
| LVA245 | N33Q + N39S + T231R + N233R | 3.6 +/− 0.0 |
| LVA247 | N33Q + E210R + T231R + N233R | 3.3 +/− 0.6 |
| LVA248 | N33Q + N39H + T231R + N233R + D254R | 2.4 +/− 0.9 |
| LVA249 | N33Q + T231R + N233R + D254R | 3.1 +/− 0.4 |
| LVA250 | N33Q + N94R + T231R + N233R | 4.0 +/− 0.1 |
| LVA252 | N33Q + D96R + T231R + N233R | 2.3 +/− 0.1 |
| LVA254 | D27N + N33Q + T231R + N233R | 1.5 +/− 0.1 |
| LVA256 | D27N + N33Q + E56R + T231R + N233R | 2.6 +/− 1.2 |
| LVA257 | N33Q + L227F + T231R + N233R | 2.3 +/− 0.7 |
| LVA272 | N33Q + N73Y + G225P + T231R + N233R | 2.3 +/− 0.2 |
| LVA273 | N33Q + G225P + T231R + N233R | 1.9 +/− 0.2 |
| LVA275 | N33Q + T231R + N233R + D254S | 6.2 +/− 1.5 |
| LVA277 | N33Q + D96G + T231R + N233R | 1.8 +/− 0.1 |
| LVA279 | N33Q + D96N + T231R + N233R + D254S | 6.1 +/− 0.6 |
| LVA280 | N33Q + T231R + N233R + D254G | 2.1 +/− 0.1 |
| LVA281 | N33Q + D130H + T231R + N233R | 1.2 +/− 0.0 |
| LVA284 | N33Q + E87A + T231R + N233R | 2.1 +/− 0.1 |
| LVA287 | N33Q + T231R + N233R + E239D | 1.2 |
| LVA307 | N33Q + D111A + T231R + N233R + D254G | 2.2 |
| LVA308 | N33Q + E210V + T231R + N233R + D254S | 5.9 |
| LVA310 | N11R + N33Q + E210V + T231R + N233R + D254S | 7.6 |
| LVA315 | N33Q + G91T + G163K + T231R + N233R + D254G | 3.4 |
| LVA317 | N33Q + G91T + G163K + T231R + N233R + D254S | 5.5 |
| LVA319 | N11R + N33Q + G91T + G163K + T231R + N233R + D254S | 6.6 |
| LVA325 | Q4R + D27R + N33Q + G91T + N94S + D111A + S216P + L227G + T231R + N233R + P256T | 1.2 |
| LVA327 | N33Q + G91T + N94S + D111A + V176I + T231R + N233R | 9.2 |
| LVA330 | Q4R + D27R + N33Q + G91T + N94S + D111A + E210D + S216P + L227G + T231R + N233R + P256T | 1.1 |
| LVA331 | Q4R + D27Q + N33Q + G91T + N94S + D111A + S216P + L227G + T231R + N233R + P256T | 1.2 |
| LVA333 | N33Q + G91T + N94S + D111A + T231R + N233R + P256T | 3.5 |
| LVA334 | N33Q + G177A + T231R + N233R | 1.0 |
| LVA338 | N33Q + T231R + N233R + G246A | 1.1 |
| LVA341 | D27N + N33Q + G91T + G163K + T231R + N233R + D254S | 4.2 |
| LVA345 | D27Q + N33Q + G91T + G163K + E219D + T231R + N233R | 2.3 |
| LVA347 | N33Q + G91T + E219D + T231R + N233R | 1.2 |

TABLE 7b-continued

Additional lipase variants with an improved performance in vitro

| Lipase | Substitutions as compared to SEQ ID NO: 2 | IF (AST) |
|---|---|---|
| | Diet II (pH 3 in gastric step) | |
| LVA055 | N33Q + E219D + T231R + N233R | 5.1 |
| LVA060 | N33Q + W117L + T231R + N233R | 2.4 |
| LVA061 | D27Q + N33Q + T231R + N233R | 2.6 |
| LVA063 | N33Q + G91T + T231R + N233R | 5.1 |
| LVA089 | D27S + N33Q + G91A + D96E + L97Q + D111A + S216P + T231R + N233R + P256T | 2.2 |
| LVA094 | D27R + N33Q + G91N + N94R + D111A + T231R + N233R + P256T | 1.0 |
| LVA099 | D27R + N33Q + G91T + N94S + D111A + S216P + L227G + T231R + N233R + P256T | 2.5 |
| LVA103 | Q4R + N33Q + T231R + N233R | 1.3 |
| LVA113 | N33Q + T231R + N233R + Q249R | 1.3 |
| LVA120 | N33Q + D96W + T231R + N233R | 1.1 |
| LVA179 | N33Q + G91N + T231R + N233R | 1.7 +/− 0.6 |

TABLE 8a

Lipase variants with an improved performance in vitro (purified)

| Enzyme tested | Improvement Factor (IF) AST | Improvement Factor (IF) $A_{280}$ |
|---|---|---|
| Diet I (pH 3 in gastric step) | | |
| LVAR0003 | 5.2 +/− 0.3 | 4.6 +/− 0.2 |
| LVAR0013 | 5.5 +/− 0.7 | 4.8 +/− 0.6 |
| LVAR0032 | 3.7 +/− 1.4 | 3.3 +/− 1.0 |
| LVAR0050 | 3.9 +/− 0.4 | 1.5 +/− 0.1 |
| LVAR0058 | 3.6 +/− 0.4 | 2.7 +/− 0.4 |
| LVAR0069 | 5.0 +/− 0.8 | 1.4 +/− 0.2 |

TABLE 8b

Additional lipase variants with an improved performance in vitro

| Lipase | Substitutions as compared to SEQ ID NO: 2 | IF (AST) |
|---|---|---|
| | Diet I (pH 5 in gastric step) | |
| LVA162 | N33Q + D167E + T231R + N233R | 1.4 +/− 0.2 |
| LVA214 | N33Q + E87A + T231R + N233R | 2.7 +/− 0.4 |
| LVA217 | N33Q + E210V + T231R + N233R | 2.8 +/− 0.9 |
| LVA218 | N33Q + E56K + T231R + N233R | 2.4 +/− 0.5 |
| LVA220 | N33Q + T231R + N233R + D254G | 2.0 +/− 0.2 |
| LVA221 | N33Q + D96S + T231R + N233R | 2.1 +/− 0.4 |
| LVA222 | N33Q + D122N + T231R + N233R | 1.6 +/− 0.2 |
| LVA228 | N26A + N33Q + T231R + N233R | 1.2 +/− 0.2 |
| LVA229 | N33Q + N162T + T231R + N233R | 3.5 +/− 1.9 |
| LVA230 | N33Q + A150V + N162G + T231R + N233R | 1.6 +/− 0.3 |
| LVA234 | N33Q + T231R + N233R + G240L | 2.8 +/− 0.2 |
| LVA308 | N33Q + E210V + T231R + N233R + D254S | 2.9 +/− 0.1 |
| LVA310 | N11R + N33Q + E210V + T231R + N233R + D254S | 3.0 +/− 0.4 |
| LVA327 | N33Q + G91T + N94S + D111A + V176I + T231R + N233R | 2.0 +/− 0.6 |
| LVA330 | Q4R + D27R + N33Q + G91T + N94S + D111A + E210D + S216P + L227G + T231R + N233R + P256T | 1.1 +/− 0.0 |
| LVA347 | N33Q + G91T + E219D + T231R + N233R | 1.7 +/− 0.3 |
| LVA353 | N33Q + G163R + T231R + N233R | 1.5 +/− 0.1 |
| LVA355 | N33Q + G163N + T231R + N233R | 2.2 +/− 0.4 |
| LVA357 | N33Q + G163C + T231R + N233R | 1.6 +/− 0.3 |
| LVA359 | N33Q + G163Q + T231R + N233R | 1.6 +/− 0.0 |
| LVA360 | N33Q + G163E + T231R + N233R | 1.7 +/− 0.1 |
| LVA362 | N33Q + G163H + T231R + N233R | 1.3 +/− 0.1 |

TABLE 8b-continued

Additional lipase variants with an improved performance in vitro

| Lipase | Substitutions as compared to SEQ ID NO: 2 | IF (AST) |
|---|---|---|
| LVA364 | N33Q + G163I + T231R + N233R | 1.5 +/− 0.4 |
| LVA371 | N33Q + G91K + T231R + N233R | 2.1 +/− 0.9 |
| LVA373 | N33Q + G91M + T231R + N233R | 2.0 +/− 0.4 |
| LVA375 | N33Q + G91F + T231R + N233R | 1.9 +/− 0.1 |
| LVA379 | N33Q + G91S + T231R + N233R | 1.4 +/− 0.1 |
| LVA381 | N33Q + G91W + T231R + N233R | 1.5 +/− 0.2 |
| LVA383 | N33Q + G91Y + T231R + N233R | 1.6 +/− 0.3 |
| LVA391 | N33Q + G163Y + T231R + N233R | 1.9 +/− 0.1 |
| LVA393 | N33Q + G163V + T231R + N233R | 1.6 +/− 0.5 |
| LVA399 | N33Q + G91C + T231R + N233R | 1.2 +/− 0.0 |
| LVA411 | N33Q + G91Y + Q126L + T231R + N233R | 2.2 +/− 0.0 |
| LVA412 | N33Q + G91M + G161E + T231R + N233R | 2.6 +/− 0.2 |
| LVA413 | N33Q + V128A + T231R + N233R | 1.6 +/− 0.1 |
| LVA414 | N33Q + V128A + T231R + N233R | 1.4 +/− 0.0 |
| LVA415 | N33Q + G163E + T231R + N233R | 1.9 +/− 0.5 |
| LVA416 | N33Q + G163V + L185M + T231R + N233R | 1.4 +/− 0.3 |
| LVA417 | N33Q + G38A + T231R + N233R | 1.6 +/− 0.1 |
| LVA420 | N33Q + G163A + T231R + N233R | 1.2 +/− 0.0 |
| LVA421 | N33Q + G91T + N94S + D111A + T231R + N233R | 1.2 +/− 0.1 |
| LVA438 | N33Q + G163M + T231R + N233R | 2.4 +/− 0.2 |
| LVA440 | N33Q + G91V + T231R + N233R | 1.5 +/− 0.2 |
| LVA442 | N33Q + D111A + T231R + N233R + Q249R | 2.6 +/− 0.4 |
| LVA450 | D27R + N33Q + G91A + D96E + L97Q + D111A + T231R + N233R + D254G + P256T | 2.7 +/− 0.1 |
| LVA451 | N33Q + G91T + N94R + T231R + N233R + D254S | 3.2 +/− 0.1 |
| LVA453 | N33Q + G91T + N94R + D111A + W117L + T231R + N233R | 2.0 +/− 0.5 |
| LVA454 | N33Q + W117L + T231R + N233R + D254S | 2.3 +/− 0.3 |
| LVA456 | N33Q + T231R + N233R + P256T | 1.7 +/− 0.1 |
| LVA458 | N33Q + T231R + N233R + D242E | 2.7 +/− 0.0 |
| LVA460 | N33Q + E87R + T231R + N233R | 3.8 +/− 0.1 |
| LVA461 | N33Q + E56R + T231R + N233R | 2.4 +/− 0.2 |
| LVA463 | N33Q + N162G + T231R + N233R | 2.3 +/− 0.2 |
| LVA464 | N33Q + G91L + T231R + N233R | 1.7 +/− 0.1 |
| LVA468 | N33Q + E87H + T231R + N233R | 2.1 +/− 0.2 |
| LVA470 | N33Q + D96N + T231R + N233R + Q249R | 2.9 +/− 1.2 |
| LVA471 | N33Q + G91T + N94R + T231R + N233R + D254S | 4.2 +/− 2.7 |
| LVA472 | N33Q + L227F + T231R + N233R + D254S | 2.0 +/− 0.1 |
| LVA474 | N33Q + G163A + T231R + N233R | 2.5 +/− 1.1 |
| LVA480 | D27R + N33Q + G91T + D96E + D111A + T231R + N233R + D254S + P256T | 1.7 +/− 0.6 |
| LVA482 | N33Q + G91T + N94R + T231R + N233R | 1.9 +/− 0.0 |
| LVA483 | N33Q + T231R + N233R + D254A | 1.5 +/− 0.1 |
| LVA484 | N33Q + T231R + N233R + D254N | 1.1 +/− 0.0 |
| LVA490 | N33Q + T231R + N233R + D254L | 2.4 +/− 0.1 |
| LVA492 | N33Q + T231R + N233R + D254K | 3.1 +/− 0.2 |
| LVA494 | N33Q + T231R + N233R + D254M | 1.8 +/− 0.2 |
| LVA505 | D27V + N33Q + V60S + G91T + D96W + T231R + N233R + Q249R | 4.5 +/− 0.6 |
| LVA506 | N33Q + D96N + L227G + T231R + N233R + Q249R | 2.6 +/− 0.1 |
| LVA507 | D27R + N33Q + L227G + T231R + N233R | 1.5 +/− 0.2 |
| LVA509 | D27R + N33Q + L227G + T231R + N233R + Q249R | 1.4 +/− 0.1 |
| LVA512 | N33Q + E219D + L227G + T231R + N233R + Q249R | 3.9 +/− 0.3 |
| LVA513 | D27Q + N33Q + L227G + T231R + N233R + Q249R | 1.3 +/− 0.0 |
| LVA516 | N33Q + W117L + L227G + T231R + N233R + Q249R | 1.5 +/− 0.1 |
| LVA518 | D5E + N33Q + W117L + L227G + T231R + N233R + Q249R | 1.2 +/− 0.2 |
| LVA519 | D27Q + N33Q + E219D + L227G + T231R + N233R + Q249R | 2.5 +/− 0.2 |
| LVA520 | N33Q + D96E + E219D + L227G + T231R + N233R + Q249R | 3.6 +/− 0.0 |
| LVA523 | D27R + N33Q + E56K + G91N + N94R + D111A + S216P + L227G + T231R + N233R + P256T | 2.0 +/− 0.2 |
| LVA526 | D27R + N33Q + E56Q + D57N + G91N + N94R + D111 A + S216P + L227G + T231R + N233R + P256T | 2.2 +/− 0.4 |
| LVA527 | D27R + N33Q + E56Q + D57N + G91N + N94R + D111 + S216P + L227G + T231R + N233R + D254S + P256T | 1.9 +/− 0.7 |
| LVA530 | D27R + N33Q + E56S + G91N + N94R + D111A + S216P + L227G + T231R + N233R + P256T | 1.5 +/− 0.4 |
| LVA532 | D27R + N33Q + G91N + N94R + D111A + S216P + L227G + T231R + N233R + D254S + P256T | 1.8 +/− 0.1 |
| LVA535 | D27R + N33Q + G91N + N94R + D111A + S216P + L227G + T231R + N233R + D254S + P256T | 1.8 +/− 0.0 |
| LVA540 | D27R + N33Q + G91N + N94R + D111S + A155V + S216P + L227G + T231R + N233R + D254S + P256T | 1.6 +/− 0.3 |
| LVA542 | D27R + N33Q + G91N + N94R + D111S + S216P + L227G + T231R + N233R + D254S + P256T | 1.7 +/− 0.2 |
| LVA547 | N33Q + D111A + T231R + N233R + D254S | 2.1 +/− 0.1 |
| LVA548 | N33Q + D111A + W117L + T231R + N233R + D254S | 1.7 +/− 0.4 |
| LVA555 | N33Q + T231R + N233R + P256N | 2.1 +/− 0.1 |
| LVA561 | N33Q + T231R + N233R + P256G | 1.6 +/− 0.0 |
| LVA562 | N33Q + T231R + N233R + P256H | 1.2 +/− 0.1 |
| LVA565 | N33Q + T231R + N233R + P256M | 3.0 +/− 0.3 |
| LVA567 | N33Q + T231R + N233R + P256W | 2.2 +/− 0.4 |
| LVA569 | N33Q + T231R + N233R + P256Y | 1.7 +/− 0.4 |
| LVA576 | N33Q + T231R + N233R + P256F | 2.0 +/− 1.0 |
| LVA578 | N33Q + T231R + N233R + P256V | 1.9 +/− 0.5 |
| LVA580 | N33Q + G91M + G163W + T231R + N233R | 1.4 +/− 0.3 |
| LVA581 | N33Q + G91M + G163T + T231R + N233R | 1.7 +/− 0.6 |
| LVA582 | N33Q + G91M + G163D + T231R + N233R | 1.7 +/− 0.7 |
| LVA583 | N33Q + G91K + G163W + T231R + N233R | 1.3 +/− 0.2 |
| LVA586 | N33Q + G91T + G163W + T231R + N233R | 1.3 +/− 0.3 |
| LVA602 | N33Q + V176N + T231R + N233R | 1.7 +/− 0.7 |
| LVA604 | N33Q + V176D + T231R + N233R | 1.2 +/− 0.2 |
| LVA614 | N33Q + W117F + T231R + N233R | 1.6 +/− 0.1 |
| LVA622 | N33Q + V176I + T231R + N233R | 1.3 +/− 0.0 |
| LVA623 | N33Q + D111N + T231R + N233R | 1.1 +/− 0.0 |
| LVA627 | N33Q + D111N + G225P + T231R + N233R | 1.9 +/− 0.3 |
| LVA629 | N33Q + D111N + S216P + T231R + N233R | 1.4 +/− 0.1 |
| LVA631 | D27R + N33Q + G91T + N94R + D111A + S216P + L227G + T231R + N233R | 2.4 +/− 0.4 |
| LVA632 | N33Q + G91M + G163P + T231R + N233R | 1.5 +/− 0.1 |
| LVA634 | N33Q + G91T + G163A + T231R + N233R | 1.3 +/− 0.1 |
| LVA639 | N33Q + W117D + T231R + N233R | 1.4 +/− 0.2 |
| LVA640 | N33Q + W117H + T231R + N233R | 1.3 +/− 0.1 |
| LVA649 | N33Q + W117C + T231R + N233R | 1.6 +/− 0.1 |
| LVA650 | N33Q + W117C + T231R + N233R | 1.7 +/− 0.1 |
| LVA651 | N33Q + W117K + T231R + N233R | 1.7 +/− 0.1 |
| LVA653 | N33Q + W117V + T231R + N233R | 1.2 +/− 0.1 |
| LVA656 | N11S + N33Q + T231R + N233R | 2.0 +/− 0.4 |
| LVA658 | N33Q + W117E + V176K + T231R + N233R | 2.2 +/− 0.8 |
| LVA659 | N33Q + W117G + T231R + N233R | 1.8 +/− 0.3 |
| LVA664 | N33Q + W117P + T231R + N233R | 2.3 +/− 0.7 |
| LVA665 | N33Q + W117S + T231R + N233R | 1.7 +/− 0.1 |
| LVA666 | N33Q + W117T + T231R + N233R | 1.8 +/− 0.1 |
| LVA667 | N33Q + W117I + T231R + N233R | 1.3 +/− 0.1 |
| LVA670 | D27R + N33Q + L227G + T231R + N233R + Q249R + D254S | 4.1 +/− 0.8 |
| LVA696 | N33Q + V176M + T231R + N233R | 1.3 +/− 0.2 |
| LVA697 | N33Q + V176H + T231R + N233R | 1.2 +/− 0.2 |
| LVA700 | N33Q + V176A + T231R + N233R | 1.2 +/− 0.0 |
| LVA702 | D27V + N33Q + L227F + T231R + N233R + Q249R | 1.3 +/− 0.3 |
| LVA705 | N33Q + W117Y + T231R + N233R | 1.1 +/− 0.1 |
| LVA707 | N33Q + W117Y + V176D + T231R + N233R | 1.4 +/− 0.3 |
| LVA715 | D27R + N33Q + P136H + L227G + T231R + N233R + Q249R + D254S | 1.3 +/− 0.2 |
| LVA718 | N11R + N33Q + T231R + N233R + T244S | 2.0 +/− 0.5 |
| LVA721 | N33Q + G91T + D96N + D111A + V176I + T231R + N233R + D254S | 3.0 +/− 0.3 |
| LVA722 | N33Q + G91T + N94S + D111A + V176I + T231R + N233R + D254S | 2.3 +/− 0.2 |
| LVA723 | N33Q + G161A + T231R + N233R | 1.5 +/− 0.2 |
| LVA731 | N33Q + G38I + G177A + T231R + N233R | 2.9 +/− 0.6 |

TABLE 8b-continued

| Additional lipase variants with an improved performance in vitro | | |
|---|---|---|
| Lipase | Substitutions as compared to SEQ ID NO: 2 | IF (AST) |
| LVA732 | N33Q + N101Q + T231R + N233R | 2.5 +/− 0.6 |
| LVA733 | N33Q + N94Q + T231R + N233R | 2.0 +/− 0.1 |
| LVA736 | N11Q + N33Q + T231R + N233R | 2.0 +/− 0.2 |
| LVA738 | N8Q + N33Q + T231R + N233R | 1.6 +/− 0.2 |
| LVA740 | N33Q + T231R + N233R + N251Q | 1.3 +/− 0.1 |
| LVA743 | N33Q + N200Q + T231R + N233R | 1.4 +/− 0.0 |
| LVA744 | N33Q + G177A + T231R + N233R | 2.3 +/− 0.3 |
| LVA746 | N33Q + N73Q + T231R + N233R | 1.8 +/− 0.2 |
| LVA749 | N33Q + I86L + T231R + N233R | 1.6 +/− 0.4 |
| LVA753 | N33Q + K98I + G163K + T231R + N233R | 1.5 +/− 0.3 |
| LVA754 | D27R + N33Q + G91T + D96E + D111A + G163K + T231R + N233R + D254S + P256T | 2.0 +/− 0.4 |
| LVA755 | D27R + N33Q + G91T + D96E + D111A + G163A + T231R + N233R + D254S + P256T | 3.9 +/− 0.3 |
| LVA770 | D27R + N33Q + S216P + L227G + T231R + N233R + Q249R | 1.6 +/− 0.2 |
| LVA771 | N33Q + K98I + G163K + N200Q + T231R + N233R + N251S | 1.7 +/− 0.5 |
| LVA772 | N33Q + G38S + G163K + T231R + N233R | 1.7 +/− 0.6 |
| LVA774 | N33Q G38Y T231R N233R | 1.3 +/− 0.2 |
| LVA777 | D27R + N33Q + G91T + N94R + D111A + S216P + L227G + T231R + N233R + P256T | 1.4 +/− 0.2 |
| LVA778 | D27R + N33Q + G91T + N94R + D111A + S216P + L227G + T231R + N233R + P256T | 1.3 +/− 0.0 |
| LVA782 | N33Q + G38N + N73Q + T231R + N233R | 1.9 +/− 0.9 |
| LVA783 | N33Q + G38D + R84E + T231R + N233R | 1.8 +/− 0.6 |
| LVA784 | N33Q + G38Q + T231R + N233R | 1.8 +/− 0.5 |
| LVA786 | N33Q + G38I + T231R + N233R | 2.2 +/− 0.3 |
| LVA788 | N33Q + G38K + T231R + N233R | 1.4 +/− 0.1 |
| LVA792 | N33Q + G38F + T231R + N233R | 2.4 +/− 0.2 |
| LVA799 | N33Q + G38H + N200Q + T231R + N233R + N251S | 2.2 +/− 0.2 |
| LVA800 | N33Q + G38L + T231R + N233R | 1.8 +/− 0.3 |
| LVA804 | N33Q + G38P + T231R + N233R | 1.5 +/− 0.3 |
| LVA805 | N33Q + G38T + T231R + N233R | 1.9 +/− 0.1 |
| LVA806 | N11R + N33Q + G91T + W117I + G163K + T231R + N233R + D254S | 2.6 +/− 0.4 |
| LVA808 | D27R + N33Q + G38A + G91T + D96E + D111A + G163K + T231R + N233R + D254S + P256T | 3.7 +/− 0.2 |
| LVA809 | N11R + N33Q + G91T + W117I + G163K + T231R + N233R + D254S | 2.6 +/− 0.2 |
| LVA811 | D27R + N33Q + G38A + G91T + D96E + D111A + G163A + T231R + N233R + D254S + P256T | 2.2 +/− 0.3 |
| LVA813 | D27R + N33Q + V176Q + L227G + T231R + N233R + Q249R + D254S | 2.6 +/− 0.4 |
| LVA814 | N33Q + W117I + V176Q + T231R + N233R + P256A | 1.8 +/− 0.5 |
| LVA816 | N33Q + G38A + G163A + T231R + N233R + P256A | 3.1 +/− 0.1 |
| LVA817 | N33Q + W117I + V176Q + T231R + N233R | 2.8 +/− 0.8 |
| LVA818 | N33Q + G177A + T231R + N233R + G246A | 2.3 +/− 0.8 |
| LVA819 | E1N N33Q T231R N233R | 2.3 +/− 1.2 |
| LVA821 | N33Q G38H T231R N233R | 2.0 +/− 0.4 |
| LVA830 | N11R + N33Q + G91T + G163K + V176Q + T231R + N233R + D254S | 1.8 +/− 0.3 |
| LVA831 | N33Q + K98I + T231R + N233R | 1.2 +/− 0.1 |
| LVA834 | D27R + N33Q + W117I + V176Q + L227G + T231R + N233R + Q249R + D254S | 1.4 +/− 0.0 |
| LVA835 | N11R + N33Q + G38A + G91T + G163K + T231R + N233R + D254S | 1.9 +/− 0.4 |
| LVA839 | N33Q + G163W + T231R + N233R | 1.9 +/− 0.3 |
| LVA841 | N33Q + G38A + G163A + T231R + N233R | 1.9 +/− 0.2 |
| LVA842 | D27R + N33Q + G91T + D96E + L97Q + D111A + T231R + N233R + D254S + P256T | 2.5 +/− 0.9 |
| LVA844 | N33Q + T231R + N233R + D254Q | 1.5 +/− 0.2 |
| LVA846 | N11R + N33Q + G91T + S115L + G163K + T231R + N233R + D254S | 1.5 +/− 0.2 |
| LVA847 | N11R + N33Q + G91T + G163K + V176W + T231R + N233R + D254S | 1.4 +/− 0.3 |
| LVA848 | N33Q + G163D + T231R + N233R | 1.3 +/− 0.1 |
| LVA849 | N33Q + G163D + T231R + N233R | 1.2 +/− 0.2 |
| LVA850 | N33Q + G163P + T231R + N233R | 1.2 +/− 0.2 |
| LVA853 | E1D + N33Q + G91T + N94R + D111A + W117L + T231R + N233R + D254S | 1.2 +/− 0.0 |
| LVA857 | N33Q + G91T + N94R + D111A + W117L + V176W + T231R + N233R | 3.8 +/− 0.7 |
| LVA860 | Q4P + D27R + N33Q + G91N + N94R + D111A + L206F + S216P + L227G + T231R + N233R + P256T | 2.6 +/− 0.4 |
| LVA862 | D27R + N33Q + T37K + N71I + G91N + N94R + K98I + D111A + S216P + L227G + T231R + N233R + P256T | 1.7 +/− 0.5 |
| LVA863 | D27R + N33Q + E43K + K46M + I90V + G91N + N94R + D111A + T114I + S216P + L227G + T231R + N233R + P256T | 2.1 +/− 0.1 |
| LVA865 | N33Q + W117S + T231R + N233R | 2.0 +/− 0.2 |
| LVA866 | N33Q + G61R + V63R + G156R + V176W + T231R + N233R + P256I | 2.1 +/− 0.4 |
| LVA869 | N33Q + D96N + G156R + V176W + T231R + N233R | 2.6 +/− 0.3 |
| LVA871 | N33Q + G156R + V176W + T231R + N233R + Q249R | 1.6 +/− 0.3 |
| LVA873 | N33Q + G91T + N94S + D111A + G163T + V176W + T231R + N233R | 1.4 +/− 0.3 |
| LVA875 | N33Q + G91T + N94S + D111A + S115L + G163T + V176I + T231R + N233R | 1.6 +/− 0.1 |
| LVA877 | N11R + D27R + N33Q + E56Q + D57N + G91N + N94R + D111S + G163T + S216P + L227G + T231R + N233R + D254S + P256T | 1.6 +/− 0.2 |
| LVA878 | D27R + N33Q + E56Q + D57N + G91N + N94R + D111S + G163T + S216P + L227G + T231R + N233R + D254S + P256T | 1.2 +/− 0.1 |
| LVA880 | N11R + D27R + N33Q + E56Q + D57N + G91N + N94R + D111S + S216P + L227G + T231R + N233R + D254S + P256T | 2.7 +/− 0.3 |
| LVA882 | D27R + N33Q + E56Q + D57N + G91N + N94R + D111S + S216P + L227G + T231R + N233R + D242E + D254S + P256T | 2.6 +/− 0.1 |
| LVA883 | D27R + N33Q + G38A + E56Q + D57N + G91N + N94R + D111S + S216P + L227G + T231R + N233R + D254S + P256T | 3.4 +/− 1.1 |
| LVA888 | Q4R + D27Q + N33Q + G91T + N94S + E99D + D111A + E210D + S216P + L227G + T231R + N233R + P256L | 1.2 +/− 0.2 |
| LVA890 | N33Q + G38A + G91T + G163A + T231R + N233R + D254S | 1.6 +/− 0.5 |
| LVA892 | N33Q + G38A + G163A + T231R + N233R + D254I | 1.2 +/− 0.2 |
| LVA896 | N11R + N33Q + I90L + G163L + T231R + N233R | 4.0 +/− 0.4 |
| LVA897 | N11R + N33Q + I90L + G163L + T231R + N233R + D254S | 1.9 +/− 0.5 |
| LVA899 | N11R + N33Q + E56Q + G91T + G163K + V176Q + T231R + N233R + D254S | 1.3 +/− 0.2 |
| LVA904 | N11R + D27R + N33Q + G91T + D96E + D111A + G163K + T231R + N233R + D254S + P256T | 4.5 +/− 1.6 |
| LVA906 | N11R + N33Q + G38A + G91T + G112A + G163A + T231R + N233R + D254S | 3.6 +/− 0.4 |
| LVA907 | N11R + N33Q + G91T + G163K + E210D + T231R + N233R + D254S | 2.2 +/− 0.3 |
| LVA913 | N11R + N33Q + G91T + G163K + T231R + N233R + D254I | 3.5 +/− 0.9 |
| LVA915 | N11R + N33Q + G91T + G163K + V176T + T231R + N233R + D254S | 1.8 +/− 0.5 |
| LVA917 | N11R + N33Q + G91T + G163P + T231R + N233R + D254S | 2.0 +/− 0.1 |
| LVA919 | N11R + N33Q + G91M + G163T + T231R + N233R + D254S | 1.4 +/− 0.2 |
| LVA921 | N11R + N33Q + G38A + G91T + G163K + V176D + T231R + N233R + D254S | 3.9 +/− 1.8 |
| LVA925 | N33Q + E56Q + G156R + V176W + T231R + N233R | 1.4 +/− 0.2 |
| LVA927 | E1D + N33Q + G38A + G91T + N94R + D111A + W117L + V176W + T231R + N233R | 1.8 +/− 0.2 |
| LVA928 | N33Q + G163K + G177A + T231R + N233R + G246A | 3.4 +/− 0.7 |
| LVA929 | N11R + N33Q + E56Q + G91T + G163K + T231R + N233R + D254S | 2.1 +/− 0.2 |

TABLE 8b-continued

Additional lipase variants with an improved performance in vitro

| Lipase | Substitutions as compared to SEQ ID NO: 2 | IF (AST) |
|---|---|---|
| LVA930 | N11R + N33Q + I90L + G163K + T231R + N233R + D254S | 2.0 +/− 0.2 |
| LVA933 | D27R + N33Q + E56Q + D57N + G91N + N94R + D111S + S216P + L227G + T231R + N233R + Q249R + D254S + P256T | 2.7 +/− 0.7 |
| LVA934 | D27R + N33Q + E56Q + D57N + G91N + N94R + D111S + S216P + E219D + L227G + T231R + N233R + D254S + P256T | 2.0 +/− 0.2 |
| LVA941 | N11R + N33Q + I90L + G91T + N94S + D96E + G163K + T231R + N233R + D254S | 1.5 +/− 0.2 |
| LVA942 | N11R + N33Q + G91T + G163K + V176I + T231R + N233R + D254S | 1.9 +/− 0.1 |
| LVA943 | N11R + N33Q + G91T + G163K + V176Q + T231R + N233R + D254S | 2.1 +/− 0.0 |
| LVA944 | N11R + N33Q + G91T + G163A + V176T + T231R + N233R + D254S | 1.7 +/− 0.1 |
| LVA945 | N11R + N33Q + G91T + G163L + V176I + T231R + N233R + D254S | 2.0 +/− 0.0 |
| LVA946 | N11R + N33Q + G91T + G163L + V176T + T231R + N233R + D254S | 2.2 +/− 0.6 |
| LVA947 | N11R + N33Q + G91T + G163L + T231R + N233R + D254S | 1.8 +/− 0.2 |
| LVA948 | N11R + N33Q + G91T + G163P + T231R + N233R + D254S | 1.5 +/− 0.1 |
| LVA949 | N11R + N33Q + G91T + G163P + V176I + T231R + N233R + D254S | 2.4 +/− 0.4 |
| LVA950 | N11R + N33Q + G91T + G163L + T231R + N233R + D254S + P256N | 2.6 +/− 0.6 |
| LVA952 | D27R + N33Q + E56Q + D57N + G91N + N94R + D111S + G163T + S216P + L227G + T231R + N233R + Q249R + D254S + P256T | 1.9 +/− 0.0 |
| LVA953 | Q4R + D27Q + N33Q + G91T + N94S + E99D + D111A + G163A + E210V + S216P + L227G + T231R + N233R + P256L | 2.7 +/− 0.4 |
| LVA954 | Q4R + D27Q + N33Q + G91T + N94S + E99D + D111A + V176I + E210V + S216P + L227G + T231R + N233R + P256L | 3.4 +/− 0.4 |
| LVA959 | N33Q + E210Y + T231R + N233R + D254Y + I255F | 1.4 +/− 0.2 |
| LVA961 | N33Q + L93F + D102Y + T231R + N233R | 1.5 +/− 0.1 |
| LVA962 | D27R + N33Q + L227G + T231R + N233R + Q249R + D254S | 1.6 +/− 0.1 |
| LVA964 | N11S + N33Q + T231R + N233R | 4.0 +/− 2.7 |
| LVA966 | N11R + N33Q + T231R + N233R | 2.6 +/− 1.0 |
| LVA968 | N33Q + G38A + G91T + G163K + T231R + N233R + D254S | 2.7 +/− 0.7 |
| LVA969 | N33Q + W117Y + V176T + T231R + N233R | 2.1 +/− 0.3 |
| LVA970 | N8L + N11R + N33Q + G91T + G163K + T231R + N233R + D254S | 3.7 +/− 1.8 |
| LVA972 | E1N + N33Q + G38A + G91T + G163P + V176F + T231R + N233R | 1.8 +/− 0.4 |
| LVA973 | N11R + N33Q + G38A + G91T + G163P + V176G + T231R + N233R + D254S | 2.1 +/− 0.4 |
| LVA976 | N11R + N33Q + G91T + G163K + T231R + N233R + D254A + P256F | 3.3 +/− 0.7 |
| LVA977 | N11R + N33Q + G91T + G163K + T231R + N233R + P256F | 1.6 +/− 0.3 |
| LVA978 | N11R + N33Q + G91T + G163K + T231R + N233R + D254S + P256F | 3.0 +/− 0.6 |
| LVA979 | N11R + N33Q + G38A + G91T + G156R + G163K + V176T + T231R + N233R + D254S | 1.6 +/− 0.2 |
| LVA980 | N33Q + G91K + D96S + G163T + T231R + N233R + Q249R | 2.7 +/− 1.4 |
| LVA981 | N11R + N33Q + G91T + G163N + T231R + N233R + D254S | 1.9 +/− 0.3 |
| LVA983 | N11R + N33Q + G91T + G163T + T231R + N233R + D254S | 3.4 +/− 0.6 |
| LVA984 | N11R + N33Q + G91T + G163W + T231R + N233R + D254S | 5.9 +/− 1.7 |
| LVA985 | N11R + N33Q + G91K + G163K + T231R + N233R + D254S | 2.2 +/− 0.2 |
| LVA987 | N11R + G23E + N33Q + G91T + G163K + T231R + N233R + D254S | 1.4 +/− 0.0 |
| LVA988 | N11R + N33Q + G91T + V141E + G163K + T231R + N233R + D254S | 2.0 +/− 0.4 |
| LVA989 | N11R + N33Q + L52R + G91T + G163K + T231R + N233R + D254S | 4.2 +/− 1.2 |
| LVA990 | N11R + N33Q + G91T + V141L + G163K + T231R + N233R + D254S | 1.8 +/− 0.7 |
| LVA991 | N11R + N33Q + T37K + G91T + G163K + T231R + N233R + D254S | 3.1 +/− 0.7 |
| LVA993 | N11R + N33Q + A68V + G91T + G163K + T231R + N233R + D254S | 3.0 +/− 0.5 |
| LVA994 | N11R + N33Q + G91T + G163A + V176I + T231R + N233R + D254S | 3.4 +/− 1.9 |
| LVA995 | N11R + N33Q + T37M + G91T + G163P + V176T + T231R + N233R + D254S | 2.8 +/− 0.2 |
| LVA997 | N11R + N33Q + G91T + G163L + T231R + N233R + D254S | 2.7 +/− 0.8 |
| LVA998 | N11R + N33Q + G91T + G163K + T231R + N233R + D254S + P256I | 2.2 +/− 0.7 |
| LVA999 | N33Q + G38S + G156R + G163K + V176W + T231R + N233R | 6.4 +/− 0.2 |
| LVA1000 | N11R + D27R + N33Q + E56Q + D57N + G91N + N94R + D111S + G163K + S216P + L227G + T231R + N233R + D254S + P256T | 2.8 +/− 0.8 |
| LVA1002 | N11R + N33Q + G38A + G91T + G163P + V176G + T231R + N233R + D254S | 1.4 +/− 0.2 |
| LVA1003 | N11R + N33Q + G38A + G91T + G163Q + V176G + T231R + N233R + D254S | 2.6 +/− 0.7 |
| LVA1004 | N11R + N33Q + G38A + G91T + G163T + V176G + T231R + N233R + D254S | 3.2 +/− 0.8 |
| LVA1005 | N11R + N33Q + G38A + G91T + N94R + G163P + V176G + T231R + N233R + D254S | 2.3 +/− 0.4 |
| LVA1006 | E1* + N11R + N33Q + G38A + G91N + N94R + G163P + V176G + T231R + N233R + D254S | 1.4 +/− 0.1 |
| LVA1007 | E1N + N11R + N33Q + G38A + G91T + G163P + V176F + T231R + N233R | 2.3 +/− 0.3 |
| LVA1008 | E1N + F10L + N11R + N33Q + G38A + G91T + G163P + V176F + T231R + N233R | 2.5 +/− 0.1 |
| LVA1009 | E1N + N33Q + G38A + G91T + G163P + V176F + T231R + N233R + D254S | 2.7 +/− 0.2 |
| LVA1010 | E1N + N33Q + G38A + G91T + D111A + G163P + V176F + T231R + N233R | 1.9 +/− 0.3 |
| LVA1011 | E1N + N33Q + G38A + G91T + G163P + V176F + L227F + T231R + N233R | 2.1 +/− 0.3 |
| LVA1012 | E1N + N11R + N33Q + G38A + G91T + D111A + G163P + V176F + T231R + N233R | 2.4 +/− 0.3 |
| LVA1013 | E1N + N33Q + G38A + G91T + G163P + V176F + L227F + T231R + N233R + D254S | 3.4 +/− 1.2 |
| LVA1014 | E1N + N33Q + G38A + G91T + G163P + V176F + T231R + N233R + D254S + I255A + P256Q | 2.2 +/− 0.2 |
| LVA1015 | E1N + N11R + N33Q + G38A + G91T + D111A + G163P + V176F + T231R + N233R + D254S | 1.9 +/− 0.1 |
| LVA1017 | N33Q + G156R + V176W + T231R + N233R + P256I | 2.4 +/− 0.3 |
| LVA1018 | N33Q + G91T + N94S + D111A + G156R + G163T + V176W + T231R + N233R | 1.9 +/− 0.6 |
| LVA1019 | N33Q + G91T + N94S + D111A + G156R + G163T + V176I + T231R + N233R | 1.3 +/− 0.3 |
| LVA1021 | N11R + N33Q + G38A + G91T + D102G + S115L + G163K + T231R + N233R + D254S + P256T | 2.5 +/− 0.3 |
| LVA1023 | N11R + N33Q + G38A + G91T + S115L + G163K + T231R + N233R + D254S + P256T | 2.3 +/− 0.1 |
| LVA1027 | E1N + N11R + N33Q + G91T + G163A + T231R + N233R + G246A + D254S | 3.1 +/− 0.1 |
| LVA1028 | N11R + D27R + N33Q + D57G + G91T + D96E + D111A + G163K + T231R + N233R + D254S + P256T | 3.7 +/− 1.4 |
| LVA1029 | N33Q + D96N + G156R + V176W + T231R + N233R + Q249R | 3.4 +/− 0.0 |
| LVA1031 | N33Q + I86F + L93F + D102Y + E210Y + L227F + T231R + N233R + D254Y + I255F + L269F | 1.4 +/− 0.1 |
| LVA1032 | N33Q + I86F + L93F + D102Y + E210Y + L227F + T231R + N233R + D254Y + I255F | 1.5 +/− 0.2 |

TABLE 8b-continued

Additional lipase variants with an improved performance in vitro

| Lipase | Substitutions as compared to SEQ ID NO: 2 | IF (AST) |
|---|---|---|
| LVA1033 | N11C + N33Q + G91T + G163K + T231R + N233R + D254S | 2.5 +/− 0.1 |
| LVA1034 | N11L + N33Q + G91T + G163K + T231R + N233R + D254S | 4.3 +/− 0.0 |
| LVA1035 | N11H + N33Q + G91T + G163K + T231R + N233R + D254S | 2.2 +/− 0.0 |
| LVA1036 | N11D + N33Q + G91T + G163K + T231R + N233R + D254S | 4.1 +/− 1.2 |
| LVA1037 | N11R + N33Q + G91T + D96W + G163K + T231R + N233R + D254S | 3.4 +/− 0.0 |
| LVA1038 | D27R + N33Q + G91T + D96E + L97Q + D111A + G163K + T231R + N233R + D254S + P2561 | 5.6 +/− 1.8 |
| LVA1040 | N11P + N33Q + G91T + G163K + T231R + N233R + D254S | 3.0 +/− 1.0 |
| LVA1041 | Q4R + D27N + N33Q + G38A + G91T + N94S + E99D + D111A + V176I + E210V + S216P + L227G + T231R + N233R + P256L | 2.5 +/− 0.9 |
| LVA1044 | N11R + N33Q + E56Q + G163K + T231R + N233R + D254S | 2.9 +/− 0.5 |
| LVA1045 | N11R + N33Q + G91T + G163A + T231R + N233R + D254S | 2.0 +/− 0.1 |
| LVA1046 | N11R + N33Q + G91T + G163P + T231R + N233R + D254S | 2.8 +/− 0.1 |
| LVA1048 | N11R + N33Q + G91T + G163K + L227G + P229R + T231R + N233R + D254S | 2.5 +/− 0.3 |

TABLE 8c

Additional lipase variants with an improved performance in vitro

| Lipase | Substitutions as compared to SEQ ID NO: 2 | IF (A280) |
|---|---|---|
| | Diet I (pH 3 in gastric step) | |
| LVA012 | D27R + N33Q + G91A + D96E + L97Q + D111A + T231R + N233R + P256T | 2.5 +/− 0.4 |
| LVA023 | N33Q + E210D + T231R + N233R | 1.9 +/− 0.2 |
| LVA027 | N33Q + T231R + N233R | 1.8 +/− 0.2 |
| LVA041 | N33Q + D111A + T231R + N233R | 2.0 +/− 0.3 |
| LVA043 | N33Q + G91T + T231R + N233R | 3.1 |
| LVA061 | D27Q + N33Q + T231R + N233R | 1.7 +/− 0.4 |
| LVA139 | Q9H + N33Q + D102E + T231R + N233R | 2.3 +/− 1.0 |
| LVA216 | N33Q + E56Q + T231R + N233R | 1.3 +/− 0.1 |
| LVA231 | N33Q + I90L + G163L + T231R + N233R | 1.3 +/− 0.2 |
| LVA238 | D27R + N33Q + G91A + D96E + D111A + T231R + N233R + D254G + P256T | 1.3 +/− 0.3 |
| LVA245 | N33Q + N39S + T231R + N233R | 1.7 +/− 0.7 |
| LVA250 | N33Q + N94R + T231R + N233R | 3.3 +/− 1.8 |
| LVA275 | N33Q + T231R + N233R + D254S | 4.3 +/− 2.7 |
| LVA315 | N33Q + G91T + G163K + T231R + N233R + D254G | 1.4 +/− 0.2 |
| LVA317 | N33Q + G91T + G163K + T231R + N233R + D254S | 1.8 +/− 0.4 |
| LVA319 | N11R + N33Q + G91T + G163K + T231R + N233R + D254S | 2.2 +/− 0.3 |
| LVA341 | D27N + N33Q + G91T + G163K + T231R + N233R + D254S | 2.3 +/− 0.1 |
| LVA348 | N33Q + T231R + N233R | 1.4 +/− 0.2 |
| LVA349 | K98I + T231R + N233R + N251S | 1.4 +/− 0.2 |
| LVA368 | N33Q + G163P + T231R + N233R | 1.7 +/− 0.1 |
| LVA370 | N33Q + G163D + T231R + N233R | 1.3 +/− 0.1 |
| LVA387 | N33Q + G163T + T231R + N233R | 1.1 +/− 0.1 |
| LVA389 | N33Q + G163W + T231R + N233R | 1.3 +/− 0.0 |
| LVA437 | N33Q + G38A + G163A + T231R + N233R | 1.4 +/− 0.0 |
| LVA444 | N33Q + D111A + T231R + N233R + D254S | 1.2 +/− 0.0 |
| LVA473 | D27R + N33Q + G91T + D96E + L97Q + D111A + T231R + N233R + D254S + P256T | 1.2 +/− 0.2 |
| LVA553 | N33Q + T231R + N233R + P256A | 1.2 +/− 0.0 |
| LVA566 | N33Q + T231R + N233R + P256S | 1.2 +/− 0.1 |
| LVA620 | N33Q + G91T + N94S + D111A + V176I + T231R + N233R + D254S | 1.2 +/− 0.1 |

TABLE 8c-continued

Additional lipase variants with an improved performance in vitro

| Lipase | Substitutions as compared to SEQ ID NO: 2 | IF (A280) |
|---|---|---|
| LVA672 | N33Q + S115L + T231R + N233R | 1.1 +/− 0.0 |
| LVA675 | N33Q + G38A + G91T + G163K + T231R + N233R + D254S | 1.6 +/− 0.2 |
| LVA714 | D27V + N33Q + G91A + N94R + D111A + G163K + L227F + T231R + N233R + Q249R + D254S | 1.1 +/− 0.0 |
| LVA773 | D27R + N33Q + G38A + G91T + D96E + D111A + T231R + N233R + D254S + P256T | 1.3 +/− 0.1 |
| LVA828 | N33Q + G91A + N94K + D111A + G163K + L227F + T231R + N233R + Q249R | 1.6 +/− 0.3 |
| LVA829 | N33Q + G91A + N94K + D111A + G163K + L227F + T231R + N233R + Q249R + D254S | 1.7 +/− 0.0 |
| LVA955 | N33Q + G91T + K98I + T114I + G163K + T231R + N233R + D254S | 3.3 +/− 1.0 |
| LVA956 | N33Q + G91T + K98I + G163K + T231R + N233R + D254S + P256L | 1.8 +/− 0.4 |
| LVA957 | N33Q + G91T + T114I + G163K + T231R + N233R + D254S + P256L | 2.3 +/− 0.5 |

TABLE 8d

Additional lipase variants with an improved performance in vitro

| Lipase | Substitutions as compared to SEQ ID NO: 2 | IF (A280) |
|---|---|---|
| | Diet I (pH 5 in gastric step) | |
| LVA012 | D27R + N33Q + G91A + D96E + L97Q + D111A + T231R + N233R + P256T | 2.1 +/− 0.5 |
| LVA013 | D27R + N33Q + G91A + D96E + L97Q + D111A + T231R + N233R + P256T | 1.6 +/− 0.0 |
| LVA023 | N33Q + E210D + T231R + N233R | 3.2 +/− 1.1 |
| LVA041 | N33Q + D111A + T231R + N233R | 2.2 +/− 0.6 |
| LVA043 | N33Q + G91T + T231R + N233R | 3.9 +/− 1.1 |
| LVA061 | D27Q + N33Q + T231R + N233R | 2.4 +/− 0.8 |
| LVA139 | Q9H + N33Q + D102E + T231R + N233R | 1.5 +/− 0.3 |
| LVA208 | N33Q + G91T + G163K + T231R + N233R | 1.4 +/− 0.1 |
| LVA216 | N33Q + E56Q + T231R + N233R | 1.9 +/− 0.2 |
| LVA231 | N33Q + I90L + G163L + T231R + N233R | 2.0 +/− 0.0 |
| LVA250 | N33Q + N94R + T231R + N233R | 1.9 +/− 0.5 |
| LVA275 | N33Q + T231R + N233R + D254S | 1.8 +/− 0.5 |
| LVA315 | N33Q + G91T + G163K + T231R + N233R + D254G | 1.9 +/− 0.3 |
| LVA317 | N33Q + G91T + G163K + T231R + N233R + D254S | 2.1 +/− 0.4 |
| LVA319 | N11R + N33Q + G91T + G163K + T231R + N233R + D254S | 2.3 +/− 0.8 |
| LVA341 | D27N + N33Q + G91T + G163K + T231R + N233R + D254S | 2.4 +/− 0.1 |
| LVA348 | N33Q + T231R + N233R | 1.6 +/− 0.3 |
| LVA349 | K98I + T231R + N233R + N251S | 1.7 +/− 0.5 |
| LVA368 | N33Q + G163P + T231R + N233R | 1.7 +/− 0.1 |
| LVA370 | N33Q + G163D + T231R + N233R | 2.0 +/− 0.4 |
| LVA387 | N33Q + G163T + T231R + N233R | 1.4 +/− 0.0 |
| LVA389 | N33Q + G163W + T231R + N233R | 1.5 +/− 0.0 |
| LVA437 | N33Q + G38A + G163A + T231R + N233R | 1.9 +/− 0.3 |
| LVA444 | N33Q + D111A + T231R + N233R + D254S | 1.2 +/− 0.2 |
| LVA449 | D27R + N33Q + G91A + D96E + L97Q + D111A + T231R + N233R + D254S + P256T | 1.4 +/− 0.1 |
| LVA473 | D27R + N33Q + G91T + D96E + L97Q + D111A + T231R + N233R + D254S + P256T | 1.4 +/− 0.4 |
| LVA486 | N33Q + T231R + N233R + D254Q | 1.9 +/− 0.1 |
| LVA488 | N33Q + T231R + N233R + D254I | 1.6 +/− 0.1 |
| LVA503 | N33Q + S216P + L227G + T231R + N233R + Q249R | 1.3 +/− 0.1 |
| LVA553 | N33Q + T231R + N233R + P256A | 1.1 +/− 0.1 |
| LVA564 | N33Q + T231R + N233R + P256L | 1.2 +/− 0.1 |
| LVA566 | N33Q + T231R + N233R + P256S | 1.7 +/− 0.2 |
| LVA620 | N33Q + G91T + N94S + D111A + V176I + T231R + N233R + D254S | 1.5 +/− 0.2 |
| LVA672 | N33Q + S115L + T231R + N233R | 1.7 +/− 0.1 |

TABLE 8d-continued

| Additional lipase variants with an improved performance in vitro | | |
|---|---|---|
| Lipase | Substitutions as compared to SEQ ID NO: 2 | IF (A280) |
| LVA675 | N33Q + G38A + G91T + G163K + T231R + N233R + D254S | 2.2 +/− 0.4 |
| LVA713 | D27V + N33Q + G91A + N94R + D111A + G163K + L227F + T231R + N233R + Q249R | 2.7 +/− 0.2 |
| LVA714 | D27V + N33Q + G91A + N94R + D111A + G163K + L227F + T231R + N233R + Q249R + D254S | 1.2 +/− 0.0 |
| LVA734 | N33Q + G161A + T231R + N233R | 1.3 +/− 0.1 |
| LVA801 | N33Q G38M T231R N233R | 3.3 +/− 0.9 |
| LVA803 | N33Q G38F T231R N233R | 3.2 +/− 0.4 |
| LVA828 | N33Q + G91A + N94K + D111A + G163K + L227F + T231R + N233R + Q249R | 2.0 +/− 0.9 |
| LVA829 | N33Q + G91A + N94K + D111A + G163K + L227F + T231R + N233R + Q249R + D254S | 2.8 +/− 1.5 |
| LVA955 | N33Q + G91T + K98I + T114I + G163K + T231R + N233R + D254S | 4.2 +/− 1.7 |
| LVA956 | N33Q + G91T + K98I + G163K + T231R + N233R + D254S + P256L | 2.6 +/− 0.8 |
| LVA957 | N33Q + G91T + T114I + G163K + T231R + N233R + D254S + P256L | 2.1 +/− 0.3 |

Example 8

Lipase Variants with Improved Stability at pH 3 in the Presence of Pepsin

The variants of Table 6 in Example 5 were screened for stability at pH 3 in the presence of pepsin, together with the variants of Table 9 below.

The variants were selected from two randomly mutagenized yeast libraries of amino acids 21 to 100 of SEQ ID NO: 1 and from a targeted yeast library of SEQ ID NO: 1 with the following changes targeted: D27X, E43X, E56X, D57DA, D62DA, E87EK, D96DL, E99X, D111X, D234X Q249QR, D254DN, from a targeted yeast library of SEQ ID NO:1 with G91T and G163K with the following changes targeted: N11R, D27RQNV, G38X, D96EW, K98X, T114I, K163WA, E210VD, R231I, D254SGQIK and P256TA, from a randomly mutagenized library of SEQ ID NO: 1 with G91T and G163K, from a randomly mutagenized library of SEQ ID NO:1 with D27R, G91N, N94R, D111A, S216P, L227G and P256T or were site-directed variants generated of SEQ ID NO: 1. The yeast is *Sachharoymces cerevisiae* JG169 (MATα; ura3-52; leu 2-3, 112; his 3-D200; pep 4-113; prd::HIS3; prbl::LEU2; cir+).

TABLE 9

| Lipase variants III | |
|---|---|
| Variant designation | Substitutions as compared to SEQ ID NO: 2 |
| LVAR0002b | T32I + G91V + T231R + N233R |
| LVAR0011a | G91A + T231R + N233R |
| LVAR0014 | N33Y + G91W + N94K + T231R + N233R |
| LVAR0015 | P42L + D57N + G91E + T231R + N233R |
| LVAR0016 | K98I + T231R + N233R |
| LVAR0017 | V60L + G91V + T231R + N233R |
| LVAR0048 | E43K + E56S + E87K + T231R + N233R |
| LVAR0055 | E43V + G91R + T231R + N233R |
| LVAR0059 | E43M + E87K + D96L + E99P + T231R + N233R |
| LVAR0066 | E43D + E56A + D57A + E87K + D111A + T231R + N233R |
| LVAR0068 | E87K + L147S + T231R + N233R |
| LVAR0070 | E43D + E87K + D96L + E99P + E239V + T231R + N233R |
| LVAR0071 | E43K + E56A + E87K + D234K + T231R + N233R |

TABLE 9-continued

| Lipase variants III | |
|---|---|
| Variant designation | Substitutions as compared to SEQ ID NO: 2 |
| LVAR230 | D27R + N33Q + E43K + K46M + I90V + G91N + N94R + D111A + T114I + S216P + L227G + T231R + N233R + P256T |
| LVAR226 | G23E + D27R + N33Q + L52R + G91N + N94R + D111A + T114I + V141E + S216P + L227G + T231R + N233R + P256T |
| LVAR287 | N33Q + G38W + G91T + T114I + G163K + E210D + T231R + N233R + P256T |
| LVAR288 | D27I + N33Q + G91T + D96E + K98T + T114I + G163K + E210D + T231R + N233R + P256T |
| LVAR280 | N33Q + G91T + D96E + K98T + T114I + T231R + N233R + G163S |
| LVAR286 | N33Q + G38W + G91T + T114I + G163K + E210V + T231R + N233R |
| LVAR214 | Q4P + D27R + N33Q + G91N + N94R + D111A + R205I + L206F + S216P + L227G + T231R + N233R + P256T |
| LVAR281 | N33Q + G91T + D96E + K98T + T114I + G163K + E210D + T231R + N233R |
| LVAR205 | D27R + N33Q + T37K + N71I + G91N + N94R + K98I + D111A + S216P + L227G + T231R + N233R + P256T |
| LVAR215 | Q4H + D27R + N33Q + G91N + N94R + D111A + V154L + S216P + L227G + T231R + N233R + P256T |
| LVAR277 | N33Q + G91T + D96E + K98T + T114I + G163S + E210V + T231R + N233R + D254K + P256A |
| LVAR282 | N33Q + G91T + T114I + G163K + E210D + T231R + N233R + D254G + P256A |
| LVAR209 | D27R + N33Q + L52I + V60E + G91N + N94R + D111A + T114I + V168M + E210D + S216P + L227G + T231R + N233R + P256T |
| LVAR223 | D27R + N33Q + G91N + N94R + D111A + T114I + R179T + S216P + L227G + T231R + N233R + P256T |
| LVAR231 | D27R + A30V + N33Q + G91N + N94R + G109A + D111A + G190D + S216P + L227G + T231R + N233R + P256T |
| LVAR204 | D27R + N33Q + G91N + N94R + K98I + D111A + N162S + S216P + L227G + T231R + N233R + P256T |
| LVAR235 | N26H + D27R + N33Q + G91N + N94R + D111A + V154F + G190C + S216P + L227G + T231R + N233R + P256T |
| LVAR284 | D27N + N33Q + G91T + T114I + G163S + E210D + T231R + N233R + P256T |
| LVAR225 | D27R + N33Q + G91N + N94R + D111A + S216P + L227G + T231R + N233R |
| LVAR205 | D27R + N33Q + T37K + N71I + G91N + N94R + K98I + D111A + S216P + L227G + T231R + N233R + P256T |
| LVAR283 | D27R + N33Q + G91T + T114I + G163W + E210D + T231R + N233R |
| LVAR219 | D27R + N33Q + G91N + N94R + K98I + D111A + S216P + L227G + T231R + N233R + P256T |
| LVAR220 | D27R + N33Q + G91N + N94R + L97M + D111A + S216P + T226N + L227G + T231R + N233R + P256T + L269H |
| LVAR216 | D27R + N33Q + G91N + N94R + D111A + V154I + S216P + L227G + T231R + N233R + P256T |
| LVAR290 | N33Q + G91T + T114I + E210V + T231R + N233R + D254K + P256A |
| LVAR218 | D27R + N33Q + N71S + G91N + N94R + D111A + H135D + S216P + L227G + T231R + N233R + P256T |
| LVAR285 | N33Q + G91T + T114I + G163K + E210D + T231R + N233R |
| LVAR208 | D27R + N33Q + I76T + G91N + N94R + R108M + D111A + S216P + L227G + T231R + N233R + P256T |
| LVAR207 | D27R + N33Q + N39S + G91N + N94R + D111A + S216P + L227G + T231R + N233R + P256T |
| LVAR234 | D27R + N33Q + A49T + G91N + N94R + D111A + Y138F + G163R + S216P + L227G + T231R + N233R + P256T |
| LVAR828 | N33Q + G91A + N94K + D111A + G163K + L227F + T231R + N233R + Q249R |
| LVAR955 | N33Q + G91T + K98I + T114I + G163K + T231R + N233R + D254S |
| LVAR956 | N33Q + G91T + K98I + G163K + T231R + N233R + D254S + P256L |

Principle

The screening process measures residual lipase activity after a 3 hour treatment at pH 3.0 and room temperature in the presence of 75 ug/mL pepsin. The residual lipase activity is measured in a rate assay monitoring activity over time to allow very high activity and very low activity lipases to be detected during the screening event.

In primary screens of variants, a sufficiently large dilution is performed on the broth sample in order to minimize the effects of media or fermentation components on the test conditions. Variants that make it past the primary phase undergo more testing in the follow up screening by adding more dilutions and replicates of the test samples.

Materials and Methods

Primary Screen Medium:

1.7 g of yeast nitrogen base (YNB) with ammonium sulfate (Bio 101, Cat #4027-532), 0.8 g of Complete Supplement Mixture-Uracil (CSM-ura) w/40 mg adenine (ADE) (Bio 101, Cat #4512-722), 5 g of Casamino acids (BD, Cat #223050), 100 ml of 50% Glucose, 50 ml of 0.5 M $K_2HPO_4$ (Potassium phosphate-dibasic), 1 ml of 100 mM $CuSO_4$-$5H_2O$ (JD Baker, Cat#1843-01), 1 ml of 100 mg/mL ampicillin in a total volume adjusted to 1 l with de-ionized water. The medium was filter sterilized and stored at 4° C.

Optimized Medium:

6.7 g of YNB with ammonium sulfate (Bio 101, Cat #4027-532), 5.9 g of succinic acid (Sigma S-9512), 0.8 g of CSM-ura w/40 mg ADE (Bio 101, Cat #4512-722), 20 g of galactose (Sigma, Cat#G-0625), 10 g of glucose, 1 ml of 100 mM $CuSO_4$-$5H_2O$ and 1 ml of 100 mg/mL ampicillin. The pH is adjusted to 6.6 with NaOH and the volume is adjusted to 1 l with de-ionized water. The medium is filter sterilized and stored at 4° C.

Seed Culture Medium:

Mix following ingredients: 6.7 g of YNB with ammonium sulfate (Bio 101, Cat #4027-532), 5 g of Casamino acids (BD, Cat #223050), 100 ml of 0.5 M succinic acid (Sigma S-9512), 855 ml of de-ionized $H_2O$. Autoclave the mixture. Add 2 ml of 10 mg/mL chloramphenicol and 40 ml of 50% Glucose. Store at 4° C.

Stock Solutions for Making Substrate and Pepsin Treatment:

1. 10% Triton-X100 (w/v)
2. 1 M TRIS, pH 8.0
3. 10% (680 mM) $CaCl_2*2H_2O$
4. 100 mM Citric Acid, pH 3.0
5. 5 mg/mL Porcine Pepsin (Sigma P-6887, 3280 U/mg solid, 3370 U/mg protein) made up in 100 mM Citric Acid, 0.01% Triton-X100
6. 50 mM 4-nitrophenol (PNP) Palmitate made up in 10% Triton-X100

Substrate for Lipase Activity Assay:

1 mM PNP-Palmitate, 1.2% Triton-X100, 4 mM $CaCl_2$, 100 mM TRIS, pH 8.0

Pepsin Treatment Solution:

150 ug/mL pepsin, 4 mM $CaCl_2$, 0.01% Triton-X100, 50 mM Citrate, pH 3.0

Diluent:

0.01% Triton-X100, 10 mM NaCl

Enzymes:

Broth samples of lipase variants for primary screens were derived from individual clones picked off agar plates into Primary Screen Medium in 96-well plates.

Growth of Cultures:

Three media recipes were used to grow lipase variants. Since expression level at primary screen level is not critical, Primary Screen Medium was used for earlier screen stage. Single lipase variant expressing yeast colonies were picked Into 180 uL of Primary Screen Medium in 96-well plates and grown at 30° C. and 250 rpm for 4-6 days for the primary screening samples.

For the secondary screening, 20 uL of culture from the primary screening plate was transferred into 1 mL of Seed Culture Medium in 24-well plates and grown overnight at 30° C. and 250 rpm. Expression of the lipase was achieved by inoculating 20 uL of the Seed Culture into 1 mL of Optimized Medium in 24-well plates at 30° C. and 250 rpm for 4-6 days.

For any subsequent screening, single yeast colonies were picked into 1 mL of Seed Culture Medium in 24-well plates and grown overnight at 30° C. and 250 rpm. Expression of the lipase was achieved by inoculating 20 uL of the Seed Culture into 1 mL of Optimized Medium in 24-well plates at 30° C. and 250 rpm for 4-6 days. Optimized medium was used for growing in a 24-well plate and a shake flask to maximize the protein expression level.

Screening Procedure:

In primary screens, samples were diluted 25-fold in diluent, then 5 uL was added to 384 well plates containing 5 uL of either diluent or pepsin treatment solution.

After 3 hours at room temperature, substrate was added to each sample as follows: The pepsin-treated samples were mixed with 55 uL substrate+5 uL diluent, the untreated samples were mixed with 55 uL substrate+5 uL pepsin-treatment solution. (The pepsin pH is 3.0 and without compensating for the change in pH, the activity assay will be run at two different pH values, so this normalizes the assay pH without having an effect on stability of lipase (by adding it at the end when the pH of the substrate is sufficient to raise the overall pH to 8.0, where pepsin is not active). $OD_{405}$ readings were taken 6 times per 384-well plate; as early as 15 minutes after substrate addition and as long as 18 hours after substrate addition and were expressed as mOD (milli OD) per hour. Data that falls in the linear range was collected and the residual lipase activity of each pepsin-treated sample was compared with the residual lipase activity of the corresponding untreated sample. This is reported below as % residual activity (% RA); calculated by dividing the rate of the treated condition by the rate of the untreated condition and multiplying the result by 100.

Automation may be accomplished using a system comprised of a Biomek FX workstation which functions to move plates and perform pipetting steps, a DXT 880 plate reader to record data from the assay plates, a carousel and conveyor belt system to transport plates to and from the workstation. This procedure accepts samples in 96-well plate formats, performs dilutions in the same format, then uses 384-well plates for the treatment and assay steps.

Results:

The relative residual activities for each lipase variant as measured after the secondary screen are shown in Table 10 below. Each of these variants has an improved RA (stability at pH 3 in the presence of pepsin) as compared to the lipase of amino acids 1-269 of SEQ ID NO: 2.

TABLE 10

Residual lipase activity after incubation at pH 3 in the presence of pepsin

| Enzyme tested | Residual Activity (RA), % |
|---|---|
| SEQ ID NO: 2 | 2.3 |
| SEQ ID NO: 1 | 9.7 |
| LVAR0002b | 37 |
| LVAR0003 | 37 |
| LVAR0011a | 58 |

TABLE 10-continued

| Residual lipase activity after incubation at pH 3 in the presence of pepsin | |
|---|---|
| Enzyme tested | Residual Activity (RA), % |
| LVAR0013 | 56 |
| LVAR0014 | 80 |
| LVAR0015 | 70 |
| LVAR0016 | 37 |
| LVAR0017 | 62 |
| LVAR0045 | 33 |
| LVAR0046 | 61 |
| LVAR0047 | 45 |
| LVAR0048 | 39 |
| LVAR0050 | 45 |
| LVAR0051 | 40 |
| LVAR0052 | 58 |
| LVAR0053 | 44 |
| LVAR0054 | 30 |
| LVAR0055 | 66 |
| LVAR0056 | 37 |
| LVAR0057 | 71 |
| LVAR0058 | 42 |
| LVAR0059 | 36 |
| LVAR0061 | 63 |
| LVAR0062 | 31 |
| LVAR0063 | 59 |
| LVAR0064 | 33 |
| LVAR0065 | 40 |
| LVAR0066 | 34 |
| LVAR0067 | 32 |
| LVAR0068 | 57 |
| LVAR0069 | 45 |
| LVAR0070 | 52 |
| LVAR0071 | 60 |
| LVAR0072 | 52 |
| LVAR0101 | 95 |
| LVAR0102 | 76 |
| LVAR0106 | 86 |
| LVAR230 | 91 |
| LVAR226 | 100 |
| LVAR287 | 96 |
| LVAR288 | 94 |
| LVAR280 | 93 |
| LVAR286 | 91 |
| LVAR214 | 90 |
| LVAR281 | 90 |
| LVAR205 | 89 |
| LVAR215 | 88 |
| LVAR277 | 87 |
| LVAR282 | 87 |
| LVAR209 | 86 |
| LVAR223 | 85 |
| LVAR231 | 84 |
| LVAR204 | 84 |
| LVAR235 | 83 |
| LVAR284 | 83 |
| LVAR225 | 81 |
| LVAR205 | 80 |
| LVAR283 | 80 |
| LVAR219 | 80 |
| LVAR220 | 79 |
| LVAR216 | 79 |
| LVAR290 | 78 |
| LVAR218 | 78 |
| LVAR285 | 78 |
| LVAR208 | 77 |
| LVAR207 | 76 |
| LVAR234 | 75 |
| LVAR828 | 75 |
| LVAR955 | 96 |
| LVAR956 | 85 |

Example 9

Lipase Variants with Improved Activity in the Presence of Bile Salts

In order to identify lipase variants with improved activity in the presence of bile salts the following assay was developed. The assay measures lipase activity in the presence of 2 mM bile salts as compared to conditions without bile salts. The test is set up such that lipase activity is measured in a rate assay monitoring activity over time to allow very high activity and very low activity lipases to be detected. This assay is automated to precisely control the timing of the addition of reagents and adjustments of the pH of the reactions from pH 5.0, where the lipase reacts with the substrate at low pH, to pH 8.0, a pH that allows the released PNP group to be read at OD 405. The plates are read immediately after the pH adjustment occurs.

Stock Solutions for Assay Substrate and Bile Salts Treatment:

1. 10% Triton-X100 (w/v)
2. 100 mM TRIS, pH 8.0
3. 100 mM Succinate, pH 5.0
4. 10% (680 mM) $CaCl_2$*$2H_2O$
5. 20 mM Bile Salts (Sigma B-8756) made up in distilled water
6. 50 mM 4-nitrophenol (PNP) Oleate made up in 10% Triton-X100

Substrate for Lipase Activity Assay:

1 mM PNP-Oleate, 1.2% Triton-X100, 2 mM $CaCl_2$, 25 mM Succinate, pH 5.0

Diluent:

0.01% Triton-X100, 10 mM NaCl

Enzymes:

Purified lipase samples are diluted in diluent to approximately 8 micrograms/mL for the automated method. The concentration of the purified lipase samples was determined from the absorbance at 280 nm using the extinction coefficient 1.24 $A_{280}$/mg.

Liquid Based Bile Salts Assay Screening Procedure:

Enzyme samples are diluted 25-fold and 200-fold in diluent, then 10 micro-L is added to either 23 micro-L water or 23 micro-L 20 mM Bile salts in 96-well plate reaction plates. After this, 200 micro-L of the substrate (1 mM PNP Oleate in 25 mM Succinate, 2 mM $CaCl_2$, 1.2% Triton-X100, pH 5.0), is added and mixed. Immediately after mixing, 60 micro-L is removed and 15 micro-L is pipetted into four separate 384-well plates where the 4 quadrants (4×96) are used to set up the "+" and "−" bile salts conditions for each of 2 dilutions of the lipase samples. The four 384-well plates are used to set up 4 time points (such that each plate has the 2 dilutions of the lipase each "+" and "−" bile salts). After 1, 2, 3, and 4 hours 60 micro-L of 100 mM TRIS, pH 8.0 is added to the appropriate plate and quadrant and read (OD 405 and OD 540) immediately. ODs between ~0.1 and 0.475 are the linear range used for this assay. A ratio of the activity in the presence of bile salts at pH 5.0 is expressed as a percentage by calculating the average of all linear data corrected for time and dilution for the "bile salts" activity divided by the average of all linear data corrected for time and dilution for the "no bile salts" activity. The ratio of activity versus the reference (variant N33Q of SEQ ID NO: 1) is calculated by dividing the ratio of the variants plus and minus bile salts by the ratio of the reference plus and minus bile salts and is reported as a fold improvement (e.g., 3× means 300%).

TABLE 11

| Variant | Bile Salt Ratio Improvement vs Reference | Substitutions as compared to SEQ ID NO: 2 |
|---|---|---|
| LVAR714 | 3X | D27V + N33Q + G91A + N94R + D111A + G163K + L227F + T231R + N233R + Q249R + D254S |
| LVAR828 | 3X | N33Q + G91A + N94K + D111A + G163K + L227F + T231R + N233R + Q249R |
| LVAR1042 | 4X | G23E + D27R + N33Q + L52R + G91N + N94R + D111A + T114I + V141E + S216P + L227G + T231R + N233R + P256T |
| LVAR1043 | 3X | D27R + N33Q + E43K + K46M + I90V + G91N + N94R + D111A + T114I + S216P + L227G + T231R + N233R + P256T |
| LVAR861 | 3X | G23E + D27R + N33Q + L52R + G91N + N94R + D111A + T114I + V141E + S216P + L227G + T231R + N233R + P256T |
| LVAR863 | 2.5X | D27R + N33Q + E43K + K46M + I90V + G91N + N94R + D111A + T114I + S216P + L227G + T231R + N233R + P256T |
| LVAR290 | 3X | N33Q + G91T + T114I + E210V + D254K + P256A |
| LVAR277 | 2X | N33Q + G91T + D96E + K98T + T114I + G163S + E210V + D254K + P256A |
| LVAR209 | 2X | L52I + V60E + T114I + V168M + E210D |
| LVAR234 | 2X | D27R + N33Q + A49T + G91N + N94R + D111A + Y138F + G163R + S216P + L227G + T231R + N233R + P256T |
| LVAR208 | 2X | D27R + N33Q + I76T + G91N + N94R + R108M + D111A + S216P + L227G + T231R + N233R + P256T |
| LVAR230 | 2X | D27R + N33Q + E43K + K46M + I90V + G91N + N94R + D111A + T114I + S216P + L227G + T231R + N233R + P256T |

Example 10

In Vivo Digestibility Trial (Screening Test)

Selected purified *Humicola lanuginosa* lipase variants of the invention were studied in a lipase screening test in female Göttingen minipigs (Ellegaard) with induced Pancreatic Exocrine Insufficiency (PEI). The amino acid sequences of the variants are found in Tables 1, 7 and 8. The efficacy was compared to that of variant N33Q of the lipase having amino acids 1-269 of SEQ ID NO: 1 (variant LV2934; reference lipase of Table 12). Pancreatic Exocrine Insufficiency (PEI) was induced in the minipigs by ligation of the pancreatic duct, and they were also fitted with an ileo-caecal re-entrant cannula, all under isofluorane anaesthesia and at a weight of about 25 kg, as described in Tabeling et al. (Tabeling et al. (1999): "Studies on nutrient digestibilities (pre-caecal and total) in pancreatic duct-ligated pigs and the effects of enzyme substitution", J. Anim. Physiol. A. Anim. Nutr. 82: 251-263) and in Gregory et al. (Gregory et al. (1999): "Growth and digestion in pancreatic duct ligated pigs, Effect of enzyme supplementation" in "Biology of the Pancreas in Growing Animals" (Pierzynowski & Zabielski eds), Elsevier Science BV, Amsterdam, pp 381-393). A period of at least 4 weeks was allowed for recovery from surgery, before studies were commenced. Prior to study begin, the PEI status of each pig was confirmed via the stool chymotrypsin test (commercially available from Immundiagnostik AG, Wiesenstrasse 4, D-64625 Bensheim, Germany, with catalogue No. K 6990).

Assay

The screening test for lipase activity was performed in two groups of 3 or 4 PEI minipigs. During the studies, the pigs were housed in modified metabolism cages and allowed free access to water and fed two meals per day.

Test Meal 247.2 g milk; 1×87 g sachet Calshake from Fresenius Kabi (2077KJ/100 g); 29.9 g olive oil; 9.88 g Methocel (Methocel E5, from Colorcon GmbH); and 0.368 g chromic oxide. Calshake contains 24.4% fat, 3.3% lactose, 64.9% carbohydrate (49% sugar), 4.3% protein.

The milk and chromic oxide were homogenized with an Ultraturax homogenizer (9500 rpm, ca. 1 min), after which the oil was mixed in and again homogenized for 1-2 minutes. Then the Calshake was mixed in (stirred with mixer for 1-2 min) and finally the Methocel was slowly added while mixing with the Ultraturax, and the whole meal was then homogenized for approximately 3 minutes.

Performance

To assess lipase efficacy, the pigs were fed a single test meal (containing 51.6 g fat) into which differing amounts of a reference lipase or similar amounts of lipase variants were mixed immediately before feeding.

The reference lipase LV2934 was dosed at 0.124, 1.24, 4.96, or 18.61 mg enzyme protein/meal (corresponding to 500, 5000, 20000, and 75000 FIP U lipase/meal, respectively), and the lipase variants of the invention were also dosed according to mg enzyme protein (1.24, 4.96, and 18.61 mg/meal), in order to compare the in vivo efficacy with LV2934. The studies were performed according to a Latin Square design.

Ileal chyme was collected for a total of 8 h after first appearance of the meal marker in the ileum (green chyme) and two hour samples were frozen at −20° C. At least one day washout was allowed between separate determinations. A low-fat, liquid meal was given in the evening before each test to reduce the likelihood of interference of meal contents from non-test meals.

Analysis

The frozen ileal chyme samples were freeze-dried, milled and analysed for dry matter (DM) and fat (Naumann & Bassler 1993; Die chemische Untersuchung von Futtermitteln, 3. edition, VDLUFA-Verlag, Darmstadt (VDLUFA=Verband Deutscher Landwirtschaftlicher Untersuchungs- und Forschungsanstalten). DM was estimated by weight after freeze-drying followed by 8 h incubation at 103° C.; crude fat content of the dried sample was determined by acid hydrolysis and petrol ether extraction using a filter bag technique in an ANKOMXT15 extractor (which is available from Ankom Technology, Macedon, N.Y., US; capable of performing 15 extractions at a time); $Cr_2O_3$ was oxidized to chromate and chromium content was calculated as described by Petry and Rapp in Zeitung für Tierphysiologie (1970), vol. 27, p. 181-189 (Petry & Rapp, 1970, *Z. Tierphysiol.* 27: 181-189) via extinction at 365 nm (spectrophotometer).

Digestibility values (coefficient of fat absorption; CFA) were estimated by the marker method according to the formula:

$$CFA\ (\%) = 100 - \frac{[\%\ Cr_2O_3\ \text{in feed}]\cdot[\%\ \text{fat in ileal chyme}]}{[\%\ Cr_2O_3\ \text{in ileal chyme}]\cdot[\%\ \text{fat in feed}]}\cdot 100$$

Results and Conclusion

The CFA results are shown in Table 12. The lipase dosage is indicated in milligram of enzyme protein per meal (mg/meal).

TABLE 12

Effect of lipase variants of the invention on CFA (Coefficient of Fat Absorption)

| Lipase variant | 0 | 0.124 (mg/meal)**** | 1.24 (mg/meal)**** | 4.96 (mg/meal)**** | 18.61 (mg/meal)**** |
|---|---|---|---|---|---|
| No lipase | 14.56 +/− 5.94 | | | | |
| Control animals (not PEI) | 85.8 +/− 3.2 | | | | |
| Reference lipase (LV2934)**** | | 17.53 +/− 4.95*** | 35.41 +/− 5.41* | 54.69 +/− 1.52** | 65.48 +/− 5.88* |
| LVA129 | | | 30.02 | 58.47 | 75.47 |
| LVA147 | | | 41.44 | 54.84 | 74.00 |
| LVA238 | | | 37.74 | 57.33 | 72.05 |
| LVA315 | | | 37.03 | 64.87 | 80.91 |
| LVA317 | | | 43.7 | 68.57 | 81.14 |
| LVA319 | | 27.07 | 63.72 | 73.43 | 83.82 |
| LVA368 | | | 34.21 | 51.45 | 75.50 |

*Standard Deviation calculated from 6 independent tests and including the testing of LVA027 and LVA348

**Standard Deviation calculated from 2 independent tests (LVA027 and LVA348)

***Standard Deviation calculated from 4 independent tests

****Corresponding to the following amounts of FIP U of reference lipase LV2934: 500, 5000, 20000 and 75000 FIP Units determined by pancreatic FIP test, respectively Additional lipase variants including LV1330, LV1855, LV1865, LV1874, LV1889, LVA043, LVA049, LVA012, LVA023, LVA099, LVA041, LVA061, LVA103, LV1857, LV1232, and LVA473 are studied in the same screening test.

All lipase variants tested were active in vivo and caused a dose-dependent improvement in CFA. Lipase variants LVA129, LVA147, LVA238, LVA315, LVA317, LVA319, and LVA368 are all considerably improved as compared to the reference lipase.

Example 11

Full In Vivo Digestibility Trial

The purified lipase variant LVA319 was tested in a full digestibility study in a group of 6 female Göttingen minipigs (Ellegaard). The efficacy has been compared to that of the lipase of SEQ ID NO: 1 tested in PEI minipigs fed the same diet. Pancreatic Exocrine Insufficiency (PEI) was induced in the minipigs by ligation of the pancreatic duct, and they were also fitted with an ileo-caecal re-entrant cannula, all under isofluorane anaesthesia and at a weight of about 25 kg, as described in Tabeling et al. (Tabeling et al., 1999, "Studies on nutrient digestibilities (pre-caecal and total) in pancreatic duct-ligated pigs and the effects of enzyme substitution", *J. Anim. Physiol. A. Anim. Nutr.* 82: 251-263) and in Gregory et al. (Gregory et al., 1999, "Growth and digestion in pancreatic duct ligated pigs, Effect of enzyme supplementation" in "Biology of the Pancreas in Growing Animals" (Pierzynowski & Zabielski eds), Elsevier Science BV, Amsterdam, pp. 381-393). A period of at least 4 weeks was allowed for recovery from surgery, before studies were commenced. Prior to study begin, the PEI status of each pig was confirmed via the stool chymotrypsin test (commercially available from Immundiagnostik AG, Wiesenstrasse 4, D-64625 Bensheim, Germany, with catalogue No. K 6990).

Assay

During the studies, the pigs were housed in pens on a 12:12 h light-dark cycle and allowed free access to water and fed two meals per day.

Test Meal

During the study, the pigs were fed twice daily (08.00, 20.00 h) with 300 g of a high-fat "human-like" diet containing: 200 g double-milled diet (from Altromin), plus 25 g olive oil, 75 g cream and 0.625 g $Cr_2O_3$ mixed with 1 litre water (see Table 13). The test meal contained 31% fat, 15% protein, 36% starch as well as vitamins, minerals and trace elements as per the nutritional requirements for pigs.

TABLE 13

Composition of experimental "human-like" diet

| Dietary components | Content (g/kg wet weight) |
|---|---|
| Poultry meal | 73 |
| Pea meal | 73 |
| Casein (precipitated under acid conditions) | 73 |
| Wheat flour | 290 |
| Potato starch | 290 |
| Lard | 125 |
| Vitamins, minerals, trace elements | 76 |
| To 200 g of the above mixture were added: | |
| Cream (32% fat) | 75 g |
| Olive oil | 25 g |
| Chromic oxide | 0.625 g |
| Water | 1000 ml |

The cream, and olive oil followed by tap water and finally the different amounts/different enzyme supplements were mixed into the pre-weighed dry ration (including the chromic oxide marker) shortly before the pigs were fed.

Performance

To assess lipase efficacy, the pigs were fed two 300 g test meals/day into which differing amounts of one or other of the two lipases were mixed immediately before feeding. The amount of each lipase administered is shown in brackets in Table 15, viz. the activities in microbial FIP U lipase/meal (lipase FIP units, see Example 1). Each enzyme dosage was fed for 14 days: the pigs were fed the high-fat diet plus each new enzyme dosage for 9 days after which all faeces were collected over the next 5 days, weighed and stored at −20° C. until analysis.

Analysis

The frozen faeces from each pig were freeze dried, weighed again and milled. Aliquots of each of the 5 day milled samples (according to the daily faecal production) were then pooled and mixed together; i.e., giving one pooled sample for each pig for each dose of enzymes. From each pooled sample the content of dry matter and crude fat were determined (Naumann & Bassler 1993; Die chemische Untersuchung von Futtermitteln, 3. edition, VDLUFA-Verlag, Darmstadt (VDLUFA=Verband Deutscher Landwirtschaftlicher Untersuchungs- und Forschungsanstalten). Dry matter was estimated by weight after freeze-drying followed by 8 h incubation at 103° C.; crude fat content of the dried sample was determined by acid hydrolysis and petrol ether extraction using a filter bag technique in an ANKOM$^{XT15}$ extractor; $Cr_2O_3$ was oxidized to chromate and chromium content calculated as described by Petry and Rapp in Zeitung für Tierphysiologie, 1970, vol. 27, p. 181-189. (Petry & Rapp 1970; Z. Tierphysiol. 27; 181-189) via extinction at 365 nm (spectrophotometer).

Digestibility values (coefficient of fat absorption; CFA) were estimated by the marker method according to the formula:

$$CFA\ (\%) = 100 - \frac{[\%\ Cr_2O_3\ \text{in feed} \cdot \%\ \text{fat in faeces} \cdot 100]}{[\%\ Cr_2O_3\ \text{in faeces} \cdot \%\ \text{fat in feed}]}$$

Results and Conclusion

From the results in Table 14 it is apparent that lipase variant LVA319 performs much better than the reference lipase of SEQ ID NO: 1.

The lipase of the invention caused a very strong and dose-dependent improvement in fat digestibility, already showing a highly efficient improvement at the lowest dose tested.

TABLE 14

Influence of enzyme supplementation on CFA (Coefficient of Fat Absorption)

| Enzyme Supplement | 0 | Low | Medium | High |
|---|---|---|---|---|
| No supplement | 21.7 ± 4.5 | | | |
| Reference lipase (SEQ ID NO: 1) | | 46.3 +/− 4.9 (40101 FIP U) | 59.2 +/− 7.0 (155743 FIP U) | 75.6 +/− 4.7 (1168069 FIP U) |

TABLE 14-continued

Influence of enzyme supplementation on CFA (Coefficient of Fat Absorption)

| Enzyme Supplement | 0 | Low | Medium | High |
|---|---|---|---|---|
| Lipase variant LVA319 | | 59.2 +/− 4.4 (9538 FIP U) | 72.0 +/− 4.3 (38150 FIP U) | 81.4. +/− 1.3 (114450 FIP U) |

Example 12

Pharmaceutical Compositions

Pellets

A liquid lipase concentrate of purified lipase variant LVA129 (tested in vivo in Example 10) is prepared. The liquid concentrate is dried by conventional means, and the lipase protein content of the dried powder is measured and should preferably lie above 50%. Then, 500 g dried lipase powder is dry pre-mixed together with 200 g microcrystalline cellulose and 300 g polyethylene glycol 4000 (Macrogol™ 4000) in a commercially available mixer. A sufficient amount of a commonly used wetting agent is added and the resulting wet mass is thoroughly mixed at room temperature. The homogenized mass is then extruded in a commercially available extruder fitted with a piercing die having a hole diameter of 0.8 mm to form cylindrical pellets. The extrudate produced is rounded to spherical pellets with a commercially available spheronizer by adding the necessary amount of a commonly used wetting agent. The pellets are dried at a product temperature of approximately 40° C. in a commercially available vacuum dryer. The dried pellets are then separated by using a mechanical sieving machine with 0.7 and 1.4 mm screens. The sieve fractions of ≧0.7 mm and ≦1.4 mm are collected and filled in portions of 200 mg pellets each in capsules of size 2.

The resulting pellets are tested for lipolytic activity by applying the Lipase pH-stat assay described in Example 1.

The resulting pellets are tested for disintegration according to Pharm. Eur. 2.9.1. (Section "Disintegration of tablets and capsules") (test solution: 0.1 M malonic acid, pH 6.0-500 mL, 37° C.).

The invention claimed is:

1. An isolated variant lipase which (a) has at least 90% sequence identity to the sequence of amino acids 1-269 of SEQ ID NO: 2; and (b) has lipase activity; and which, (c) as compared to the sequence of amino acids 1-269 of SEQ ID NO: 2, comprises the four-fold substitution N33Q+T231R+N233R+D254S and is selected from the following:

N33Q+T231R+N233R+D254S;
N33Q+D96N+T231R+N233R+D254S;
N33Q+E210V+T231R+N233R+D254S;
N11R+N33Q+E210V+T231R+N233R+D254S;
N33Q+G91T+G163K+T231R+N233R+D254S;
N11R+N33Q+G91T+G163K+T231R+N233R+D254S;
D27N+N33Q+G91T+G163K+T231R+N233R+D254S;
N33Q+D111A+T231R+N233R+D254S;
D27R+N33Q+G91A+D96E+L97Q+D111A+T231R+N233R+D254S+P256T;
N33Q+G91T+N94R+T231R+N233R+D254S;
N33Q+W117L+T231R+N233R+D254S;
N33Q+G91T+N94R+T231R+N233R+D254S;
N33Q+L227F+T231R+N233R+D254S;
D27R+N33Q+G91T+D96E+L97Q+D111A+T231R+N233R+D254S+P256T;
D27R+N33Q+G91T+D96E+D111A+T231R+N233R+D254S+P256T;
D27R+N33Q+E56Q+D57N+G91N+N94R+D111S+S216P+L227G+T231R+N233R+D254S+P256T;
D27R+N33Q+G91N+N94R+D111A+S216P+L227G+T231R+N233R+D254S+P256T;
D27R+N33Q+G91N+N94R+D111A+S216P+L227G+T231R+N233R+D254S+P256T;
D27R+N33Q+G91N+N94R+D111S+A155V+S216P+L227G+T231R+N233R+D254S+P256T;
D27R+N33Q+G91N+N94R+D111S+S216P+L227G+T231R+N233R+D254S+P256T;
N33Q+D111A+T231R+N233R+D254S;
N33Q+D111A+W117L+T231R+N233R+D254S;
N33Q+G91T+N94S+D111A+V176I+T231R+N233R+D254S;
D27R+N33Q+L227G+T231R+N233R+Q249R+D254S;
N33Q+G38A+G91T+G163K+T231R+N233R+D254S;
D27V+N33Q+G91A+N94R+D111A+G163K+L227F+T231R+N233R+Q249R+D254S;
D27R+N33Q+P136H+L227G+T231R+N233R+Q249R+D254S;
N33Q+G91T+D96N+D111A+V176I+T231R+N233R+D254S;
N33Q+G91T+N94S+D111A+V176I+T231R+N233R+D254S;
D27R+N33Q+G91T+D96E+D111A+G163K+T231R+N233R+D254S+P256T;
D27R+N33Q+G91T+D96E+D111A+G163A+T231R+N233R+D254S+P256T;
D27R+N33Q+G38A+G91T+D96E+D111A+T231R+N233R+D254S+P256T;
N11R+N33Q+G91T+W117I+G163K+T231R+N233R+D254S;
D27R+N33Q+G38A+G91T+D96E+D111A+G163K+T231R+N233R+D254S+P256T;
N11R+N33Q+G91T+W117I+G163K+T231R+N233R+D254S;
D27R+N33Q+G38A+G91T+D96E+D111A+G163A+T231R+N233R+D254S+P256T;
D27R+N33Q+V176Q+L227G+T231R+N233R+Q249R+D254S;
N33Q+G91A+N94K+D111A+G163K+L227F+T231R+N233R+Q249R+D254S;
N11R+N33Q+G91T+G163K+V176Q+T231R+N233R+D254S;
D27R+N33Q+W117I+V176Q+L227G+T231R+N233R+Q249R+D254S;
N11R+N33Q+G38A+G91T+G163K+T231R+N233R+D254S;
D27R+N33Q+G91T+D96E+L97Q+D111A+T231R+N233R+D254S+P256T;
N11R+N33Q+G91T+S115L+G163K+T231R+N233R+D254S;
N11R+N33Q+G91T+G163K+V176W+T231R+N233R+D254S;
E1D+N33Q+G91T+N94R+D111A+W117L+T231R+N233R+D254S;
N11R+D27R+N33Q+E56Q+D57N+G91N+N94R+D111S+G163T+S216P+L227G+T231R+N233R+D254S+P256T;
D27R+N33Q+E56Q+D57N+G91N+N94R+D111S+G163T+S216P+L227G+T231R+N233R+D254S+P256T;

N11R+D27R+N33Q+E56Q+D57N+G91N+N94R+D111S+S216P+L227G+T231R+N233R+D254S+P256T;
D27R+N33Q+E56Q+D57N+G91N+N94R+D111S+S216P+L227G+T231R+N233R+D242E+D254S+P256T;
D27R+N33Q+G38A+E56Q+D57N+G91N+N94R+D111S+S216P+L227G+T231R+N233R+D254S+P256T;
N33Q+G38A+G91T+G163A+T231R+N233R+D254S;
N11R+N33Q+190L+G163L+T231R+N233R+D254S;
N11R+N33Q+E56Q+G91T+G163K+V176Q+T231R+N233R+D254S;
N11R+D27R+N33Q+G91T+D96E+D111A+G163K+T231R+N233R+D254S+P256T;
N11R+N33Q+G38A+G91T+G112A+G163A+T231R+N233R+D254S;
N11R+N33Q+G91T+G163K+E210D+T231R+N233R+D254S;
N11R+N33Q+G91T+G163K+V176T+T231R+N233R+D254S;
N11R+N33Q+G91T+G163P+T231R+N233R+D254S;
N11R+N33Q+G91M+G163T+T231R+N233R+D254S;
N11R+N33Q+G38A+G91T+G163K+V176D+T231R+N233R+D254S;
N11R+N33Q+E56Q+G91T+G163K+T231R+N233R+D254S;
N11R+N33Q+190L+G163K+T231R+N233R+D254S;
D27R+N33Q+E56Q+D57N+G91N+N94R+D111S+S216P+L227G+T231R+N233R+Q249R+D254S+P256T;
D27R+N33Q+E56Q+D57N+G91N+N94R+D111S+S216P+E219D+L227G+T231R+N233R+D254S+P256T;
N11R+N33Q+190L+G91T+N94S+D96E+G163K+T231R+N233R+D254S;
N11R+N33Q+G91T+G163K+V176I+T231R+N233R+D254S;
N11R+N33Q+G91T+G163K+V176Q+T231R+N233R+D254S;
N11R+N33Q+G91T+G163A+V176T+T231R+N233R+D254S;
N11R+N33Q+G91T+G163L+V176I+T231R+N233R+D254S;
N11R+N33Q+G91T+G163L+V176T+T231R+N233R+D254S;
N11R+N33Q+G91T+G163L+T231R+N233R+D254S;
N11R+N33Q+G91T+G163P+T231R+N233R+D254S;
N11R+N33Q+G91T+G163P+V176I+T231R+N233R+D254S;
N11R+N33Q+G91T+G163L+T231R+N233R+D254S+P256N;
D27R+N33Q+E56Q+D57N+G91N+N94R+D111S+G163T+S216P+L227G+T231R+N233R+Q249R+D254S+P256T;
D27R+N33Q+L227G+T231R+N233R+Q249R+D254S;
N33Q+G38A+G91T+G163K+T231R+N233R+D254S;
N8L+N11R+N33Q+G91T+G163K+T231R+N233R+D254S;
N11R+N33Q+G38A+G91T+G163P+V176G+T231R+N233R+D254S;
N11R+N33Q+G91T+G163K+T231R+N233R+D254S+P256F;
N11R+N33Q+G38A+G91T+G156R+G163K+V176T+T231R+N233R+D254S;
N11R+N33Q+G91T+G163N+T231R+N233R+D254S;
N11R+N33Q+G91T+G163T+T231R+N233R+D254S;
N11R+N33Q+G91T+G163W+T231R+N233R+D254S;
N11R+N33Q+G91K+G163K+T231R+N233R+D254S;
N11R+G23E+N33Q+G91T+G163K+T231R+N233R+D254S;
N11R+N33Q+G91T+V141E+G163K+T231R+N233R+D254S;
N11R+N33Q+L52R+G91T+G163K+T231R+N233R+D254S;
N11R+N33Q+G91T+V141L+G163K+T231R+N233R+D254S;
N11R+N33Q+T37K+G91T+G163K+T231R+N233R+D254S;
N11R+N33Q+A68V+G91T+G163K+T231R+N233R+D254S;
N11R+N33Q+G91T+G163A+V176I+T231R+N233R+D254S;
N11R+N33Q+T37M+G91T+G163P+V176T+T231R+N233R+D254S;
N11R+N33Q+G91T+G163L+T231R+N233R+D254S;
N11R+N33Q+G91T+G163K+T231R+N233R+D254S+P256I;
N11R+D27R+N33Q+E56Q+D57N+G91N+N94R+D111S+G163K+S216P+L227G+T231R+N233R+D254S+P256T;
N11R+N33Q+G38A+G91T+G163P+V176G+T231R+N233R+D254S;
N11R+N33Q+G38A+G91T+G163Q+V176G+T231R+N233R+D254S;
N11R+N33Q+G38A+G91T+G163T+V176G+T231R+N233R+D254S;
N11R+N33Q+G38A+G91T+N94R+G163P+V176G+T231R+N233R+D254S;
E1*+N11R+N33Q+G38A+G91N+N94R+G163P+V176G+T231R+N233R+D254S;
E1N+N33Q+G38A+G91T+G163P+V176F+T231R+N233R+D254S;
E1N+N33Q+G38A+G91T+G163P+V176F+L227F+T231R+N233R+D254S;
E1N+N33Q+G38A+G91T+G163P+V176F+T231R+N233R+D254S+1255A+P256Q;
E1N+N11R+N33Q+G38A+G91T+D111A+G163P+V176F+T231R+N233R+D254S;
N11R+N33Q+G38A+G91T+D102G+S115L+G163K+T231R+N233R+D254S+P256T;
N11R+N33Q+G38A+G91T+S115L+G163K+T231R+N233R+D254S+P256T;
E1N+N11R+N33Q+G91T+G163A+T231R+N233R+G246A+D254S;
N11R+D27R+N33Q+D57G+G91T+D96E+D111A+G163K+T231R+N233R+D254S+P256T;
N11C+N33Q+G91T+G163K+T231R+N233R+D254S;
N11L+N33Q+G91T+G163K+T231R+N233R+D254S;
N11H+N33Q+G91T+G163K+T231R+N233R+D254S;
N11D+N33Q+G91T+G163K+T231R+N233R+D254S;
N11R+N33Q+G91T+D96W+G163K+T231R+N233R+D254S;
D27R+N33Q+G91T+D96E+L97Q+D111A+G163K+T231R+N233R+D254S+P256T;
N11P+N33Q+G91T+G163K+T231R+N233R+D254S;
N11R+N33Q+E56Q+G163K+T231R+N233R+D254S;
N11R+N33Q+G91T+G163A+T231R+N233R+D254S;
N11R+N33Q+G91T+G163P+T231R+N233R+D254S;
N11R+N33Q+G91T+G163K+L227G+P229R+T231R+N233R+D254S;
N33Q+G91T+K98I+T114I+G163K+T231R+N233R+D254S;
N33Q+G91T+K98I+G163K+T231R+N233R+D254S+P256L; and
N33Q+G91T+T114I+G163K+T231R+N233R+D254S+P256L.

2. The lipase of claim 1 in combination with a protease or an amylase.

3. The lipase of claim 1, in combination with a protease and an amylase.

4. The lipase in combination with a protease or an amylase according to claim 2, wherein
   - (i) the protease has at least 90% identity to a protease selected from the group consisting of
     - a) a protease having the sequence of amino acids 1-274 of SEQ ID NO: 3,
     - b) a protease having the sequence of amino acids 1-188 of SEQ ID NO: 4, and
     - c) a protease having the sequence of amino acids 1-188 of SEQ ID NO: 5;
   - (ii) the amylase has at least 90% identity to an amylase selected from the group consisting of
     - a) an amylase having the sequence of amino acids 1-481 of SEQ ID NO: 6,
     - b) an amylase having the sequence of amino acids 1-481 of SEQ ID NO: 7, and
     - c) an amylase having the sequence of amino acids 1-483 of SEQ ID NO: 8.

5. A pharmaceutical composition comprising a lipase or a mixture of lipases as defined in claim 1, together with at least one pharmaceutically acceptable auxiliary material.

6. The composition of claim 5, further comprising a protease or an amylase.

7. The composition of claim 5, further comprising a protease and an amylase.

8. The composition of claim 5, wherein
   - (i) the protease has at least 90% identity to a protease selected from the group consisting of
     - a) a protease having the sequence of amino acids 1-274 of SEQ ID NO: 3,
     - b) a protease having the sequence of amino acids 1-188 of SEQ ID NO: 4, and
     - c) a protease having the sequence of amino acids 1-188 of SEQ ID NO: 5;
   - (ii) the amylase has at least 90% identity to an amylase selected from the group consisting of
     - a) an amylase having the sequence of amino acids 1-481 of SEQ ID NO: 6,
     - b) an amylase having the sequence of amino acids 1-481 of SEQ ID NO: 7, and
     - c) an amylase having the sequence of amino acids 1-483 of SEQ ID NO: 8.

9. The lipase of claim 1, which is N33Q+T231R+N233R+D254S.

10. The lipase of claim 1, which is N11R+N33Q+G91T+G163K+T231R+N233R+D254S.

11. The lipase of claim 1, which is N33Q+G91T+K98I+T114I+G163K+T231R+N233R+D254S.

12. The lipase of claim 1, which is D27R+N33Q+G38A+G91T+D96E+D111A+G163K+T231R+N233R+D254S+P256T.

13. The lipase of claim 1, which is N11R+D27R+N33Q+G91T+D96E+D111A+G163K+T231R+N233R+D254S+P256T.

14. A method of treating a digestive disorder in an animal, comprising administering to the animal a therapeutically effective amount of the lipase of claim 1 and a pharmaceutically acceptable auxiliary material.

15. The method of claim 14, wherein the digestive disorder is maldigestion or dyspepsia.

16. The method of claim 14, further comprising administering a protease or an amylase.

17. A method of treating pancreatic exocrine insufficiency, pancreatitis, cystic fibrosis, diabetes type I, and/or diabetes type II in an animal, comprising administering to the animal a therapeutically effective amount of the lipase of claim 1 and a pharmaceutically acceptable auxiliary material.

18. The method of claim 17, wherein the pancreatitis is acute pancreatitis.

19. The method of claim 17, wherein the pancreatitis is chronic pancreatitis.

20. The method of claim 17, further comprising administering a protease or an amylase.

21. The method of claim 14, further comprising administering a protease and an amylase.

22. The method of claim 17, further comprising administering a protease and an amylase.

23. The lipase of claim 1, which has at least 95% identity to the sequence of amino acids 1-269 of SEQ ID NO: 2.

24. The lipase of claim 1, which has at least 97% identity to the sequence of amino acids 1-269 of SEQ ID NO: 2.

25. The lipase of claim 1, which has at least 99% identity to the sequence of amino acids 1-269 of SEQ ID NO: 2.

* * * * *